United States Patent
Kay et al.

(10) Patent No.: US 10,006,047 B2
(45) Date of Patent: Jun. 26, 2018

(54) NON-SILENCING SELECTABLE MARKER GENES AND METHODS OF USE

(71) Applicant: The Board of Trustees of the Leland Stanford Junior University, Stanford, CA (US)

(72) Inventors: Mark A. Kay, Los Altos, CA (US); Jiamiao Lu, Mountain View, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 10 days.

(21) Appl. No.: 15/019,838

(22) Filed: Feb. 9, 2016

(65) Prior Publication Data
US 2016/0237454 A1 Aug. 18, 2016

Related U.S. Application Data

(60) Provisional application No. 62/116,197, filed on Feb. 13, 2015, provisional application No. 62/117,909, filed on Feb. 18, 2015.

(51) Int. Cl.
| | |
|---|---|
| *C12N 15/85* | (2006.01) |
| *A61K 31/713* | (2006.01) |
| *C07K 14/245* | (2006.01) |
| *C12N 9/12* | (2006.01) |
| *C12N 9/86* | (2006.01) |

(52) U.S. Cl.
CPC ............ *C12N 15/85* (2013.01); *A61K 31/713* (2013.01); *C07K 14/245* (2013.01); *C12N 9/1205* (2013.01); *C12N 9/86* (2013.01)

(58) Field of Classification Search
CPC ..... C12N 15/85; C07K 14/245; A61K 31/713
See application file for complete search history.

(56) References Cited

U.S. PATENT DOCUMENTS

| 2009/0311786 A1 | 12/2009 | Fire et al. |
| 2011/0123993 A1 | 5/2011 | Suzuki et al. |
| 2014/0273225 A1 | 9/2014 | Lu et al. |

FOREIGN PATENT DOCUMENTS

| WO | 2004/070030 A1 | 8/2004 |

OTHER PUBLICATIONS

Yew et al., "Reduced inflammatory response to plasmid DNA vectors by elimination and inhibition of immunostimulatory CpG motifs", Molecular Therapy, Mar. 2000, pp. 255-262, vol. 1, No. 3, The American Society of Gene Therapy, Milwaukee, WI.
Yew et al., "CpG-depleted plasmid DNA vectors with enhanced safety and long-term gene expression in vivo", Molecular Therapy, Jun. 2002, pp. 731-738, vol. 5, No. 6, The American Society of Gene Therapy, Milwaukee, WI.
Bao et al., "Nucleosome core particles containing a poly(dA.dT) sequence element exhibit a locally distorted DNA structure", J Mol Biol, Aug. 2006, pp. 617-624, vol. 361, No. 4, Elsevier, Amsterdam, Netherlands.
Belch et al., "Weakly Positioned Nucleosomes Enhance the Transcriptional Competency of Chromatin" PLOS One, Sep. 2010, p. 1-14, vol. 5, No. 9, PLOS One, San Francisco, CA.
Blow et al., "Chromosome replication in cell-free systems from Xenopus eggs" Philos Trans R Soc Lond B Biol Sci, Dec. 15, 1987, pp. 483-494, vol. 317, No. 1187, JSTOR, Ann Arbor, MI.
Cameron, "Recent Advances in Transgenic Technology" Molecular Biotechnology, 1997, pp. 253-265, vol. 7, No. 3, Humana Press, Totowa,New Jersey.
Chen et al., "Minicircle DNA vectors devoid of bacterial DNA result in persistent and high-level transgene expression in vivo" Mol Ther, Sep. 2003, pp. 495-500, vol. 8, No. 3, The American Society of Gene Therapy, Milwaukee, WI.
Chen et al., "Silencing of episomal transgene expression by plasmid bacterial DNA elements in vivo" Gene Ther, Mar. 18, 2004, pp. 856-864, vol. 11, No. 10, Nature Publishing Group, London, United Kingdom.
Claeys Bouuaert et al., "A simple topological filter in a eukaryotic transposon as a mechanism to suppress genome instability" Mol Cell Biol, Jan. 2011, pp. 317-327, vol. 31, No. 2, American Society for Microbiology, Washington, D.C.
Datta et al., "Nucleosomal occupancy and CGG repeat expansion: a comparative analysis of triplet repeat region from mouse and human fragile X mental retardation gene 1" Chromosome Res, May 2011, pp. 445-455, vol. 19, No. 4, Springer, New York, NY.
Ehrhardt et al., "A new adenoviral helper-dependent vector results in long-term therapeutic levels of human coagulation factor IX at low doses in vivo" Blood, Jun. 2002, pp. 3923-3930, vol. 99, No. 11, American Society of Hematology, Washington, D.C.
Ganapathi et al., "A whole genome analysis of %' regulatory regions of human genes for putative cis-acting modulators of nucleosome positioning" Gene, Apr. 2007, pp. 242-251, vol. 391, No. 1-2, Elsevier, Amsterdam, Netherlands.
Hino et al., "Sea urchin arylsulfatase insulator exerts its antisilencing effect without interacting with the nuclear matrix" J Mol Biol, Mar. 2006, pp. 18-27, vol. 357, No. 1, Elsevier, Amsterdam, Netherlands.

(Continued)

*Primary Examiner* — Antonio Galisteo Gonzalez
(74) *Attorney, Agent, or Firm* — Kyle A. Gurley; Bozicevic, Field & Francis LLP

(57) ABSTRACT

Provided are nucleic acids and expression vectors having a non-silencing selectable marker gene, and methods of using the same. A subject expression vector includes an expression cassette and a non-silencing selectable marker gene. In some cases, the non-silencing selectable marker gene provides for drug resistance for prokaryotic cells, and includes a nucleotide sequence that (i) encodes a drug selectable marker protein; (ii) is operably linked to a promoter functional in prokaryotic cells, and (iii) includes an increased A/T content relative to a corresponding wild type nucleotide sequence. In some cases, the non-silencing selectable marker gene provides for drug resistance for prokaryotic cells, and includes a nucleotide sequence that (i) encodes a drug selectable marker protein; (ii) is operably linked to a promoter functional in prokaryotic cells, and (iii) has an A/T content in a range of from 52% to 70%.

31 Claims, 14 Drawing Sheets

(56) References Cited

OTHER PUBLICATIONS

Lu et al., "The Extragenic Spacer Length Between the 5' and 3' Ends of the Transgene Expression Cassette Affects Transgene Silencing From Plasmid-based Vectors" Mol Ther, Nov. 2012, pp. 2111-2119, vol. 20, No. 11, The American Society of Gene & Cell Therapy, Milwaukee, WI.

Lyer et al., "Mechanism of differential utilization of the his3 TR and TC TATA elements" Mol Cell Biol, Dec. 1995, pp. 7059-7066, vol. 15, No. 12, American Society for Microbiology, Washington, D.C.

Montecino et al., "Nucleosome organization and targeting of SWI/SNF chromatin-remodeling complexes: contributions of the DNA sequence" Biochem Cell Bio, Aug. 2007, pp. 419-425, vol. 85, No. 4, National Research Council Canada, Ottawa, Ontario.

Montoliu, "Gene Transfer Strategies in Animal Transgenesis" Cloning and Stem Cells, 2002, pp. 39-46, vol. 4, No. 1, Mary Ann Liebert, Inc., New Rochelle, NY.

Nakai et al., "Extrachromosomal recombinant adeno-associated virus vector genomes are primarily responsible for stable liver transduction in vivo" J Virol, Aug. 2001, pp. 6969-6976, vol. 75, No. 15, American Society for Microbiology, Washington, D.C.

Niemann, "Transgenic farm animals get off the ground" Transgenic Research, 1998, pp. 73-75, vol. 7, No. 1, Chapman & Hall, Boca Raton, Florida.

Prelle et al., "Establishment of Pluripotent Cell Lines from Vertebrate Species—Present Status and Future Prospects" Cells Tissues Organs, Jun. 10, 1999, pp. 220-236, vol. 165, No. 3-4, Karger Publishers, Basel, Switzerland.

Ristevski, "Making Better Transgenic Models—Conditional, Temporal and Spatial Approaches" Molecular Biotechnology, 2005, pp. 153-163, vol. 29, Humana Press, Totowa,New Jersey.

Segal et al., "From DNA sequence to transcriptional behavior: a quantitate approach" Nat Rev Genet, Jul. 2009, pp. 443-456, vol. 10, No. 7, Nature Publishing Group, London, United Kingdom.

Segal et al., "Poly(dA:dT) tracts: major determinants of nucleosome organization" Curr Opin Struct Biol, Feb. 2009, pp. 65-71, vol. 19, No. 1, Elsevier, Amsterdam, Netherlands.

Segal et al., "What controls nucleosome positions?" Trends Genet, Aug. 2009, pp. 335-343, vol. 25, No. 8, Cell Press, Cambridge, MA.

Sigmund, "Viewpoint: Are Studies in Genetically Altered Mice Out of Control?" Arteriosclerosis, Thrombosis, and Vascular Biology, 2000, pp. 1425-1429, vol. 20, No. 6, American Heart Association, Dallas, TX.

Taton et al., "Broad-host-range vector system for the synthetic biology and biotechnology in cyanobacteria" Nucleic Acids Research, Jul. 2014, pp. 1-16, vol. 42, No. 17, Oxford University Press, Oxford, United Kingdom.

Waterborg et al., "Common features of analogous replacement histone H3 genes in animals and plants" J Mol Evol, Sep. 1996, pp. 194-206, vol. 43, No. 3, Springer, New York, NY.

Xu et al., "Genome-wide identification and characterization of replication origins by deep sequencing" Genome Biol, Apr. 2012, pp. 1-14, vol. 13, No. 4, BioMed Central Ltd., London, United Kingdom.

Yasuda et al., "Nucleosomal structure of undamaged DNA regions suppresses the non-specific DNA binding of the XPC complex" DNA Repair, Mar. 2005, pp. 389-395, vol. 4, No. 3, Elsevier, Amsterdam, Netherlands.

Yu et al., "Mechanism of the Long Range Anti-Silencing Function of Targeted Histone Aceytltransferases in Yeast" The Journal of Biological Chemistry, Feb. 17, 2006, pp. 3980-3988, vol. 281, No. 7, ASBMB, Rockville, MD.

Yuan et al., "Genome-scale identification of nucleosome positions in S. cerevisiae" Science, Jul. 22, 2005, pp. 626-630, vol. 309, No. 5734, AAAS, Washington, DC.

Smith, "Gene transfer in higher animals: theoretical considerations and key concepts", Journal of Biotechnology, Apr. 17, 2002, pp. 1-22, 99, Elsevier, Amsterdam, Netherlands.

Tillo et al. "High nucleosome occupancy is encoded at human regulatory sequences", PLoS One, Feb. 9, 2010, pp. 1-5, vol. 5, Issue 2, PLOS One, San Francisco, CA.

Figure 1

```
actagtctgcagTTTTTTTTTTTTTTTTTTTTGTCGACTCCGGCGAACGACTATATTATCAGCTT
ACGATCCCCGCGGAGCCTTCCGATTCTTTTTTTTTTTTTTTTTTCCGGCTCTTACTACCTCG
CCTCCGTAGGCCCGCGGCTAGTTTCTATCCTCCAACGTAAATTTTTTTTTTTTTTTTTTTCCC
GAGCCGAGCTGTGACTCCCGAAGGCCGGTCTCCTGTCACGTATCCGGTGGCTGTGCGTTTTTTTT
TTTTTTTTTTTTCGTACACCACCAGCCGGGTCGGCGAGTCTATTGCATAGTTTTGCGAGCGAATA
TGCTTTGTTTTTTTTTTTTTTTTTTCCCTTTCACGGTGCTGGTATCATGCCGCGGCGCTCCAT
CCACTTCTCTCCCTTGCTTATCTTTTTTTTTTTTTTTTTGCGCCTACCATCCCTATACAGAC
GTCGGAGTTCGTTTCTCGAAACTGTCTTTCCGACAGCTTTTTTTTTTTTTTTTTTTCGGATTCC
ACCGGGCGCAGCGTTCCTCTCGAGCGGCGGTAGCACGTCTTACAGACAGTTCTTTTTTTTTTTT
TTTTTTTCCGGCTTCGAGTTGAACATTCTGCATCTTAACCTTCATTTATTCCATTCTCGCGAGCC
GCTTTTTTTTTTTTTTTTTTTCGATCTACTGAGACAGCGAGCGTTCCATCGTTCTTTCTTCTTT
CTTTCGCGGCGAGACCCTTTTTTTTTTTTTTTTTTTACCTTCCGGGCGCCGCGCGGCGGGTTTA
CTTACTACTCGCGGAGTTAAGCGGCCCTGCCGTTTTTTTTTTTTTTTTTTTTGGCGCGGCTCCAC
CGCGCCTCGACGTAGGGTGTCTTCCGGGGGGGTTTACATACTATTCCTTTTTTTTTTTTTTTTTT
TTAGCGTTCTTGTTATTTTCCCGCGGCGGCTTTAGACTATCGGCTGTTCGGCCTTCTTCTTCTTT
TTTTTTTTTTTTTTTTTCCTTCGATCGCCAGGCAGGAGTCTCAAGTTCTCGCGAGTATCTGCTTT
GTTTTTATTCATTTTTTTTTTTTTTTTTTTAATACCTCCGACTAGCCAAATCTTTCTCCGTTG
GGTCCCATCTTATATTCCAGCTCAGAGTTTTTTTTTTTTTTTTTTTCCCTCGCATCGCCTGCGC
TCCCTCCGCAGTTTTCCTTGCGGGATTCTACTCGATAACCTGTTTTTTTTTTTTTTTTTTTTCTT
GCTTATCCGGAATCCGTAGTACGTCCGCGCGGTACTCGAGCGTATCTGCCCATCCTATTTTTTTT
TTTTTTTTTTTTCTATATCTTTCTGCGTTCTAGCGTCGACCCCGCGCCTCATTTAGACAGGGCCT
GGAGTTATTTTTTTTTTTTTTTTTTGTCCTGGCTCCAGCTGGCCACGATTTTATATAGCCCCT
CTCCTATTCTGGCTCCCGGGATTTTTTTTTTTTTTTTTTATGACGAAAGCTTGAATTCTTCT
ATTCCCGCCGCGGGATGAGGCCGGTGGCGTGATTCATTTTTTTTTTTTTTTTTTTTTGCGGACTA
TGCCCCGCGGTGCCGGGTCGGCGCGTCGCGATTTTTCTCCGCGGGCCAGGCTTTTTTTTTTTT
TTTTTTGGTGGCTCCCTAAAGTTGCTCCAGGCGCGGTCGCCAATGGGAGAACTCTAATCGCTCC
CGTTTTTTTTTTTTTTTTTTTTCTTCTTCTACGATTCGCTAAGACACCTGCGCAAGGGCTTAATC
TTCCCAGCTGTTTCTAGTTTTTTTTTTTTTTTTTTTGCGGTTTCCCCCAGACCCGCGCGGGCG
TCATGTATGCTCGACGGGTTCCTTCCCGCGTGTTTTTTTTTTTTTTTTTTATGTTTCCACGC
GTGATTTTCTGGGCTGAGGCCACGCTCTACTACACCAGTCAATTATGTTTTTTTTTTTTTTTTTTT
TTAGTTACTCCCCACTCAACTTTCCATGCGGCTTTTACGCCCGCGGCTATAAGCGTCAAGTTTTT
TTTTTTTTTTTTTTTCTATCATTTTATAGCGGACTATACGCCTGTAAACTTCGAGACCGGATC
CTGGTCCGAAAGTTTTTTTTTTTTTTTTTTTTAAAGATTATTTATCTCTTTACACTATCGCCCCG
GTTGCTTTGTACTCCAGCCATTAAACATTTTTTTTTTTTTTTTTTTTctgcagactagt
```

(SEQ ID NO: 1)

Figure 4A
Figure 4B
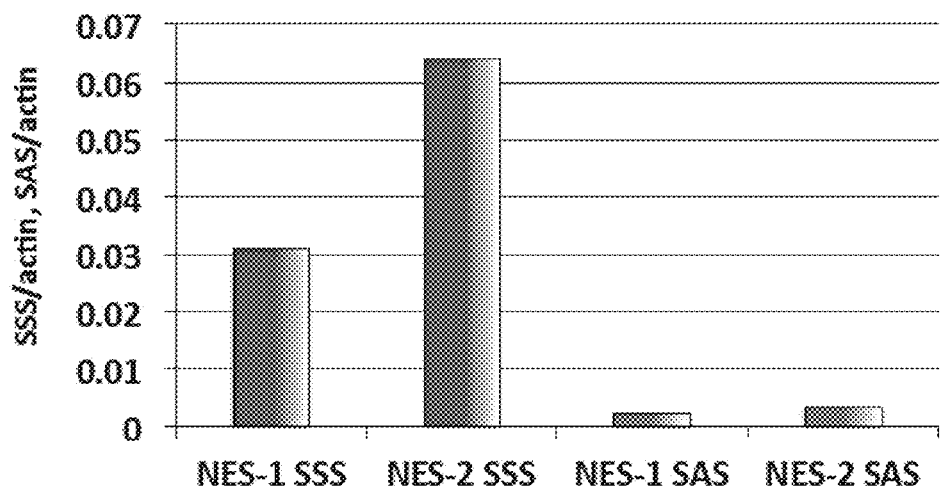
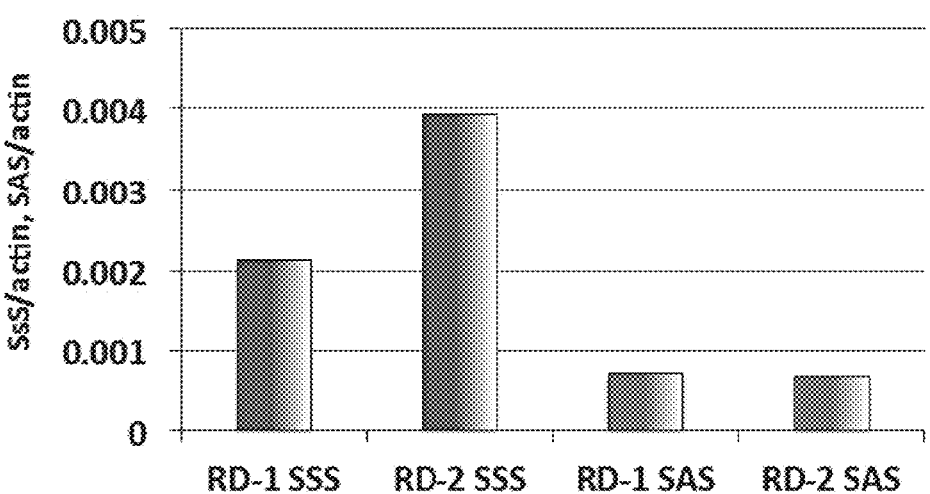

Figure 4C
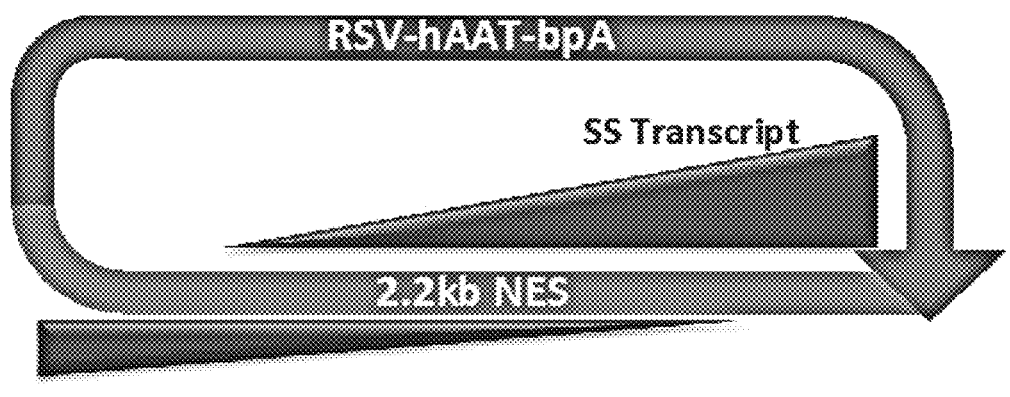
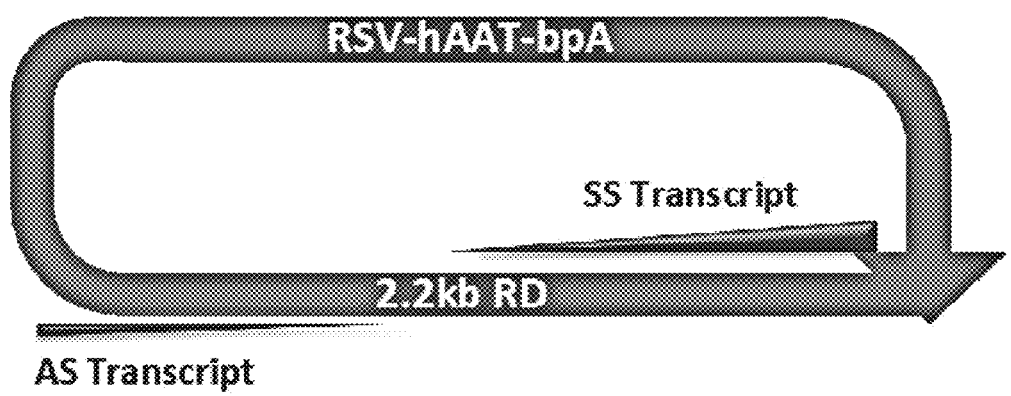

Figure 5A
Pol II arrest site 1: TTTTTTTCCCTTTTTT (16nt) (H3.3)
Figure 5B
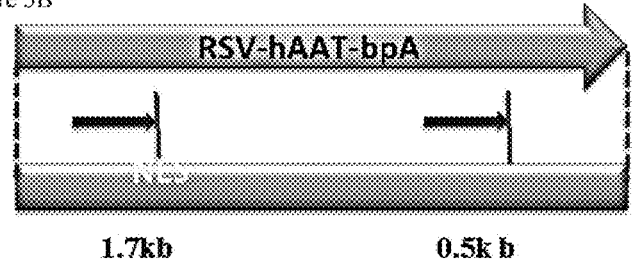
Figure 5C
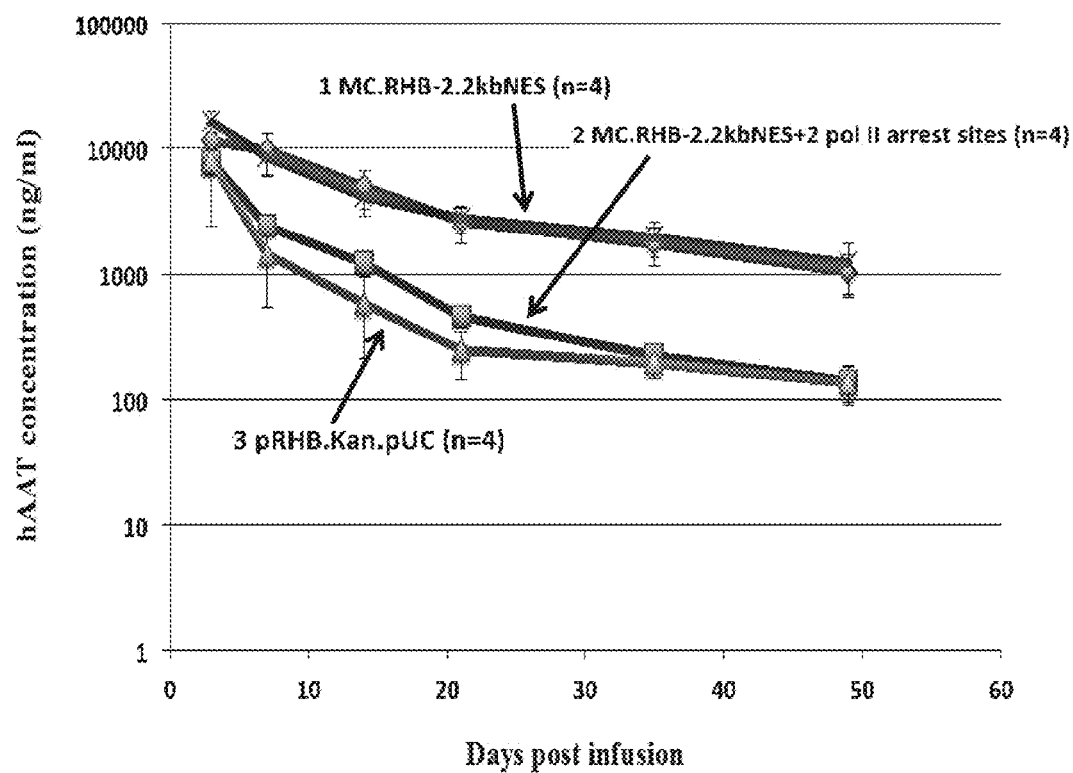

Figure 6
Nucleotide sequence encoding Kanamycin (Kan) resistance protein
ATGATTGAACAAGATGGATTGCACGCAGGTTCTCCGGCCGCTTGGGTGGA
GAGGCTATTCGGCTATGACTGGGCACAACAGACAATCGGCTGCTCTGATG
CCGCCGTGTTCCGGCTGTCAGCGCAGGGGCGCCCGGTTCTTTTTGTCAAG
ACCGACCTGTCCGGTGCCCTGAATGAACTGCAGGACGAGGCAGCGCGGCT
ATCGTGGCTGGCCACGACGGGCGTTCCTTGCGCAGCTGTGCTCGACGTTG
TCACTGAAGCGGGAAGGGACTGGCTGCTATTGGGCGAAGTGCCGGGGCAG
GATCTCCTGTCATCCCACCTTGCTCCTGCCGAGAAAGTATCCATCATGGC
TGATGCAATGCGGCGGCTGCATACGCTTGATCCGGCTACCTGCCCATTCG
ACCACCAAGCGAAACATCGCATCGAGCGAGCACGTACTCGGATGGAAGCC
GGTCTTGTCGATCAGGATGATCTGGACGAAGAGCATCAGGGGCTCGCGCC
AGCCGAACTGTTCGCCAGGCTCAAGGCGCGCATGCCCGACGGCGAGGATC
TCGTCGTGACCCATGGCGATGCCTGCTTGCCGAATATCATGGTGGAAAAT
GGCCGCTTTTCTGGATTCATCGACTGTGGCCGGCTGGGTGTGGCGGACCG
CTATCAGGACATAGCGTTGGCTACCCGTGATATTGCTGAAGAGCTTGGCG
GCGAATGGGCTGACCGCTTCCTCGTGCTTTACGGTATCGCCGCTCCCGAT
TCGCAGCGCATCGCCTTCTATCGCCTTCTTGACGAGTTCTTCTGA
(SEQ ID NO: 2)

"J-Kan" sequence (Nucleotide sequence encoding same protein as above)
ATGATTGAACAAGATGGATTACATGCAGGTTCTCCAGCAGCTTGGGT**TGA
ACGTTTGTTTGGATATGATTGGGCACAACAACAATTGGTTG**TTCTGATG
CTGCTGTTTTTCGTCTTTCTGCTCAAGGACGTCCTGTTCTTTTTGTAAA**
ACA**GATCTTTCTGGTGCTTTAAATGAATTACAAGATGAAGCAGCACGTTT
ATCTTGGTTAGCAACAACAGGAGTTCCTTGTGCAGCTGTTTAGATGTTG
TTACTGAAGCAGGACGTGATTGGTTATTATTAGGAGAAGTTCCTGGACAA
GATTACTTTCATCTCATCTTGCTCCTGCAGAAAAGTATCAATTATGGC
TGATGCAATGCGGCGTTTACATACACTTGATCCAGCTACTTGTCCATTTG
ATCATCAAGCAAAACATCGTATTGAACGTGCACGTACTCGTATGGAAGCA
GGTCTTGTTGATCAAGATGATTAGATGAAGAGCATCAAGGATTAGCACC
AGCTGAATTATTCGCTCGTTAAAAGCACGTATGCCTGATGGTGAAGATT
TAGTAGTTACACATGGAGATGCTTGTTACCAAATATTATGGTAGAAAAT
GGACGTTTTCTGGTTTATCGATTGTGGACGTTAGGTGTAGCAGATCG
TTATCAAGATATTGCTTTAGCTACACGTGATATTGCTGAAGAATTAGGAG
GAGAATGGGCTGATCGTTTTTAGTATTATATGGTATTGCAGCTCCAGAT
TCACAACGTATTGCTTTTATCGTCTTTAGATGAATTTTTCTGA
(SEQ ID NO: 4)

Figure 8

"JT-Kan" sequence
(Nucleotide sequence encoding same protein as Figure 6, top)
atgattgaGcaGgatggTCtTcaTgcTggttctccTgcTgcttgggtTgagCgCctTtt
TggTtatgaTtgggcTcaGcagacTatTggTtgTtctgatgcTgcTgtTttTcgCctTt
cTgcTcagggTcgcccTgttcttttgtTaagacTgaTctTtcTggtgcTTtgaatgaG
ctTcaggaTgaggcTgcTcgCctTtcTtggcTgcTacTacTggTgttccttgTgcTgc
tgtTctTgaTgttgtTactgaGgcTggTCgCgaTtggcTTctTttgggTgaGgtTccTg
gTcaggatctTTtgtcTtcTcaTcttgctcctgcTgagaaGgtTtcTatTatggctgat
gcTatgcgCcgCctTcatacTcttgatccTgctacTtgTccTttTgaTcaTcaGgcTaa
GcatcgcatTgagcgCgcTcgtactcgCatggaGgcTggtcttgtTgatcaggatgatc
tTgaTgaGgagcatcagggTctTgcTccTgcTgaGctTttTgcTCgCctTaaggcTcgc
atgccTgaTggTgaggatctTgtTgtTacTcatggTgatgcTtgcCtTccTaatatTat
ggtTgaGaatggTcgctttctggTttTatTgaTtgtggTcgCctTggtgtTgcTgaTc
gctatcaggaTatTgcTtttggctacTcgCgatattgctgaGgagcttggTggTgaGtgg
gctgaTcgcttTTtGgtTcttaTggtatTgcTgctccTgattcTcagcgcatTgcTtt
TtatcgcctTtTtGgaTgagttTttTtga (SEQ ID NO: 5)

Figure 9

Nucleotide sequence encoding Ampicillin (Amp) resistance protein
ATGAGTATTCAACATTTCCGTGTCGCCCTTATTCCCTTTTTTGCGGCATTTTGCCTTCC
TGTTTTTGCTCACCCAGAAACGCTGGTGAAAGTAAAAGATGCTGAAGATCAGTTGGGTG
CACGAGTGGGTTACATCGAACTGGATCTCAACAGCGGTAAGATCCTTGAGAGTTTTCGC
CCCGAAGAACGTTTTCCAATGATGAGCACTTTTAAAGTTCTGCTATGTGGCGCGGTATT
ATCCCGTATTGACGCCGGGCAAGAGCAACTCGGTCGCCGCATACACTATTCTCAGAATG
ACTTGGTTGAGTACTCACCAGTCACAGAAAAGCATCTTACGGATGGCATGACAGTAAGA
GAATTATGCAGTGCTGCCATAACCATGAGTGATAACACTGCGGCCAACTTACTTCTGAC
AACGATCGGAGGACCGAAGGAGCTAACCGCTTTTTTGCACAACATGGGGGATCATGTAA
CTCGCCTTGATCGTTGGGAACCGGAGCTGAATGAAGCCATACCAAACGACGAGCGTGAC
ACCACGATGCCTGTAGCAATGGCAACAACGTTGCGCAAACTATTAACTGGCGAACTACT
TACTCTAGCTTCCCGGCAACAATTAATAGACTGGATGGAGGCGGATAAAGTTGCAGGAC
CACTTCTGCGCTCGGCCCTTCCGGCTGGCTGGTTTATTCCTGATAAATCTGGAGCCGGT
GAGCGTGGGTCTCGCGGTATCATTGCAGCACTGGGGCCAGATGGTAAGCCCTCCCGTAT
CGTAGTTATCTACACGACGGGGAGTCAGGCAACTATGGATGAACGAAATAGACAGATCG
CTGAGATAGGTGCCTCACTGATTAAGCATTGGTAA
                                        (SEQ ID NO: 11)

J-Amp sequence (Nucleotide sequence encoding same protein as above)
ATGAGTATTCAACATTTTCGTGTTGCTTTAATTCCTTTTTTTGCTGCTTTTTGTTTACC
TGTTTTTGCTCATCCAGAAACATTAGTTAAAGTTAAAGATGCTGAAGATCAATTAGGTG
CACGAGTTGGTTATATTGAATTAGATTTAAATAGTGGTAAAATTTTAGAAAGTTTTCGT
CCTGAAGAACGTTTTCCAATGATGAGTACTTTTAAAGTTTTACTATGTGGTGCTGTTTT
ATCTCGTATTGATGCTGGTCAAGAACAATTAGGTCGTCGTATTCACTATTCTCAAAATG
ATTTAGTTGAATATTCTCCAGTTACAGAAAAACATTTAACAGATGGAATGACAGTAAGA
GAATTATGTAGTGCTGCTATTACAATGAGTGATAATACTGCTGCTAATTTACTTTTAAC
AACAATTGGAGGACCAAAAGAATTAACAGCTTTTTTACATAATATGGGTGATCATGTTA
CTCGTTTAGATCGTTGGGAACCAGAATTAAATGAAGCAATTCCAAATGATGAACGTGAT
ACAACAATGCCTGTTGCAATGGCAACAACATTACGTAAACTATTAACTGGTGAATTACT
TACTTTAGCTTCTCGTCAACAATTAATTGATTGGATGGAAGCAGATAAAGTTGCAGGAC
CATTACTTCGTTCTGCTTTACCTGCTGGTTGGTTTATCGCTGATAAATCTGGAGCAGGT
GAACGTGGTTCTCGTGGTATCATTGCAGCATTAGGTCCAGATGGTAAACCTTCTCGTAT
TGTTGTTATCTATACAACAGGAAGTCAAGCAACTATGGATGAACGAAATCGTCAAATTG
CTGAAATTGGTGCTTCATTAATTAAACATTGGTAA
                                        (SEQ ID NO: 13)

Figure 11
Nucleotide sequence encoding tetracycline (Tet) resistance protein
atgaaatctaacaatgcgctcatcgtcatcctcggcaccgtcaccctggatgctgtaggcatagg
cttggttatgccggtactgccgggcctcttgcgggatatcgtccattccgacagcatcgccagtc
actatggcgtgctgctagcgctatatgcgttgatgcaatttctatgcgcacccgttctcggagca
ctgtccgaccgctttggccgccgcccagtcctgctcgcttcgctacttggagccactatcgacta
cgcgatcatggcgaccacacccgtcctgtggatcctctacgccggacgcatcgtggccggcatca
ccggcgccacaggtgcggttgctggcgcctatatcgccgacatcaccgatggggaagatcgggct
cgccacttcgggctcatgagcgcttgtttcggcgtgggtatggtggcaggccccgtggccggggg
actgttgggcgccatctccttgcatgcaccattccttgcggcggcggtgctcaacggcctcaacc
tactactgggctgcttcctaatgcaggagtcgcataagggagagcgtcgaccgatgcccttgaga
gccttcaacccagtcagctccttccggtgggcgcggggcatgactatcgtcgccgcacttatgac
tgtcttctttatcatgcaactcgtaggacaggtgccggcagcgctctggtcattttcggcgagg
accgctttcgctggagcgcgacgatgatcggcctgtcgcttgcggtattcggaatcttgcacgcc
ctcgctcaagccttcgtcactggtcccgccaccaaacgtttcggcgagaagcaggccattatcgc
cggcatggcggccgacgcgctgggctacgtcttgctggcgttcgcgacgcgaggctggatggcct
tccccattatgattcttctcgcttccggcggcatcgggatgcccgcgttgcaggccatgctgtcc
aggcaggtagatgacgaccatcagggacagcttcaaggatcgctcgcggctcttaccagcctaac
ttcgatcactggaccgctgatcgtcacggcgatttatgccgcctcggcgagcacatggaacgggt
tggcatggattgtaggcgccgccctatacctttgtctgcctccccgcgttgcgtcgcggtcatgg
agccgggccacctcgacctga (SEQ ID NO: 28)

J-Tet sequence (Nucleotide sequence encoding same protein as above)
atgaaatctaacaatgcATtAatcgtcatTTtAggTacTgtTacTTtAgatgcAgtTggTatTgg
TttAgttatgccAgtTTtAccAggTctGttAcgTgatatTgtTcattcTgaTTCTatTgcATCtc
aTtatggTgtTctgTtagcATtatatgcATtAatgcaattTTtatgTgcaccAgttTtAggTgca
TtAtccgaTcgctttggTcgTcgTccagtTctgTtAgcttcTTtacttggTgcAactatTgaTta
TgcAatTatggcAacTacTccAgtTTtAtggatTTtAtaTgcAggTcgTatTgtTgcAggTatTa
cTggTgcAacaggtgcAgttgctggTgcAtatatTgcAgaTatTacAgatggTgaagatcgTgcA
cgTcaTttTggTTtAatgTCTgcttgtttTggTgtTggtatggtTgcaggTccAgtTgcAggTgg
TctgttAggTgcAatTtcTttAcatgcaccattTTtAgcAgcAgcAgtTTtAaaTggTTtAaaTT
tactGTtAggTtgTttTTtaatgcaAgaAtcTcataaAggagaAcgtcgaccAatgccAttACgT
gcAttTaaTccagtTTCTtcTttTcgTtgggcAcgTggTatgactatTgtTgcAgcaTtAatgac
tgtTttTtttatcatgcaaTtAgtTggTcaAgtTccAgcagcATtAtgggtcattttTggTgaAg
aTcgTtttcgTtggTCTgcAacTatgatTggTTtAtcTTtAgcAgtTttTggaatTttgcaTgcA
TtAgcAcaagcAttTgtTactggtccAgcAacTaaacgtttTggTgaAaaAcaAgcAattatcgc
AggTatggcAgcAgaTgcATtAggTtaTgtTtttgTtAgcAttTgcAacTcgTggTtggatggcAt
tTccAattatgattTtActTgcttcTggTggTatTggTatgccAgcAttAcaAgcAatgTtAtcT
agAcaAgtTgatgaTgaTcatcaAggTcaATtAcaaggatcTTtAgcAgctTtAacTTCTTtaac
ttcTatTactggTccATtAatTgtTacTgcAatttatgcAgcAtcTgcATCTacatggaaTggTt
tAgcatggattgtTggTgcAgcATtataTTtAgtTtgTTtAccAgcAttAcgtcgTggtgcatgg
TCTcgTgcAacTtcTacTtga (SEQ ID NO: 29)

```
                             SEQUENCE LISTING

<160> NUMBER OF SEQ ID NOS: 31

<210> SEQ ID NO 1
<211> LENGTH: 2204
<212> TYPE: DNA
<213> ORGANISM: Artificial sequence
<220> FEATURE:
<223> OTHER INFORMATION: Synthetic sequence

<400> SEQUENCE: 1
actagtctgc agtttttttt tttttttttt ttgtcgactc cggcgaacga ctatattatc    60
agcttacgat cccccgcgga gccttccgat tctttttttt tttttttttt ttccggctct   120
tactacctcg cctccgtagg cccgcggcta gtttctatcc tccaacgtaa attttttttt   180
tttttttttt ttcccgagcc gagctgtgac tcccgaaggc cggtctcctg tcacgtatcc   240
ggtggctgtg cgtttttttt tttttttttt ttcgtacacc accagccggg tcggcgagtc   300
tattgcatag ttttgcgagc gaatatgctt tgtttttttt tttttttttt ttcccttca    360 cggtgctggt atcatgccgc ggcgctccat ccacttctct cccttgctta tctttttttt   420
tttttttttt ttgcgcctac catccctata cagacgtcgg agttcgtttc tcgaaactgt   480
ctttccgaca gcttttttt tttttttttt ttcggattcc accgggcgca gcgttcctct   540
cgagcggcgg tagcacgtct tacagacagt tcttttttt tttttttttt ttccggcttc   600
gagttgaaca ttctgcatct taaccttcat ttattccatt ctcgcgagcc gcttttttt   660 tttttttttt ttcgatctac tgagacagcg agcgttccat cgttctttct tctttctttc   720
gcggcgagac ccttttttt tttttttttt ttaccttccg ggcgccgcgc ggcgggttta   780
cttactactc gcggagttaa gcggccctgc cgtttttttt tttttttttt ttggcgcggc   840
tccaccgcgc ctcgacgtag ggtgtcttcc ggggggttt acatactatt cctttttttt   900
tttttttttt ttagcgttct tgttattttc ccgcggcggc tttagactat cggctgttcg   960
gccttcttct tctttttttt tttttttttt ttccttcgat cgccaggcag gagtctcaag  1020
ttctcgcgag tatctgcttt gtttttatt cattttttt tttttttttt ttaatacctc   1080
cgactagcca aatcttctc cgttgggtcc catcttatat tccagctcag agtttttttt  1140
tttttttttt ttccctcgca tcgcctgcgc tccctccgca gttttccttg cgggattcta  1200
ctcgataacc tgtttttttt tttttttttt ttcttgctta tccggaatcc gtagtacgtc  1260
cgcgcggtac tcgagcgtat ctgcccatcc tattttttt tttttttttt ttctatatct   1320
ttctgcgttc tagcgtcgac cccgcgcctc atttagacag ggcctggagt tattttttt   1380 tttttttttt ttgtcctggc tccagctggc cacgattta tatagcccct ctcctattct   1440
ggctccccgg gattttttt tttttttttt ttatgacgaa agcttgaatt cttctattcc   1500
cgccgcggga tgaggccggt ggcgtgattc atttttttt tttttttttt ttgcggacta   1560
tgccccgcgg tgccgggtcg gcgcgtcgcg attttttctc cgcgggccag gcttttttt   1620 tttttttttt ttggtggctc cctaaagttg ctccaggcgc ggtcgccaat gggagaactc   1680
taatcgctcc cgtttttttt tttttttttt ttcttcttct acgattcgct aagacacctg  1740
cgcaagggct taatcttccc agctgtttct agtttttttt tttttttttt ttgcggtttt  1800
```

```
cccccagacc cgcgcgggcg tcatgtatgc tcgacgggtt ccttcccgcg tgttttttttt    1860 tttttttttt ttatgttttc cacgcgtgat tttctgggct gaggccacgc tctactacac    1920
cagtcaatta tgtttttttt tttttttttt ttagttactc cccactcaac tttccatgcg    1980
gcttttacgc ccgcggctat aagcgtcaag tttttttttt tttttttttt ttctatcatt    2040
ttatagcgga ctatacgcct gtaaacttcg agaccggatc ctggtccgaa agttttttttt   2100 tttttttttt ttaaagatta tttatctctt tacactatcg ccccggttgc tttgtactcc    2160
agccattaaa cattttttttt tttttttttt ttctgcagac tagt                    2204
```

<210> SEQ ID NO 2
<211> LENGTH: 795
<212> TYPE: DNA
<213> ORGANISM: Escherichia coli

<400> SEQUENCE: 2

```
atgattgaac aagatggatt gcacgcaggt tctccggccg cttgggtgga gaggctattc     60
ggctatgact gggcacaaca gacaatcggc tgctctgatg ccgccgtgtt ccggctgtca    120
gcgcaggggc gcccggttct ttttgtcaag accgacctgt ccggtgccct gaatgaactg    180
caggacgagg cagcgcggct atcgtggctg gccacgacgg gcgttccttg cgcagctgtg    240
ctcgacgttg tcactgaagc gggaagggac tggctgctat tgggcgaagt gccggggcag    300
gatctcctgt catcccacct tgctcctgcc gagaaagtat ccatcatggc tgatgcaatg    360
cggcggctgc atacgcttga tccggctacc tgcccattcg accaccaagc gaaacatcgc    420
atcgagcgag cacgtactcg gatggaagcc ggtcttgtcg atcaggatga tctggacgaa    480
gagcatcagg ggctcgcgcc agccgaactg ttcgccaggc tcaaggcgcg catgcccgac    540
ggcgaggatc tcgtcgtgac ccatggcgat gcctgcttgc cgaatatcat ggtggaaaat    600
ggccgctttt ctggattcat cgactgtggc cggctgggtg tggcggaccg ctatcaggac    660
atagcgttgg ctacccgtga tattgctgaa gagcttggcg gcgaatgggc tgaccgcttc    720
ctcgtgcttt acggtatcgc cgctcccgat tcgcagcgca tcgccttcta tcgccttctt    780
gacgagttct tctga                                                    795
```

<210> SEQ ID NO 3
<211> LENGTH: 792
<212> TYPE: DNA
<213> ORGANISM: Artificial sequence
<220> FEATURE:
<223> OTHER INFORMATION: Synthetic sequence

<400> SEQUENCE: 3

```
atgattgaac aagatggttt acatgctggt agtccagctg cttgggttga acgtttattt     60
ggttatgatt gggctcaaca aaccattggt tgtagtgatg ctgctgtttt cgtttaagt    120 gctcaaggtc gtcccgtgtt atttgtgaaa actgatttaa gcggtgcttt aaatgaatta    180
caagatgaag ctgctcgctt gagttggtta gctactactg tgttccatg tgctgctgta    240 ttagatgttg ttactgaagc tggtcgtgat tggttattgt taggtgaagt tccaggtcaa    300
gatttattga gtagtcattt agctcccgct gaaaaagtga gtattatggc tgatgctatg    360
cgtcgcttac atactttaga tccagctact tgtcccttttg atcatcaagc taaacatcgt    420
attgaacgtg ctcgtactcg tatggaagct ggtttagttg atcaagatga tttagatgaa    480
gaacatcaag gtttagcccc agctgaatta tttgctcgtt taaaagctcg tatgcccgat    540
ggtgaagatt tagttgttac tcatggtgat gcctgtttgc ccaatattat ggttgaaaat    600
```

| | | |
|---|---|---|
| ggtcgcttta gtggttttat tgattgtggt cgtttaggtg ttgctgatcg ctatcaagat | 660 | |
| attgctttag ctactcgcga tattgccgaa gaattaggtg aatgggctga tcgcttttta | 720 | |
| gtgttatatg gtattgctgc tccagatagt caacgcattg cttttatcg cttattagat | 780 | |
| gaattttttt aa | 792 | |

<210> SEQ ID NO 4
<211> LENGTH: 795
<212> TYPE: DNA
<213> ORGANISM: Artificial sequence
<220> FEATURE:
<223> OTHER INFORMATION: Synthetic sequence

<400> SEQUENCE: 4

| | |
|---|---|
| atgattgaac aagatggatt acatgcaggt tctccagcag cttgggttga acgtttgttt | 60 |
| ggatatgatt gggcacaaca aacaattggt tgttctgatg ctgctgtttt tcgtctttct | 120 |
| gctcaaggac gtcctgttct ttttgttaaa acagatcttt ctggtgcttt aaatgaatta | 180 |
| caagatgaag cagcacgttt atcttggtta gcaacaacag gagttcctt g tgcagctgtt | 240 |
| ttagatgttg ttactgaagc aggacgtgat tggttattat taggagaagt tcctggacaa | 300 |
| gatttacttt catctcatct tgctcctgca gaaaaagtat caattatggc tgatgcaatg | 360 |
| cggcgtttac atacacttga tccagctact tgtccatttg atcatcaagc aaaacatcgt | 420 |
| attgaacgtg cacgtactcg tatggaagca ggtcttgttg atcaagatga tttagatgaa | 480 |
| gagcatcaag gattagcacc agctgaatta ttcgctcgtt taaaagcacg tatgcctgat | 540 |
| ggtgaagatt tagtagttac acatggagat gcttgtttac aaatatattat ggtagaaaat | 600 |
| ggacgttttt ctggttttat cgattgtgga cgtttaggtg tagcagatcg ttatcaagat | 660 |
| attgctttag ctacacgtga tattgctgaa gaattaggag gagaatgggc tgatcgtttt | 720 |
| ttagtattat atggtattgc agctccagat tcacaacgta ttgcttttta tcgtcttta | 780 |
| gatgaatttt tctga | 795 |

<210> SEQ ID NO 5
<211> LENGTH: 795
<212> TYPE: DNA
<213> ORGANISM: Artificial sequence
<220> FEATURE:
<223> OTHER INFORMATION: Synthetic sequence

<400> SEQUENCE: 5

| | |
|---|---|
| atgattgagc aggatggtct tcatgctggt tctcctgctg cttgggttga gcgccttttt | 60 |
| ggttatgatt gggctcagca gactattggt tgttctgatg ctgctgtttt tcgcctttct | 120 |
| gctcagggtc gccctgttct ttttgttaag actgatcttt ctggtgcttt gaatgagctt | 180 |
| caggatgagg ctgctcgcct ttcttggctt gctactactg gtgttccttg tgctgctgtt | 240 |
| cttgatgttg ttactgaggc tggtcgcgat tggcttcttt gggtgaggt tcctggtcag | 300 |
| gatctttttgt cttctcatct tgctcctgct gagaaggttt ctattatggc tgatgctatg | 360 |
| cgccgccttc atactcttga tcctgctact tgtcctttg atcatcaggc taagcatcgc | 420 |
| attgagcgcg ctcgtactcg catggaggct ggtcttgttg atcaggatga tcttgatgag | 480 |
| gagcatcagg gtcttgctcc tgctgagctt tttgctcgcc ttaaggctcg catgcctgat | 540 |
| ggtgaggatc ttgttgttac tcatggtgat gcttgccttc ctaatattat ggttgagaat | 600 |
| ggtcgctttt ctggttttat tgattgtggt cgccttggtg ttgctgatcg ctatcaggat | 660 |
| attgctttgg ctactcgcga tattgctgag gagcttggtg gtgagtgggc tgatcgcttt | 720 |

```
ttggttctttatggtattgctgctcctgattctcagcgcattgcttttatcgccttttg      780 gatgagttttttttga                                                  795
```

<210> SEQ ID NO 6
<211> LENGTH: 12
<212> TYPE: DNA
<213> ORGANISM: Artificial sequence
<220> FEATURE:
<223> OTHER INFORMATION: Synthetic sequence

<400> SEQUENCE: 6

```
tagctagcta gc                                                     12
```

<210> SEQ ID NO 7
<211> LENGTH: 12
<212> TYPE: DNA
<213> ORGANISM: Artificial sequence
<220> FEATURE:
<223> OTHER INFORMATION: Synthetic sequence

<400> SEQUENCE: 7

```
tagctagcta gc                                                     12
```

<210> SEQ ID NO 8
<211> LENGTH: 12
<212> TYPE: DNA
<213> ORGANISM: Artificial sequence
<220> FEATURE:
<223> OTHER INFORMATION: Synthetic sequence

<400> SEQUENCE: 8

```
tagctagcta gc                                                     12
```

<210> SEQ ID NO 9
<211> LENGTH: 12
<212> TYPE: DNA
<213> ORGANISM: Artificial sequence
<220> FEATURE:
<223> OTHER INFORMATION: Synthetic sequence

<400> SEQUENCE: 9

```
tagctagcta gc                                                     12
```

<210> SEQ ID NO 10
<211> LENGTH: 12
<212> TYPE: DNA
<213> ORGANISM: Artificial sequence
<220> FEATURE:
<223> OTHER INFORMATION: Synthetic sequence

<400> SEQUENCE: 10

```
tagctagcta gc                                                     12
```

<210> SEQ ID NO 11
<211> LENGTH: 861
<212> TYPE: DNA
<213> ORGANISM: Bacillus subtilis

<400> SEQUENCE: 11

```
atgagtattc aacatttccg tgtcgccctt attcccttttt tgcggcatt ttgccttcct    60 gttttttgctc acccagaaac gctggtgaaa gtaaaagatg ctgaagatca gttgggtgca   120
cgagtgggtt acatcgaact ggatctcaac agcggtaaga tccttgagag ttttcgcccc   180
gaagaacgtt ttccaatgat gagcactttt aaagttctgc tatgtggcgc ggtattatcc   240
```

```
cgtattgacg ccgggcaaga gcaactcggt cgccgcatac actattctca gaatgacttg    300
gttgagtact caccagtcac agaaaagcat cttacggatg gcatgacagt aagagaatta    360
tgcagtgctg ccataaccat gagtgataac actgcggcca acttacttct gacaacgatc    420
ggaggaccga aggagctaac cgcttttttg cacaacatgg gggatcatgt aactcgcctt    480
gatcgttggg aaccggagct gaatgaagcc ataccaaacg acgagcgtga caccacgatg    540
cctgtagcaa tggcaacaac gttgcgcaaa ctattaactg gcgaactact tactctagct    600
tcccggcaac aattaataga ctggatggag gcggataaag ttgcaggacc acttctgcgc    660
tcggcccttc cggctggctg gtttattgct gataaatctg gagccggtga gcgtgggtct    720
cgcggtatca ttgcagcact ggggccagat ggtaagccct cccgtatcgt agttatctac    780
acgacgggga gtcaggcaac tatggatgaa cgaaatagac agatcgctga gataggtgcc    840
tcactgatta agcattggta a                                              861

<210> SEQ ID NO 12
<211> LENGTH: 861
<212> TYPE: DNA
<213> ORGANISM: Artificial sequence
<220> FEATURE:
<223> OTHER INFORMATION: Synthetic sequence

<400> SEQUENCE: 12
atgagtattc aacattttcg cgtggcctta attcccttttt ttgctgcttt ttgtttaccc     60 gttttttgctc atcccgaaac cttagtgaaa gtgaaagatg ccgaagatca attaggtgct    120
cgtgtgggtt atattgaatt agatttgaac agtggtaaaa tcttagaaag ttttcgccct    180
gaagaacgct ttccaatgat gagtactttt aaagtgttat tgtgtggtgc cgttttaagt    240
cgtgttgatg ctggtcaaga acaattaggt cgtcgcattc actacagcca aaatgattta    300
gttgaataca gtccagttac tgaaaaacat ttaactgatg gtatgaccgt gcgcgaatta    360
tgtagtgctg ctattactat gagtgataat accgctgcca atttgttgtt gactactatt    420
ggtggcccca agaattaaac cgccttttta cataatatgg gtgatcatgt gactcgctta    480
gatcgttggg aaccagaatt aaatgaagcc attccaaatg atgaacgcga tactactatg    540
ccagctgcta tggctactac tttacgcaaa ttattgactg gtgaattgtt gaccttagcc    600
agtcgccaac aattaattga ttggatggaa gctgataaag tggctggccc attattacgt    660
agtgctttac cagctggttg gtttattgct gataaaagtg gtgctggtga acgtggtagt    720
cgtggtatta ttgctgcttt aggcccagat ggtaaaccaa gtcgtattgt ggtgatttat    780
accactggta gtcaagctac tatggatgaa cgtaatcgtc aaattgctga aattggtgct    840
agtttgatta aacattggta a                                              861

<210> SEQ ID NO 13
<211> LENGTH: 861
<212> TYPE: DNA
<213> ORGANISM: Artificial sequence
<220> FEATURE:
<223> OTHER INFORMATION: Synthetic sequence

<400> SEQUENCE: 13
atgagtattc aacattttcg tgttgcttta attccttttt ttgctgcttt ttgtttacct     60 gttttttgctc atccagaaac attagttaaa gttaaagatg ctgaagatca attaggtgca    120
cgagttggtt atattgaatt agatttaaat agtggtaaaa ttttagaaag ttttcgtcct    180
gaagaacgtt ttccaatgat gagtactttt aaagtttttac tatgtggtgc tgttttatct    240
```

```
cgtattgatg ctggtcaaga acaattaggt cgtcgtattc actattctca aaatgattta    300
gttgaatatt ctccagttac agaaaaacat ttaacagatg gaatgacagt aagagaatta    360
tgtagtgctg ctattacaat gagtgataat actgctgcta atttactttt aacaacaatt    420
ggaggaccaa aagaattaac agctttttta cataatatgg gtgatcatgt tactcgttta    480
gatcgttggg aaccagaatt aaatgaagca attccaaatg atgaacgtga tacaacaatg    540
cctgttgcaa tggcaacaac attacgtaaa ctattaactg gtgaattact tactttagct    600
tctcgtcaac aattaattga ttggatggaa gcagataaag ttgcaggacc attacttcgt    660
tctgctttac ctgctggttg gtttatcgct gataaatctg gagcaggtga acgtggttct    720
cgtggtatca ttgcagcatt aggtccagat ggtaaacctt ctcgtattgt tgttatctat    780
acaacaggaa gtcaagcaac tatggatgaa cgaaatcgtc aaattgctga aattggtgct    840
tcattaatta aacattggta a                                              861

<210> SEQ ID NO 14
<211> LENGTH: 12
<212> TYPE: DNA
<213> ORGANISM: Artificial sequence
<220> FEATURE:
<223> OTHER INFORMATION: Synthetic sequence

<400> SEQUENCE: 14
tagctagcta gc                                                        12

<210> SEQ ID NO 15
<211> LENGTH: 12
<212> TYPE: DNA
<213> ORGANISM: Artificial sequence
<220> FEATURE:
<223> OTHER INFORMATION: Synthetic sequence

<400> SEQUENCE: 15
tagctagcta gc                                                        12

<210> SEQ ID NO 16
<211> LENGTH: 12
<212> TYPE: DNA
<213> ORGANISM: Artificial sequence
<220> FEATURE:
<223> OTHER INFORMATION: Synthetic sequence

<400> SEQUENCE: 16
tagctagcta gc                                                        12

<210> SEQ ID NO 17
<211> LENGTH: 16
<212> TYPE: DNA
<213> ORGANISM: Artificial sequence
<220> FEATURE:
<223> OTHER INFORMATION: Synthetic sequence

<400> SEQUENCE: 17 ttttttteee tttttt                                                    16

<210> SEQ ID NO 18
<211> LENGTH: 16
<212> TYPE: DNA
<213> ORGANISM: Artificial sequence
<220> FEATURE:
<223> OTHER INFORMATION: Synthetic sequence
```

<400> SEQUENCE: 18
aaaaaaggga aaaaaa                                                        16

<210> SEQ ID NO 19
<211> LENGTH: 12
<212> TYPE: DNA
<213> ORGANISM: Artificial sequence
<220> FEATURE:
<223> OTHER INFORMATION: Synthetic sequence

<400> SEQUENCE: 19
tagctagcta gc                                                            12

<210> SEQ ID NO 20
<211> LENGTH: 264
<212> TYPE: PRT
<213> ORGANISM: Escherichia coli

<400> SEQUENCE: 20

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
        50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
        130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

```
<210> SEQ ID NO 21
<211> LENGTH: 263
<212> TYPE: PRT
<213> ORGANISM: Artificial sequence
<220> FEATURE:
<223> OTHER INFORMATION: Synthetic sequence

<400> SEQUENCE: 21

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45

Val Lys Thr Asp Leu Ser Gly Ala Leu Asn Glu Leu Gln Asp Glu Ala
    50                  55                  60

Ala Arg Leu Ser Trp Leu Ala Thr Thr Gly Val Pro Cys Ala Ala Val
65                  70                  75                  80

Leu Asp Val Val Thr Glu Ala Gly Arg Asp Trp Leu Leu Leu Gly Glu
                85                  90                  95

Val Pro Gly Gln Asp Leu Leu Ser Ser His Leu Ala Pro Ala Glu Lys
            100                 105                 110

Val Ser Ile Met Ala Asp Ala Met Arg Arg Leu His Thr Leu Asp Pro
        115                 120                 125

Ala Thr Cys Pro Phe Asp His Gln Ala Lys His Arg Ile Glu Arg Ala
    130                 135                 140

Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Glu Trp Ala Asp Arg Phe Leu
225                 230                 235                 240

Val Leu Tyr Gly Ile Ala Ala Pro Asp Ser Gln Arg Ile Ala Phe Tyr
                245                 250                 255

Arg Leu Leu Asp Glu Phe Phe
            260

<210> SEQ ID NO 22
<211> LENGTH: 264
<212> TYPE: PRT
<213> ORGANISM: Artificial sequence
<220> FEATURE:
<223> OTHER INFORMATION: Synthetic sequence

<400> SEQUENCE: 22

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
            20                  25                  30

Asp Ala Ala Val Phe Arg Leu Ser Ala Gln Gly Arg Pro Val Leu Phe
        35                  40                  45
```

Val Lys Thr Asp Leu Ser Gly Ala Leu Asn Glu Leu Gln Asp Glu Ala
 50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
130                 135                 140

Arg Thr Arg Met Glu Ala Gly Leu Val Asp Gln Asp Leu Asp Glu
145                 150                 155                 160

Glu His Gln Gly Leu Ala Pro Ala Glu Leu Phe Ala Arg Leu Lys Ala
                165                 170                 175

Arg Met Pro Asp Gly Glu Asp Leu Val Val Thr His Gly Asp Ala Cys
            180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
210                 215                 220

Thr Arg Asp Ile Ala Glu Leu Gly Gly Glu Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260

<210> SEQ ID NO 23
<211> LENGTH: 264
<212> TYPE: PRT
<213> ORGANISM: Artificial sequence
<220> FEATURE:
<223> OTHER INFORMATION: Synthetic sequence

<400> SEQUENCE: 23

Met Ile Glu Gln Asp Gly Leu His Ala Gly Ser Pro Ala Ala Trp Val
1               5                   10                  15

Glu Arg Leu Phe Gly Tyr Asp Trp Ala Gln Gln Thr Ile Gly Cys Ser
                20                  25                  30

Asp Ala Ala Val Phe Arg Leu Ser Ala Gln Gly Arg Pro Val Leu Phe
            35                  40                  45

Val Lys Thr Asp Leu Ser Gly Ala Leu Asn Glu Leu Gln Asp Glu Ala
 50                  55                  60

Ala Arg Leu Ser Trp Leu Ala Thr Thr Gly Val Pro Cys Ala Ala Val
 65                  70                  75                  80

Leu Asp Val Val Thr Glu Ala Gly Arg Asp Trp Leu Leu Gly Glu
                 85                  90                  95

Val Pro Gly Gln Asp Leu Leu Ser Ser His Leu Ala Pro Ala Glu Lys
                100                 105                 110

Val Ser Ile Met Ala Asp Ala Met Arg Arg Leu His Thr Leu Asp Pro
            115                 120                 125

Ala Thr Cys Pro Phe Asp His Gln Ala Lys His Arg Ile Glu Arg Ala
130                 135                 140

```
Arg Thr Arg Met Glu Ala Gly Leu Val Asp Gln Asp Asp Leu Asp Glu
145                 150                 155                 160

Glu His Gln Gly Leu Ala Pro Ala Glu Leu Phe Ala Arg Leu Lys Ala
            165                 170                 175

Arg Met Pro Asp Gly Glu Asp Leu Val Val Thr His Gly Asp Ala Cys
                180                 185                 190

Leu Pro Asn Ile Met Val Glu Asn Gly Arg Phe Ser Gly Phe Ile Asp
        195                 200                 205

Cys Gly Arg Leu Gly Val Ala Asp Arg Tyr Gln Asp Ile Ala Leu Ala
    210                 215                 220

Thr Arg Asp Ile Ala Glu Glu Leu Gly Gly Trp Ala Asp Arg Phe
225                 230                 235                 240

Leu Val Leu Tyr Gly Ile Ala Ala Pro Asp Ser Gln Arg Ile Ala Phe
                245                 250                 255

Tyr Arg Leu Leu Asp Glu Phe Phe
            260
```

```
<210> SEQ ID NO 24
<211> LENGTH: 5
<212> TYPE: PRT
<213> ORGANISM: Artificial sequence
<220> FEATURE:
<223> OTHER INFORMATION: Synthetic sequence

<400> SEQUENCE: 24

Ala Ala Ala Ala Ala
1               5

<210> SEQ ID NO 25
<211> LENGTH: 286
<212> TYPE: PRT
<213> ORGANISM: Bacillus subtilis

<400> SEQUENCE: 25

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175
```

```
Asp Thr Thr Met Pro Val Ala Met Ala Thr Thr Leu Arg Lys Leu Leu
                180                 185                 190

Thr Gly Glu Leu Leu Thr Leu Ala Ser Arg Gln Gln Leu Ile Asp Trp
            195                 200                 205

Met Glu Ala Asp Lys Val Ala Gly Pro Leu Leu Arg Ser Ala Leu Pro
        210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 26
<211> LENGTH: 286
<212> TYPE: PRT
<213> ORGANISM: Artificial sequence
<220> FEATURE:
<223> OTHER INFORMATION: Synthetic sequence

<400> SEQUENCE: 26

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Val Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Ala Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255
```

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 27
<211> LENGTH: 286
<212> TYPE: PRT
<213> ORGANISM: Artificial sequence
<220> FEATURE:
<223> OTHER INFORMATION: Synthetic sequence

<400> SEQUENCE: 27

Met Ser Ile Gln His Phe Arg Val Ala Leu Ile Pro Phe Phe Ala Ala
1               5                   10                  15

Phe Cys Leu Pro Val Phe Ala His Pro Glu Thr Leu Val Lys Val Lys
            20                  25                  30

Asp Ala Glu Asp Gln Leu Gly Ala Arg Val Gly Tyr Ile Glu Leu Asp
        35                  40                  45

Leu Asn Ser Gly Lys Ile Leu Glu Ser Phe Arg Pro Glu Glu Arg Phe
    50                  55                  60

Pro Met Met Ser Thr Phe Lys Val Leu Leu Cys Gly Ala Val Leu Ser
65                  70                  75                  80

Arg Ile Asp Ala Gly Gln Glu Gln Leu Gly Arg Arg Ile His Tyr Ser
                85                  90                  95

Gln Asn Asp Leu Val Glu Tyr Ser Pro Val Thr Glu Lys His Leu Thr
            100                 105                 110

Asp Gly Met Thr Val Arg Glu Leu Cys Ser Ala Ala Ile Thr Met Ser
        115                 120                 125

Asp Asn Thr Ala Ala Asn Leu Leu Leu Thr Thr Ile Gly Gly Pro Lys
    130                 135                 140

Glu Leu Thr Ala Phe Leu His Asn Met Gly Asp His Val Thr Arg Leu
145                 150                 155                 160

Asp Arg Trp Glu Pro Glu Leu Asn Glu Ala Ile Pro Asn Asp Glu Arg
                165                 170                 175

Asp Thr Thr Met Pro Val Ala Met Ala Thr Thr Leu Arg Lys Leu Leu
            180                 185                 190

Thr Gly Glu Leu Leu Thr Leu Ala Ser Arg Gln Gln Leu Ile Asp Trp
        195                 200                 205

Met Glu Ala Asp Lys Val Ala Gly Pro Leu Leu Arg Ser Ala Leu Pro
    210                 215                 220

Ala Gly Trp Phe Ile Ala Asp Lys Ser Gly Ala Gly Glu Arg Gly Ser
225                 230                 235                 240

Arg Gly Ile Ile Ala Ala Leu Gly Pro Asp Gly Lys Pro Ser Arg Ile
                245                 250                 255

Val Val Ile Tyr Thr Thr Gly Ser Gln Ala Thr Met Asp Glu Arg Asn
            260                 265                 270

Arg Gln Ile Ala Glu Ile Gly Ala Ser Leu Ile Lys His Trp
        275                 280                 285

<210> SEQ ID NO 28
<211> LENGTH: 1191
<212> TYPE: DNA
<213> ORGANISM: Francisella tularensi

<400> SEQUENCE: 28

```
atgaaatcta acaatgcgct catcgtcatc ctcggcaccg tcaccctgga tgctgtaggc    60
ataggcttgg ttatgccggt actgccgggc tcttgcggg atatcgtcca ttccgacagc   120
atcgccagtc actatggcgt gctgctagcg ctatatgcgt tgatgcaatt tctatgcgca   180
cccgttctcg gagcactgtc cgaccgcttt ggccgccgcc cagtcctgct cgcttcgcta   240
cttggagcca ctatcgacta cgcgatcatg gcgaccacac ccgtcctgtg gatcctctac   300
gccggacgca tcgtggccgg catcaccggc gccacaggtg cggttgctgg cgcctatatc   360
gccgacatca ccgatgggga agatcgggct cgccacttcg ggctcatgag cgcttgtttc   420
ggcgtgggta tggtggcagg ccccgtggcc ggggactgt tgggcgccat ctccttgcat   480
gcaccattcc ttgcggcggc ggtgctcaac ggcctcaacc tactactggg ctgcttccta   540
atgcaggagt cgcataaggg agagcgtcga ccgatgccct tgagagcctt caacccagtc   600
agctccttcc ggtgggcgcg ggcatgact atcgtcgccg cacttatgac tgtcttcttt   660
atcatgcaac tcgtaggaca ggtgccggca gcgctctggg tcattttcgg cgaggaccgc   720
tttcgctgga gcgcgacgat gatcggcctg tcgcttgcgg tattcggaat cttgcacgcc   780
ctcgctcaag ccttcgtcac tggtcccgcc accaaacgtt tcggcgagaa gcaggccatt   840
atcgccggca tggcggccga cgcgctgggc tacgtcttgc tggcgttcgc gacgcgaggc   900
tggatggcct tccccattat gattcttctc gcttccggcg catcgggat gcccgcgttg   960
caggccatgc tgtccaggca ggtagatgac gaccatcagg acagcttca aggatcgctc  1020
gcggctctta ccagcctaac ttcgatcact ggaccgctga tcgtcacggc gatttatgcc  1080
gcctcggcga gcacatggaa cgggttggca tggattgtag gcgccgccct ataccttgtc  1140
tgcctccccg cgttgcgtcg cggtgcatgg agccgggcca cctcgacctg a           1191
```

<210> SEQ ID NO 29
<211> LENGTH: 1191
<212> TYPE: DNA
<213> ORGANISM: Artificial Sequence
<220> FEATURE:
<223> OTHER INFORMATION: synthetic sequence

<400> SEQUENCE: 29

```
atgaaatcta acaatgcatt aatcgtcatt ttaggtactg ttactttaga tgcagttggt    60
attggtttag ttatgccagt tttaccaggt ctgttacgtg atattgttca ttctgattct   120
attgcatctc attatggtgt tctgttagca ttatatgcat taatgcaatt tttatgtgca   180
ccagttttag gtgcattatc cgatcgcttt ggtcgtcgtc cagttctgtt agcttcttta   240
cttggtgcaa ctattgatta tgcaattatg gcaactactc cagttttatg gattttatat   300
gcaggtcgta ttgttgcagg tattactggt gcaacaggtg cagttgctgg tgcatatatt   360
gcagatatta cagatggtga agatcgtgca cgtcattttg gtttaatgtc tgcttgtttt   420
ggtgttggta tggttgcagg tccagttgca ggtggtctgt taggtgcaat ttcttttacat   480
gcaccatttt tagcagcagc agttttaaat ggtttaaatt tactgttagg ttgtttttta   540
atgcaagaat ctcataaagg agaacgtcga ccaatgccat tacgtgcatt taatccagtt   600
tcttcttttc gttgggcacg tggtatgact attgttgcag cattaatgac tgttttttt   660
atcatgcaat tagttggtca agttccagca gcattatggg tcattttggg tgaagatcgt   720
tttcgttggt ctgcaactat gattggttta tctttagcag ttttggaat tttgcatgca   780
ttagcacaag catttgttac tggtccagca actaaacgtt ttggtgaaaa acaagcaatt   840
```

```
atcgcaggta tggcagcaga tgcattaggt tatgttttgt tagcatttgc aactcgtggt    900
tggatggcat ttccaattat gattttactt gcttctggtg gtattggtat gccagcatta    960
caagcaatgt tatctagaca agttgatgat gatcatcaag gtcaattaca aggatcttta   1020
gcagctttaa cttctttaac ttctattact ggtccattaa ttgttactgc aatttatgca   1080
gcatctgcat ctacatggaa tggtttagca tggattgttg gtgcagcatt atatttagtt   1140
tgtttaccag cattacgtcg tggtgcatgg tctcgtgcaa cttctacttg a            1191
```

<210> SEQ ID NO 30
<211> LENGTH: 396
<212> TYPE: PRT
<213> ORGANISM: Francisella tularensi

<400> SEQUENCE: 30

```
Met Lys Ser Asn Asn Ala Leu Ile Val Ile Leu Gly Thr Val Thr Leu
 1               5                  10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
            100                 105                 110

Gly Ala Val Ala Gly Ala Tyr Ile Ala Asp Ile Thr Asp Gly Glu Asp
        115                 120                 125

Arg Ala Arg His Phe Gly Leu Met Ser Ala Cys Phe Gly Val Gly Met
    130                 135                 140

Val Ala Gly Pro Val Ala Gly Leu Leu Gly Ala Ile Ser Leu His
145                 150                 155                 160

Ala Pro Phe Leu Ala Ala Val Leu Asn Gly Leu Asn Leu Leu Leu
                165                 170                 175

Gly Cys Phe Leu Met Gln Glu Ser His Lys Gly Glu Arg Arg Pro Met
            180                 185                 190

Pro Leu Arg Ala Phe Asn Pro Val Ser Ser Phe Arg Trp Ala Arg Gly
        195                 200                 205

Met Thr Ile Val Ala Ala Leu Met Thr Val Phe Phe Ile Met Gln Leu
    210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
            260                 265                 270

Arg Phe Gly Glu Lys Gln Ala Ile Ile Ala Gly Met Ala Ala Asp Ala
        275                 280                 285

Leu Gly Tyr Val Leu Leu Ala Phe Ala Thr Arg Gly Trp Met Ala Phe
    290                 295                 300

Pro Ile Met Ile Leu Leu Ala Ser Gly Gly Ile Gly Met Pro Ala Leu
305                 310                 315                 320
```

```
Gln Ala Met Leu Ser Arg Gln Val Asp Asp His Gln Gly Gln Leu
                325                 330                 335

Gln Gly Ser Leu Ala Ala Leu Thr Ser Leu Thr Ser Ile Thr Gly Pro
            340                 345                 350

Leu Ile Val Thr Ala Ile Tyr Ala Ala Ser Ala Ser Thr Trp Asn Gly
            355                 360                 365

Leu Ala Trp Ile Val Gly Ala Ala Leu Tyr Leu Val Cys Leu Pro Ala
            370                 375                 380

Leu Arg Arg Gly Ala Trp Ser Arg Ala Thr Ser Thr
385                 390                 395

<210> SEQ ID NO 31
<211> LENGTH: 396
<212> TYPE: PRT
<213> ORGANISM: Artificial Sequence
<220> FEATURE:
<223> OTHER INFORMATION: synthetic sequence

<400> SEQUENCE: 31

Met Lys Ser Asn Asn Ala Leu Ile Val Ile Leu Gly Thr Val Thr Leu
1               5                   10                  15

Asp Ala Val Gly Ile Gly Leu Val Met Pro Val Leu Pro Gly Leu Leu
            20                  25                  30

Arg Asp Ile Val His Ser Asp Ser Ile Ala Ser His Tyr Gly Val Leu
        35                  40                  45

Leu Ala Leu Tyr Ala Leu Met Gln Phe Leu Cys Ala Pro Val Leu Gly
    50                  55                  60

Ala Leu Ser Asp Arg Phe Gly Arg Arg Pro Val Leu Leu Ala Ser Leu
65                  70                  75                  80

Leu Gly Ala Thr Ile Asp Tyr Ala Ile Met Ala Thr Thr Pro Val Leu
                85                  90                  95

Trp Ile Leu Tyr Ala Gly Arg Ile Val Ala Gly Ile Thr Gly Ala Thr
            100                 105                 110

Gly Ala Val Ala Gly Ala Tyr Ile Ala Asp Ile Thr Asp Gly Glu Asp
        115                 120                 125

Arg Ala Arg His Phe Gly Leu Met Ser Ala Cys Phe Gly Val Gly Met
    130                 135                 140

Val Ala Gly Pro Val Ala Gly Leu Leu Gly Ala Ile Ser Leu His
145                 150                 155                 160

Ala Pro Phe Leu Ala Ala Val Leu Asn Gly Leu Asn Leu Leu Leu
                165                 170                 175

Gly Cys Phe Leu Met Gln Glu Ser His Lys Gly Glu Arg Arg Pro Met
            180                 185                 190

Pro Leu Arg Ala Phe Asn Pro Val Ser Ser Phe Arg Trp Ala Arg Gly
        195                 200                 205

Met Thr Ile Val Ala Ala Leu Met Thr Val Phe Phe Ile Met Gln Leu
    210                 215                 220

Val Gly Gln Val Pro Ala Ala Leu Trp Val Ile Phe Gly Glu Asp Arg
225                 230                 235                 240

Phe Arg Trp Ser Ala Thr Met Ile Gly Leu Ser Leu Ala Val Phe Gly
                245                 250                 255

Ile Leu His Ala Leu Ala Gln Ala Phe Val Thr Gly Pro Ala Thr Lys
            260                 265                 270

Arg Phe Gly Glu Lys Gln Ala Ile Ile Ala Gly Met Ala Ala Asp Ala
        275                 280                 285
```

```
Leu Gly Tyr Val Leu Leu Ala Phe Ala Thr Arg Gly Trp Met Ala Phe
    290                 295                 300

Pro Ile Met Ile Leu Leu Ala Ser Gly Gly Ile Gly Met Pro Ala Leu
305                 310                 315                 320

Gln Ala Met Leu Ser Arg Gln Val Asp Asp Asp His Gln Gly Gln Leu
                325                 330                 335

Gln Gly Ser Leu Ala Ala Leu Thr Ser Leu Thr Ser Ile Thr Gly Pro
            340                 345                 350

Leu Ile Val Thr Ala Ile Tyr Ala Ala Ser Ala Ser Thr Trp Asn Gly
        355                 360                 365

Leu Ala Trp Ile Val Gly Ala Ala Leu Tyr Leu Val Cys Leu Pro Ala
    370                 375                 380

Leu Arg Arg Gly Ala Trp Ser Arg Ala Thr Ser Thr
385                 390                 395
```

NON-SILENCING SELECTABLE MARKER GENES AND METHODS OF USE

CROSS-REFERENCE

This application claims the benefit of U.S. Provisional Patent Application Nos. 62/116,197, filed Feb. 13, 2015, and 62/117,909, filed Feb. 18, 2015, which applications are incorporated herein by reference in their entirety.

FEDERALLY SPONSORED RESEARCH AND DEVELOPMENT

This invention was made with Government support under contract HL064274 awarded by the National Institutes of Health. The Government has certain rights in the invention.

INCORPORATION BY REFERENCE OF SEQUENCE LISTING PROVIDED AS A TEXT FILE

A Sequence Listing is provided herewith as a text file "STAN-1184 Seq List_ST25.txt" created on Jan. 28, 2016 and having a size of 41 KB. The contents of the text file are incorporated by reference herein in their entirety.

BACKGROUND

The introduction of an exogenous nucleic acid sequences (e.g., DNA) into cells plays a major role in a variety of biotechnology and related applications, including research, synthetic and therapeutic applications. Research applications include the production of transgenic cells and animals. Synthetic applications include the production of peptides and proteins, as well as therapeutic RNAs, such as RNAi reagents, Cas9 guide RNAs, or ribozymes. Therapeutic applications include gene therapy applications.

In many of these applications, it is desirable to introduce the exogenous DNA in a manner such that it provides for long-term transgene expression, i.e., long-term expression of the protein or RNA encoded by the exogenous DNA. Plasmid DNA based expression vectors have become an essential tool for both biological discovery and the development of new therapeutics. However, the inability to achieve sustained elevated levels of transgene expression in vivo have limited their usage. Standard plasmid vectors composed of (i) a transgene expression cassette (which expresses a transgene, e.g., in eukaryotic cells), and (ii) plasmid bacterial backbone (BB) sequences (which are generally thought of as non-transcribed spacer sequences in the context of transgene expression in eukaryotic cells), are able to express a high level of transgene product shortly after entering eukaryotic cells (e.g., mammalian cells), but the transgene product usually declines to very low or undetectable levels in a period of days even though vector DNA is still present.

To overcome plasmid DNA related transgene silencing in vivo, minicircle DNA vectors have been developed by removing the plasmid bacterial backbone (BB) from the plasmid vector (e.g., via homologous recombination). Minicircle DNA vectors persistently express transgenes at 10- to 1,000-fold levels compared to what can be obtained from a conventional plasmid in quiescent tissues in vivo. Because the plasmid BB, which contains the bacterial replication origin and a selectable marker, has been removed from a minicircle DNA vector, the conventional plasmid preparation method is not suitable for minicircle DNA preparation. Even robust methods that have been developed to produce minicircle DNA vectors are more complicated than conventional plasmid preparation, which limits the usage of minicircle DNA vectors.

Expression vectors that can provide for sustained elevated levels of transgene expression, and that can be produced using simple well-established methods are needed in the art. The present disclosure provides compositions and methods that address these issues.

SUMMARY

Compositions and methods are provided for achieving persistent, high level expression of transgenes in vitro, ex vivo, and/or in vivo. Aspects of the disclosure include nucleic acids and expression vectors having a non-silencing selectable marker gene, and methods of using the same. A subject expression vector includes an expression cassette and a non-silencing selectable marker gene. In some cases, the expression cassette includes an insertion site and/or a transgene operably linked to a promoter, e.g., a promoter functional in a eukaryotic cell.

A non-silencing selectable marker gene is a selectable marker gene that does not silence transgene expression from an expression vector, even when present on the same vector. In other words, an expression vector that includes an expression cassette that provides for persistent and high level expression of a transgene in a eukaryote (e.g., a mammal), can also include a selectable marker gene (i.e., no need to remove the selectable marker gene) if the selectable marker gene is a subject non-silencing selectable marker gene. It is the sequence of a subject non-silencing selectable marker gene (i.e., the sequence that encodes a selectable marker protein such as a drug selectable marker protein) that gives the marker gene the property of being "non-silencing." A "non-silencing selectable marker gene" has the property of being a "selectable marker gene" by virtue of its ability to provide for selection, i.e., for selective retention of cells (e.g., prokaryotic cells) that comprise the non-silencing selectable marker gene, during culturing and propagation in the cells. Thus, a "non-silencing selectable marker gene" is "non-silencing" and is a "selectable marker gene". Thus, for example, in some cases, a subject non-silencing selectable marker gene includes a nucleotide sequence encoding a drug selectable marker protein that provides drug resistance for prokaryotic cells.

In some embodiments, the non-silencing selectable marker gene provides for selection (e.g., provides drug resistance for prokaryotic cells), and includes a nucleotide sequence that (i) encodes a selectable marker protein (e.g., a drug selectable marker protein); (ii) is operably linked to a promoter functional in a desired cell type (e.g., prokaryotic cells), and (iii) includes an increased A/T content relative to a corresponding wild type nucleotide sequence. In some embodiments, the non-silencing selectable marker gene provides for selection (e.g., provides drug resistance for prokaryotic cells), and includes a nucleotide sequence that (i) encodes a selectable marker protein (e.g., a drug selectable marker protein); (ii) is operably linked to a promoter functional in a desired cell type (e.g., prokaryotic cells), and (iii) has an A/T content in a range of from 52% to 70%.

In some cases, the nucleotide sequence encodes a drug selectable marker protein that provides resistance for prokaryotic cells to one or more drugs selected from: kanamycin, neomycin, ampicillin, carbenicillin, chloramphenicol, gentamicin, tetracycline, rifampin, trimethoprim, hygromycin B, and spectinomycin.

In some cases, the nucleotide sequence encoding the drug selectable marker protein comprises an A/T content in a range of from 52% to 70%, or from 58% to 68%. In some cases, the A/T content of the nucleotide sequence encoding the drug selectable marker protein is 1.1 fold or more greater than the A/T content of the corresponding wild type nucleotide sequence. In some cases, the nucleotide sequence encoding the drug selectable marker protein comprises a T:A ratio in a range of from 0.8 to 2.0. In some cases, the nucleotide sequence encoding the drug selectable marker protein comprises a T:A ratio that is greater than the T:A ratio of the corresponding wild type nucleotide sequence by a range of from 1.1 fold to 1.3 fold. In some cases, the nucleotide sequence encoding the drug selectable marker protein comprises: (a) an increased number of Poly-A/Poly-T tracts relative to the number of Poly-A/Poly-T tracts present in the corresponding wild type nucleotide sequence and/or (b) one or more Poly-A/Poly-T tracts that are greater in length than a corresponding Poly-A/Poly-T tract present in the corresponding wild type nucleotide sequence. In some cases, the nucleotide sequence encoding the drug selectable marker protein comprises 10 or more Poly T tracts, each of which have 3 or more consecutive T nucleotides.

In some cases, the nucleotide sequence encoding the drug selectable marker protein comprises 2 or fewer instances of the following Polymerase II (Pol II) pause site: TTATT. In some cases, the nucleotide sequence encoding the drug selectable marker protein does not comprise any of the following Polymerase II (Pol II) pause sites: TTTATT, TTTTTTTCCCTTTTTT (SEQ ID NO: 17), and AAAAAAGGGAAAAAAA (SEQ ID NO: 18). In some cases, the nucleotide sequence encoding the drug selectable marker protein has a nucleotide sequence identity in a range of from 70% to 98% with the corresponding wild type nucleotide sequence.

In some cases, the drug selectable marker protein provides resistance for prokaryotic cells to kanamycin and the corresponding wild type nucleotide sequence is set forth in SEQ ID NO: 2. In some cases, the nucleotide sequence encoding the drug selectable marker protein has 87% or more nucleotide sequence identity with the sequence set forth in SEQ ID NO: 4. In some cases, the nucleotide sequence encoding the drug selectable marker protein comprises the nucleotide sequence set forth in any of SEQ ID NOs: 3 and 4. In some cases, the drug selectable marker protein provides resistance for prokaryotic cells to ampicillin and the corresponding wild type nucleotide sequence is set forth in SEQ ID NO: 11. In some cases, the nucleotide sequence encoding a drug selectable marker protein has 88% or more nucleotide sequence identity with the sequence set forth in SEQ ID NO: 13. In some cases, the nucleotide sequence encoding the drug selectable marker protein comprises the nucleotide sequence set forth in any of SEQ ID NOs: 12 and 13. In some cases, the drug selectable marker protein provides resistance for prokaryotic cells to tetracycline and the corresponding wild type nucleotide sequence is set forth in SEQ ID NO: 28. In some cases, the nucleotide sequence encoding a drug selectable marker protein has 73% or more nucleotide sequence identity with the sequence set forth in SEQ ID NO: 29. In some cases, the nucleotide sequence encoding the drug selectable marker protein comprises the nucleotide sequence set forth in SEQ ID NO: 29. In some cases, the drug selectable marker protein comprises an amino acid sequence having 85% or more sequence identity with the amino acid sequence of a corresponding wild type protein, and in some cases, the corresponding wild type protein comprises the amino acid sequence set forth in any one of SEQ ID NOs: 20 (Kan), 25 (Amp), and 30 (Tet). In some cases, the drug selectable marker protein comprises an amino acid sequence that is mutated relative to a corresponding wild type protein.

In some cases, the expression vector is circular. In some cases, the expression vector is a virus. In some cases, the transgene is operably linked to a promoter functional in one or more cells selected from: mammalian cells, rodent cells, primate cells, and human cells. In some cases, the transgene comprises a nucleotide sequence encoding an RNA selected from: a translated RNA, a non-coding RNA, an antisense RNA, a microRNA, an shRNA, and an siRNA.

These compositions and methods find use in many applications, including therapeutic applications such as in gene therapy; synthesis applications such as in the synthesis of peptides, proteins, and RNAs, e.g. for research or therapeutic purposes; and research applications, such as in the production of transgenic cells and animals. Aspects of the disclosure include methods of expressing a transgene in a eukaryotic cell, where such methods can include a step of introducing into a eukaryotic cell a subject expression vector. In some cases the eukaryotic cell is in culture in vitro. In some cases the eukaryotic cell is ex vivo. In some cases, the eukaryotic cell is in vivo. In some cases, the eukaryotic cell is a mammalian cell (e.g., a human cell). In some cases, a subject method includes administering to an individual a formulation comprising a subject expression vector. In some cases, the administering includes systemic administration. In some case, the individual is a mammal (e.g., a human). In some cases, a transgene of an expression cassette of the subject expression vector includes a nucleotide sequence encoding an RNA selected from: a translated RNA, a non-coding RNA, an antisense RNA, a microRNA, an shRNA, and an siRNA. In some cases, the transgene includes a nucleotide sequence encoding a protein.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

FIG. 1: Sequence of a 2.2 kb nucleosome exclusion sequence (NES). 20 bp of "T" were arranged in every 60 bp of random DNA (SEQ ID NO: 1).

(FIG. 3A) RD-containing vector (FIG. 3B) NES-containing vector.

FIGS. 4A-4C: Backbone transcripts were detected through RT-qPCR experiments. (FIG. 4A) The DNA structure of the infused vectors. Arrows indicates the RT primers used to detect short sense strand transcripts (SSS) and to detect short antisense strand transcripts (SAS). The qPCR signals were normalized to actin. (FIG. 4B) Results from panel A. RT-qPCR experiments. (FIG. 4C) A schematic representation of the transcription pattern from the backbone. Backbone transcription occurs from both sense and antisense strands of both NES and RD vectors, while the sense transcription is more dominant than the antisense transcription, and transcription from the NES backbone is greater than transcription from the RD backbone.

FIGS. 5A-5E: RSV-hAAT expression constructs and transgene expression in mice. (FIG. 5A) The 16 nucleotide sequence of Polymerase 2 (Pol 2) arrest site of histone H3.3. (FIG. 5B) Schematic of the hAAT expressing DNA construct infused into mice in the experiments shown in panel C. Vertical lines indicate the locations where Pol2 arrest sites in panel A were incorporated into the construct. The arrows indicate the direction of transcription that the Pol2 arrest site blocked. In this example, two copies of Pol2 arrest site were placed at 0.5 kb away from bpA (bpA polyA signal) and 1.7 kb away from bpA in the antisense orientation, respectively. "RSV" is Rous sarcoma virus (RSV) promoter. (FIG. 5C) Serum hAAT levels at various time points after equimolar infusion of the plasmid vectors through hydrodynamic tail vein injection in mice (n=4 mice per group). Error bars represent the standard deviation. This figure indicates that while NES sequence did not silence the transgene, the presence of two copies of Pol2 arrest sites on the antisense strand was able to silence the transgene. (FIG. 5D) Schematic of hAAT expressing DNA construct infused for animal experiments shown in panel E. Two copies of Pol2 arrest site were placed at 0.5 kb away from bpA (bpA polyA signal) and 1.7 kb away from bpA on the sense orientation, respectively. "RSV" is Rous sarcoma virus (RSV) promoter. (FIG. 5E) Serum hAAT levels at various time points after equimolar infusion of the plasmid vectors through hydrodynamic tail vein injection in mice (n=5 mice per group). Error bars represent the standard deviation. This figure indicates that while NES sequence did not silence the transgene, the presence of two copies of Pol2 arrest sites on the sense strand was able to silence transgene expression (reduce transgene expression).

FIG. 6: Top: Nucleotide sequence (SEQ ID NO: 2) encoding Kanamycin (Kan) resistance protein. Bottom: Nucleotide sequence (J-Kan) (SEQ ID NO: 4) encoding the same protein. Bold nucleotides of the bottom sequence (J-Kan) (SEQ ID NO: 4) are modified (mutated) relative to the top sequence (SEQ ID NO: 2).

FIG. 8: The depicted nucleotide sequence (JT-Kan) (SEQ ID NO: 5) was modified relative to the sequence of FIG. 6 (SEQ ID NO: 2) to be "T" rich.

FIG. 9: Top: Nucleotide sequence (SEQ ID NO: 11) encoding Ampicillin (Amp) resistance protein. Bottom: Nucleotide sequence (J-Amp) (SEQ ID NO: 13) encoding the same protein. Bold nucleotides of the bottom sequence (J-Amp) (SEQ ID NO: 13) are modified (mutated) relative to the top sequence (SEQ ID NO: 11).

FIG. 11: Nucleotide sequence (SEQ ID NO: 28) encoding tetracycline (Tet) resistance protein, and nucleotide sequence (J-Tet) (SEQ ID NO: 29) encoding the same protein. Bold nucleotides of the J-Tet sequence (SEQ ID NO: 29) are modified (mutated) relative to the Tet sequence (SEQ ID NO: 28).

DETAILED DESCRIPTION

Figure 2:
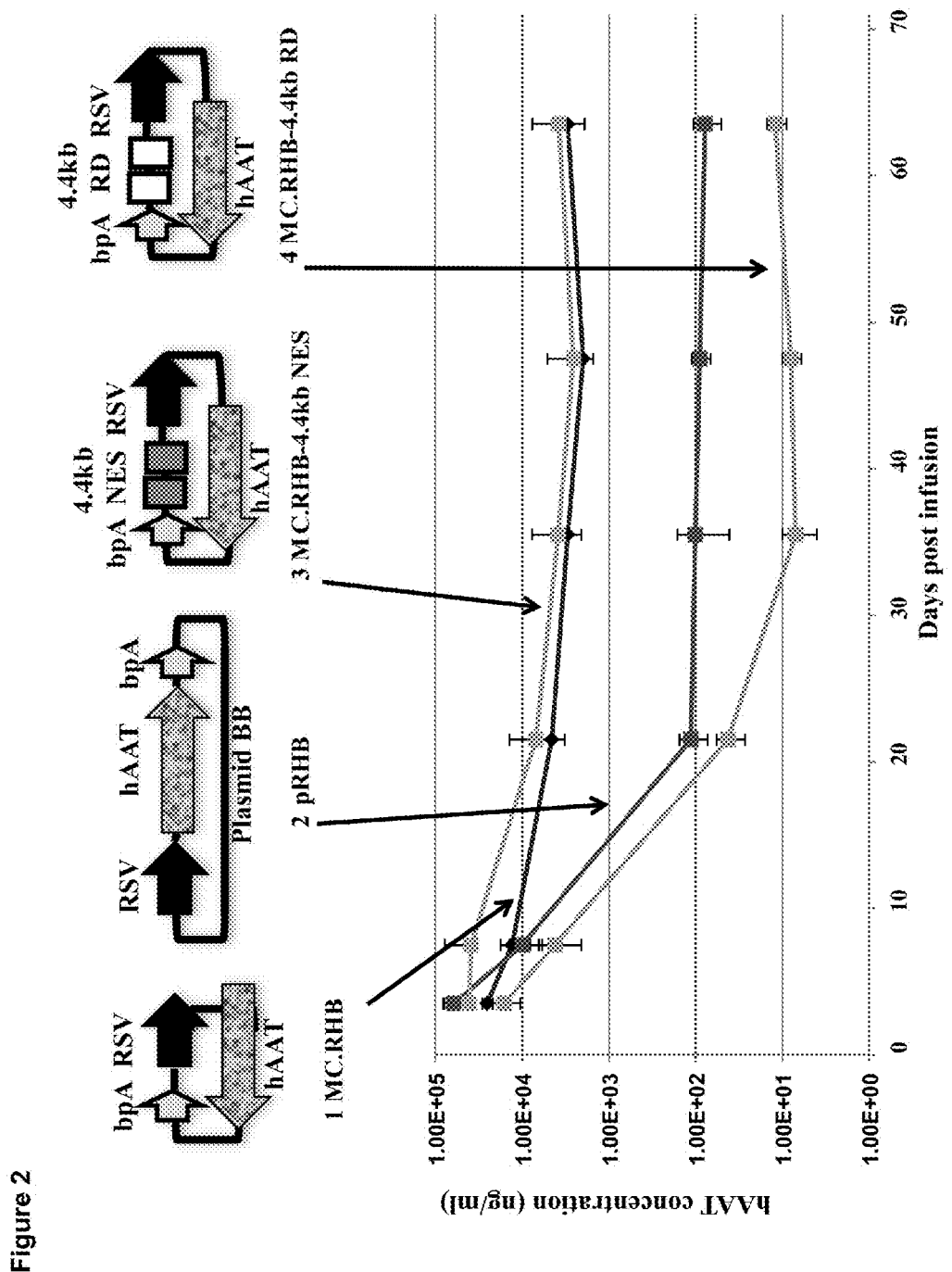
FIG. 2: RSV-hAAT expression constructs and transgene expression in mice. (Top) Schematic of hAAT expressing DNA constructs. Two copies of 2.2 kb NES sequence in FIG. 1 or random DNA (RD) sequence were placed after bpA sequence (bpA polyA signal) as spacer. "RSV" is Rous sarcoma virus (RSV) promoter. (Bottom) Serum hAAT levels at various time points after equimolar infusion of the plasmid vectors through hydrodynamic tail vein injection in mice (n=5/group). Error bars represent the standard deviation. This figure indicates that while an NES sequence did not silence transgene expression, the RD sequence at the same size did silence the transgene.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supercedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Provided are nucleic acids and expression vectors having a non-silencing selectable marker gene, and methods of using the same. A subject expression vector includes an expression cassette and a non-silencing selectable marker gene. In some cases, the non-silencing selectable marker gene provides for drug resistance for prokaryotic cells, and includes a nucleotide sequence that (i) encodes a drug selectable marker protein; (ii) is operably linked to a promoter functional in prokaryotic cells, and (iii) includes an increased A/T content relative to a corresponding wild type nucleotide sequence. In some cases, the non-silencing selectable marker gene provides for drug resistance for prokaryotic cells, and includes a nucleotide sequence that (i) encodes a drug selectable marker protein; (ii) is operably linked to a promoter functional in prokaryotic cells, and (iii) has an A/T content in a range of from 52% to 70%.

Definitions

By a "DNA molecule" it is meant the polymeric form of deoxyribonucleotides (adenine, guanine, thymine, or cytosine) in either single stranded form or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes.

The term "expression cassette" as used herein is a nucleic acid having a first nucleotide sequence (a nucleotide sequence of interest) operably linked to a second nucleotide sequence (e.g., a promoter, an enhancer, etc.) that is capable of directing the expression of the first nucleotide sequence (e.g., the first nucleotide sequence can be operably linked to the second nucleotide sequence). Any nucleotide sequence of interest is suitable (e.g., coding for any desired RNA transcript). Examples of suitable nucleotide sequences of interest include both protein coding sequences (e.g., sequences that code for mRNA) and sequences that do not code for protein (e.g., sequences that code for non-translated RNAs such as short hairpin RNAs (shRNAs), micro RNAs (microRNAs), short interfering RNAs (siRNAs), antisense RNAs, and the like).

Expression cassettes can be constructed into a "vector," "vector construct," "expression vector," or "gene transfer vector," in order to transfer the expression cassette into target cells. Thus, the term includes cloning and expression vehicles, as well as viral vectors. By a "vector" it is meant a nucleic acid that is capable of transferring a polynucleotide sequence, e.g. a transgene, to a target cell. For the purposes of the present disclosure, "vector construct," "expression vector," and "gene transfer vector," generally refer to any nucleic acid construct, for example, a linear nucleic acid, a circular nucleic acid, a phage, a virus, a viral genome (a viral construct), a cosmid, and the like, that is capable of transferring a gene of interest into target cells. Thus, the term includes cloning and expression vehicles, and extrachomosomally maintained vectors as well as integrating vectors.

By a "plasmid" it is meant a circular vector that comprises an origin of replication and a selectable marker. By a "plasmid backbone" it is meant the region of a plasmid that comprises the origin of replication and selectable marker, as well as bacterial sequences that flank these elements. By an "origin of replication" or "replication origin" it is meant a particular sequence in a genome at which replication is initiated. Origins of replication are found in prokaryotes and eukaryotes, and are required for the propagation of the plasmid episomally (i.e. extragenomically) in host cells.

As used herein, the term "transgene" can be used to refer to a nucleotide sequence of interest that (i) is operably linked to a promoter (e.g., a promoter functional in eukaryotic cells, e.g., mammalian cells) as part of an expression cassette, (ii) encodes a product (e.g., mRNA, non-coding RNA), and (iii) is capable of being expressed in a target cell (e.g., a prokaryotic cell, a eukaryotic cell, a mammalian cell, a rodent cell, a primate cell, a human cell, etc.). Non-limiting examples of transgenes include polynucleotide sequences that encode a peptide or polypeptide (protein coding sequences, sequences that code for mRNA), and polynucleotide sequences that encode a non-translated RNA (non-coding RNA, ncRNA) (e.g., a double stranded RNA or a single stranded RNA such as antisense RNA, sRNA, shRNA, miRNA, etc.). In some cases, a transgene is operably linked to a promoter functional in eukaryotic cells (e.g., mammalian cells).

Any convenient promoter is suitable for use with the nucleic acids described herein (e.g., expression vectors, expression cassettes, etc.). Examples of suitable promoters include but are not limited to those operable in prokaryotic cells (promoters functional in prokaryotic cells) and those that are operable in eukaryotic cells (promoters functional in eukaryotic cells) (e.g., mammalian cells, rodent cells, primate cells, and/or human cells, and the like).

As used herein, a "promoter" or "promoter sequence" is a DNA regulatory region capable of binding RNA polymerase in a cell and initiating transcription of a downstream (3' direction) coding sequence. For purposes of the present disclosure, the promoter sequence can be bounded at its 3' terminus by the transcription initiation site and extend upstream (5' direction) to include the minimum number of bases or elements necessary to initiate transcription at levels detectable above background. Within the promoter sequence can be found a transcription initiation site, as well as protein binding domains responsible for the binding of RNA polymerase. Eukaryotic promoters will often, but not always, contain "TATA" boxes and "CAT" boxes. Various promoters may be used to drive the various vectors of the present invention. For example, the promoter may be a constitutively active promoter, i.e. a promoter that is active in the absence externally applied agents, e.g. the CMV IE1 promoter, the SV40 promoter, the GAPDH promoter, the RSV promoter, the Actin promoter, and the like. The promoter may be an inducible promoter, i.e. a promoter whose activity is regulated upon the application of an agent to the cell, e.g. doxycycline, the tet-on or tet-off promoter, the estrogen receptor promoter, etc. The promoter may be a tissue-specific promoter, i.e. a promoter that is active in certain types of cells.

By a DNA "coding sequence" it is meant a DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and synthetic DNA sequences. A polyadenylation signal and transcription termination sequence may be located 3' to the coding sequence.

"DNA regulatory sequences", as used herein, are transcriptional and translational control sequences, such as promoters, enhancers, polyadenylation signals, terminators, and the like, that provide for and/or regulate expression of a coding sequence in a host cell.

As used herein, the term "reporter gene" refers to a coding sequence attached to heterologous promoter or enhancer elements and whose product may be assayed easily and quantifiably when the construct is introduced into tissues or cells.

By a "selectable marker gene", or "selection", marker, it is meant a coding sequence (e.g., a sequence encoding a selectable marker protein such as a drug selectable marker protein) that allows for selective retention of cells comprising a nucleic acid of interest (e.g. a plasmid), during culturing and propagation in the host cells. Non-limiting examples of selectable markers include those genes that provide for resistance to antibiotics such as amp, kan, neo, etc.; those useful in balanced lethal systems, in which an essential gene is maintained on the plasmid with a corresponding chromosomal deletion or suppressible mutation on the host cell genome, e.g. a tRNA selectable marker that suppresses a host chromosomal arg gene mutation; those useful in repressor titration systems, in which an operator sequences, e.g. the lac operator or tet operator, placed on a multicopy plasmid, derepresses a chromosomal gene; antidote/poison selection schemes, in which an antidote (e.g. the ccdA gene) to a poison expressed from the host chromosome (e.g. the ccdB gene) is maintained on the plasmid; and those useful in RNA-based selection schemes, e.g. RNAI and RNAII antisense regulators, or antisense regulators that inhibit the translation of a gene (SacB) transcribed from the host chromosome that would otherwise promote cell death.

As used herein, a cell has been "transformed" or "transfected" by exogenous or heterologous DNA, e.g. a DNA construct, when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

The amino acids described herein are preferred to be in the "L" isomeric form. The amino acid sequences are given in one-letter code (A: alanine; C: cysteine; D: aspartic acid; E: glutamic acid; F: phenylalanine; G: glycine; H: histidine; I: isoleucine; K: lysine; L: leucine; M: methionine; N: asparagine; P: proline; Q: glutamine; R: arginine; S: serine; T: threonine; V: valine; W: tryptophan; Y: tyrosine; X: any residue). In keeping with standard polypeptide nomenclature, NH2 refers to the free amino group present at the amino terminus (the N terminus) of a polypeptide, while COOH refers to the free carboxy group present at the carboxy terminus (the C terminus) of a polypeptide.

General methods in molecular and cellular biochemistry can be found in such standard textbooks as Molecular Cloning: A Laboratory Manual, 3rd Ed. (Sambrook et al., HaRBor Laboratory Press 2001); Short Protocols in Molecular Biology, 4th Ed. (Ausubel et al. eds., John Wiley & Sons 1999); Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998), the disclosures of which are incorporated herein by reference. Reagents, cloning vectors, and kits for genetic manipulation referred to in this disclosure are available from commercial vendors such as BioRad, Stratagene, Invitrogen, Sigma-Aldrich, and ClonTech.

Compositions and methods are provided for achieving persistent, high level expression of transgenes in vitro and in vivo. Aspects of the invention include nucleic acids comprising a non-silencing selectable marker gene, as well as vectors comprising both a non-silencing selectable marker gene and an expression cassette for expressing a transgene.

Compositions

Bacterial elements useful for the propagation of a plasmid, i.e. origin of replication, and selection of the plasmid in bacteria, i.e. selectable markers, have been shown previously to promote silencing of transgenes that are expressed from a vector, e.g. as a plasmid. However, the inventors of this disclosure have discovered that selectable marker genes do not have a silencing effect on transgene expression (i.e., they are "non-silencing") if they include an increased A/T content (provided they are operably linked to promoter functional in cells under which selection will take place, e.g., prokaryotic cells, and provided they still function as selectable marker genes in cells under which selection will take place, e.g., prokaryotic cells). For example, non-silencing selectable marker genes can be designed to include increased A/T content. In additions, non-silencing selectable marker genes can have an increase in the number of Poly-A/Poly-T tracts, while avoiding (e.g., keeping to a minimum, providing a reduced number of, etc.) the presence polymerase II pause sites.

Non Silencing Selectable Marker Genes

Nucleic acids (e.g., expression vectors) are provided that include a subject non-silencing selectable marker gene. A non-silencing selectable marker gene is a selectable marker gene that does not silence transgene expression from an expression vector, even when present on the same vector. In other words, an expression vector that includes an expression cassette that provides for persistent and high level expression of a transgene in a eukaryote (e.g., a mammal), can also include a selectable marker gene (i.e., no need to remove the selectable marker gene) if the selectable marker gene is a subject non-silencing selectable marker gene. It is the sequence of a subject non-silencing selectable marker gene (i.e., the sequence that encodes a selectable marker protein such as a drug selectable marker protein) that gives the marker gene the property of being "non-silencing." Parameters of a subject nucleotide sequence (of a non-silencing selectable marker gene) are discussed in further detail below (e.g., with regard to A/T content, T:A ratio, presence of Poly-A/Poly-T tracts, and/or presence or absence of polymerase II pause sites).

A "non-silencing selectable marker gene" has the property of being a "selectable marker gene" by virtue of its ability to provide for selection, i.e., for selective retention of cells (e.g., prokaryotic cells) that comprise the non-silencing selectable marker gene, during culturing and propagation in the host cells. Thus, a "non-silencing selectable marker gene" is "non-silencing" and is a "selectable marker gene". Thus, for example, in some cases, a subject non-silencing selectable marker gene includes a nucleotide sequence encoding a drug selectable marker protein that provides drug resistance for prokaryotic cells.

In some embodiments, a subject nucleotide sequence encoding a selectable marker protein (e.g. a drug selectable marker protein) is modified relative to a corresponding wild type nucleotide sequence. By "corresponding wild type nucleotide sequence" is meant a wild type sequence (in some cases a sequence of a prokaryotic cell) that encodes a selectable marker protein that provides for the same selection (e.g., drug resistance to the same drug) as the selectable marker protein encoded by the subject nucleotide sequence. The encoded protein does not have to be 100% identical (e.g., can be 85% or more identical, 90% or more identical, 95% or more identical, 98% or more identical, 99% or more identical, etc.), but the proteins perform the same biochemical function and retain enough sequence identity that they are considered homologous. A "corresponding wild type nucleotide sequence" can be identified at the nucleotide sequence level (and the encoded amino acid sequence can also be evaluated) using any convenient method (e.g., using any convenient sequence comparison/alignment software such as BLAST, etc.).

In some cases, a corresponding wild type nucleotide sequence (and therefore the subject nucleotide sequence encoding a selectable marker protein) encodes a drug selectable marker protein that provides resistance for prokaryotic cells to one or more drugs selected from: kanamycin, neomycin, ampicillin, carbenicillin, chloramphenicol, gentamicin, tetracycline, rifampin, trimethoprim, hygromycin B, and spectinomycin.

Proteins that provide drug resistance to cells (e.g., prokaryotic cells) in which they are expressed are known in the art. For example, wild type genes/proteins are known that provide resistance (e.g., for prokaryotic cells) to the above drugs. For example, aminoglycoside 3'-phosphotransferase (APH), is a wild type protein that provides for resistance to the drugs Kanamycin, Neomycin and Geneticin (G418); while beta-lactamase is a wild type protein that provides for resistance to the drugs ampicillin and carbenecillin. Chloramphenicol acetyltransferase (cat) confers resistance to chloramphenicol. Genes conferring resistance to aminoglycosides include aac, aad, aph and strA/B. Genes conferring resistance to β-lactams include ampC, cmy, tem and vim. Genes conferring resistance to sulfonamides include suII and suIII. Genes conferring resistance to tetracycline include tet(A), tet(B), tet(C), tet(D) and regulator, and tetR.

In some cases, a corresponding wild type nucleotide sequence encodes a drug selectable marker protein that provides resistance for prokaryotic cells to kanamycin. In some cases, a corresponding wild type nucleotide sequence encodes a drug selectable marker protein that provides resistance for prokaryotic cells to kanamycin and the drug selectable marker protein includes the amino acid sequence set forth in SEQ ID NO: 20. In some such cases, the corresponding wild type nucleotide sequence is set forth in SEQ ID NO: 2. Thus, in some cases, a subject non-silencing selectable marker gene includes a nucleotide sequence that (i) encodes a drug selectable marker protein (e.g, that provides resistance to kanamycin), and (ii) is modified relative to the corresponding wild type nucleotide sequence set forth in SEQ ID NO: 2.

In some cases, a corresponding wild type nucleotide sequence encodes a drug selectable marker protein that provides resistance for prokaryotic cells to ampicillin. In some cases, a corresponding wild type nucleotide sequence encodes a drug selectable marker protein that provides resistance for prokaryotic cells to ampicillin and the drug selectable marker protein includes the amino acid sequence set forth in SEQ ID NO: 25. In some such cases, the corresponding wild type nucleotide sequence is set forth in SEQ ID NO: 11. Thus, in some cases, a subject non-silencing selectable marker gene includes a nucleotide sequence that (i) encodes a drug selectable marker protein (e.g, that provides resistance to ampicillin), and (ii) is modified relative to the corresponding wild type nucleotide sequence set forth in SEQ ID NO: 11.

In some cases, a corresponding wild type nucleotide sequence encodes a drug selectable marker protein that provides resistance for prokaryotic cells to tetracycline. In some cases, a corresponding wild type nucleotide sequence encodes a drug selectable marker protein that provides resistance for prokaryotic cells to tetracycline and the drug selectable marker protein includes the amino acid sequence set forth in SEQ ID NO: 30. In some such cases, the corresponding wild type nucleotide sequence is set forth in SEQ ID NO: 28. Thus, in some cases, a subject non-silencing selectable marker gene includes a nucleotide sequence that (i) encodes a drug selectable marker protein (e.g, that provides resistance to tetracycline), and (ii) is modified relative to the corresponding wild type nucleotide sequence set forth in SEQ ID NO: 28.

In some cases, a corresponding wild type nucleotide sequence encodes a drug selectable marker protein that includes the amino acid sequence set forth in any one of SEQ ID NOs: 20, 25, and 30. Thus, in some cases, a subject drug selectable marker protein comprises an amino acid sequence having 85% or more sequence identity with the amino acid sequence set forth in any of SEQ ID NOs: 20, 25, and 30.

In some cases, a corresponding wild type nucleotide sequence encodes a drug selectable marker protein that provides resistance for prokaryotic cells to chloramphenicol. In some cases, a corresponding wild type nucleotide sequence encodes a drug selectable marker protein that provides resistance for prokaryotic cells to gentamicin. In some cases, a corresponding wild type nucleotide sequence encodes a drug selectable marker protein that provides resistance for prokaryotic cells to tetracycline. In some cases, a corresponding wild type nucleotide sequence encodes a drug selectable marker protein that provides resistance for prokaryotic cells to rifampin. In some cases, a corresponding wild type nucleotide sequence encodes a drug selectable marker protein that provides resistance for prokaryotic cells to trimethoprim. In some cases, a corresponding wild type nucleotide sequence encodes a drug selectable marker protein that provides resistance for prokaryotic cells to hygromycin B. In some cases, a corresponding wild type nucleotide sequence encodes a drug selectable marker protein that provides resistance for prokaryotic cells to spectinomycin.

Thus, in some cases, a subject nucleotide sequence encoding a selectable marker protein encodes a drug selectable marker protein that provides resistance for prokaryotic cells to one or more drugs selected from: kanamycin, neomycin, ampicillin, carbenicillin, chloramphenicol, gentamicin, tetracycline, rifampin, trimethoprim, hygromycin B, and spectinomycin.

In some cases, a subject nucleotide sequence encoding a selectable marker protein encodes a drug selectable marker protein that provides resistance for prokaryotic cells to kanamycin. For example, in some cases, a subject nucleotide sequence encoding a selectable marker protein encodes a drug selectable marker protein that provides resistance for prokaryotic cells to kanamycin, where the drug selectable marker protein includes an amino acid sequence having 85% or more sequence identity (e.g, 90% or more, 95% or more, 98% or more, 99% or more, or 100% or more sequence identity) with the amino acid sequence set forth in any of SEQ ID NOs: 20-21. In some cases, a subject nucleotide sequence encoding a selectable marker protein encodes a drug selectable marker protein that provides resistance for prokaryotic cells to kanamycin, where the drug selectable marker protein includes an amino acid sequence having 85% or more sequence identity (e.g, 90% or more, 95% or more, 98% or more, 99% or more, or 100% or more sequence identity) with the amino acid sequence set forth in SEQ ID NO: 20.

In some cases, a subject nucleotide sequence encoding a selectable marker protein encodes a drug selectable marker protein that provides resistance for prokaryotic cells to ampicillin. For example, in some cases, a subject nucleotide sequence encoding a selectable marker protein encodes a drug selectable marker protein that provides resistance for prokaryotic cells to ampicillin, where the drug selectable marker protein includes an amino acid sequence having 85% or more sequence identity (e.g, 90% or more, 95% or more, 98% or more, 99% or more, or 100% or more sequence identity) with the amino acid sequence set forth in any of SEQ ID NOs: 25-26. In some cases, a subject nucleotide sequence encoding a selectable marker protein encodes a drug selectable marker protein that provides resistance for prokaryotic cells to ampicillin, where the drug selectable marker protein includes an amino acid sequence having 85% or more sequence identity (e.g, 90% or more, 95% or more, 98% or more, 99% or more, or 100% or more sequence identity) with the amino acid sequence set forth in SEQ ID NO: 25.

In some cases, a subject nucleotide sequence encoding a selectable marker protein encodes a drug selectable marker protein that provides resistance for prokaryotic cells to tetracycline. For example, in some cases, a subject nucleotide sequence encoding a selectable marker protein encodes a drug selectable marker protein that provides resistance for prokaryotic cells to tetracycline, where the drug selectable marker protein includes an amino acid sequence having 85% or more sequence identity (e.g, 90% or more, 95% or more, 98% or more, 99% or more, or 100% or more sequence identity) with the amino acid sequence set forth in SEQ ID NO: 30.

In some cases, a subject nucleotide sequence encoding a selectable marker protein encodes a drug selectable marker protein that includes an amino acid sequence having 85% or more sequence identity (e.g, 90% or more, 95% or more, 98% or more, 99% or more, or 100% or more sequence identity) with the amino acid sequence set forth in any of SEQ ID NOs: 20-21, 25-26, and 30. In some cases, a subject nucleotide sequence encoding a selectable marker protein encodes a drug selectable marker protein that includes an amino acid sequence having 85% or more sequence identity (e.g, 90% or more, 95% or more, 98% or more, 99% or more, or 100% or more sequence identity) with the amino acid sequence set forth in any of SEQ ID NOs: 20, 25, and 30.

In some cases, a subject nucleotide sequence encoding a selectable marker protein encodes a drug selectable marker protein that provides resistance for prokaryotic cells to chloramphenicol. In some cases, a subject nucleotide sequence encoding a selectable marker protein encodes a drug selectable marker protein that provides resistance for prokaryotic cells to gentamicin. In some cases, a subject nucleotide sequence encoding a selectable marker protein encodes a drug selectable marker protein that provides resistance for prokaryotic cells to tetracycline. In some cases, a subject nucleotide sequence encoding a selectable marker protein encodes a drug selectable marker protein that provides resistance for prokaryotic cells to rifampin. In some cases, a subject nucleotide sequence encoding a selectable marker protein encodes a drug selectable marker protein that provides resistance for prokaryotic cells to trimethoprim. In some cases, a subject nucleotide sequence encoding a selectable marker protein encodes a drug selectable marker protein that provides resistance for prokaryotic cells to hygromycin B. In some cases, a subject nucleotide sequence encoding a selectable marker protein encodes a drug selectable marker protein that provides resistance for prokaryotic cells to spectinomycin.

A/T Content and T:A Ratio

In some cases, a nucleotide sequence encoding a selectable marker protein (e.g., a nucleotide sequence of a subject non-silencing selectable marker gene) includes an increased A/T content relative to a corresponding wild type nucleotide sequence (e.g., see SEQ ID NOs: 2, 11, and 28 for wild type nucleotide sequences encoding proteins that provide for resistance to kanamycin, ampicillin, and tetracycline, respectively) (e.g., see working examples and Tables 1-9).

TABLE 1

Nucleotide content (A/T/G/C) of genes encoding selectable marker proteins that provide resistance to Ampicillin (Amp) or Kanamycin (Kan). (Also see working examples below)

| Gene | SEQ ID NO: | % A | % T | % G | % C | % A/T | % G/C | T:A ratio |
|---|---|---|---|---|---|---|---|---|
| Ampicillin | | | | | | | | |
| Amp-1 | 11 | 26.0 | 24.9 | 25.7 | 23.5 | 50.9 | 49.1 | 0.96 |
| Amp-2 | 12 | 26.9 | 33.1 | 22.9 | 17.1 | 60 (1.2 fold) | 40 | 1.23 (1.3 fold) |
| J-Amp | 13 | 30.8 | 34.8 | 19.5 | 14.9 | 65.6 (1.3 fold) | 34.4 | 1.13 (1.2 fold) |

TABLE 1-continued

Nucleotide content (A/T/G/C) of genes encoding selectable marker proteins that provide resistance to Ampicillin (Amp) or Kanamycin (Kan). (Also see working examples below)

| Gene | SEQ ID NO: | % A | % T | % G | % C | % A/T | % G/C | T:A ratio |
|---|---|---|---|---|---|---|---|---|
| Kanamycin | | | | | | | | |
| Kan-1 | 2 | 18.1 | 22.1 | 31.3 | 28.4 | 40.3 | 59.7 | 1.22 |
| Kan-2 | 3 | 23.4 | 36.7 | 24.4 | 15.5 | 60.1 (1.5 fold) | 39.9 | 1.57 (1.3 fold) |
| J-Kan | 4 | 26.7 | 34.7 | 22.8 | 15.8 | 61.4 (1.5 fold) | 38.6 | 1.30 (1.1 fold) |
| JT-Kan | 5 | 13.3 | 39.1 | 27.3 | 20.3 | 52.5 (1.3 fold) | 47.5 | 2 93 (2.4 fold) |
| Tetracycline | | | | | | | | |
| Tet | 28 | 16 | 22.5 | 29.6 | 31.9 | 38.5 | 61.5 | 1.41 |
| J-Tet | 29 | 23.4 | 38.9 | 21.8 | 15.9 | 62.3 (1.6 fold) | 37.7 | 1.66 (1.2 fold) |

Notes:
(i) (x fold) refers to the fold increase relative to the first row (e.g., Amp-1, Kan-1, Tet); (ii) In the experiments of Example 1 below, the JT-Kan sequence did not function as a "selectable marker gene" (and therefore did not function as a "non silencing selectable marker gene") because it did not provide resistance for the tested prokaryotic cells to kanamycin despite encoding the same protein as J-Kan.

TABLE 2

Percent identity (nucleotides) for Amp genes of Table 1.

| Gene (SEQ ID NO:) | Amp-1 | Amp-2 | J-Amp |
|---|---|---|---|
| Amp-1 (11) | 100 | 76 | 82 |
| Amp-2 (12) | 76 | 100 | 87 |
| J-Amp (13) | 82 | 87 | 100 |

TABLE 3

Percent identity (nucleotides) for Kan genes of Table 1.

| Gene (SEQ ID NO:) | Kan-1 | Kan-2 | J-Kan | JT-Kan |
|---|---|---|---|---|
| Kan-1 (2) | 100 | 71 | 77 | 78 |
| Kan-2 (3) | 71 | 100 | 86 | 82 |
| J-Kan (4) | 77 | 86 | 100 | 81 |
| JT-Kan (5) | 78 | 82 | 81 | 100 |

TABLE 4

Percent identity (nucleotides) for Tet genes of Table 1.

| Gene (SEQ ID NO:) | Tet | J-Tet |
|---|---|---|
| Tet (28) | 100 | 72 |
| J-Tet (29) | 72 | 100 |

TABLE 5

Percent amino acid identity for proteins encoded by Amp genes of Table 1.

| Gene (SEQ ID NO:) | Amp-1 | Amp-2 | J-Amp |
|---|---|---|---|
| Amp-1 (25) | 100 | 99 | 100 |
| Amp-2 (26) | 99 | 100 | 99 |
| J-Amp (27) | 100 | 99 | 100 |

TABLE 6

Percent amino acid identity for proteins encoded by Amp genes of Table 1.

| Gene (SEQ ID NO:) | Amp-1 | Amp-2 | J-Amp |
|---|---|---|---|
| Amp-1 (25) | 100 | 99 | 100 |
| Amp-2 (26) | 99 | 100 | 99 |
| J-Amp (27) | 100 | 99 | 100 |

TABLE 7

Percent amino acid identity for proteins encoded by Tet genes of Table 1.

| Gene (SEQ ID NO:) | Tet | J-Tet |
|---|---|---|
| Tet (30) | 100 | 100 |
| J-Tet (31) | 100 | 100 |

In some cases, a nucleotide sequence encoding a selectable marker protein (e.g., a nucleotide sequence of a subject non-silencing selectable marker gene) includes an A/T content that is 1.1 fold or more greater than the A/T content of the corresponding wild type nucleotide sequence (e.g., 1.2 fold or more, 1.3 fold or more, or 1.4 fold or more greater than the A/T content of the corresponding wild type nucleotide sequence). In some cases, a nucleotide sequence encoding a selectable marker protein (e.g., a nucleotide sequence of a subject non-silencing selectable marker gene) includes an A/T content that is increased relative to a corresponding wild type nucleotide sequence by a range of from 1.1 fold to 1.8 fold (e.g., from 1.1 fold to 1.7 fold, from 1.1 fold to 1.6 fold, from 1.1 fold to 1.5 fold, from 1.2 fold to 1.8 fold, from 1.2 fold to 1.7 fold, from 1.2 fold to 1.6 fold, from 1.2 fold to 1.5 fold, from 1.3 fold to 1.8 fold, from 1.3 fold to 1.7 fold, from 1.3 fold to 1.6 fold, or from 1.3 fold to 1.5 fold).

In some cases, a nucleotide sequence encoding a selectable marker protein (e.g., a nucleotide sequence of a subject non-silencing selectable marker gene) includes an A/T content of 42% or more (e.g., 45% or more, 48% or more, 50% or more, 52% or more, 54% or more, 56% or more, 58% or more, 60% or more, 62% or more, or 64% or more). In some cases, a nucleotide sequence encoding a selectable marker protein (e.g., a nucleotide sequence of a subject non-silencing selectable marker gene) includes an A/T content of 52% or more (e.g., 53% or more, 54% or more, 56% or more, 58% or more, 60% or more, 62% or more, or 64% or more). In some cases, a nucleotide sequence of a subject non-silencing selectable marker gene that encodes a drug selectable marker protein that provides for resistance to kanamycin includes an A/T content of 42% or more (e.g., 45% or more, 48% or more, 50% or more, 52% or more, 54% or more, 56% or more, 58% or more, 60% or more, 62% or more, or 64% or more). In some cases, a nucleotide sequence of a subject non-silencing selectable marker gene that encodes a drug selectable marker protein that provides for resistance to ampicillin includes an A/T content of 52% or more (e.g., 53% or more, 54% or more, 56% or more, 58% or more, 60% or more, 62% or more, or 64% or more).

In some cases, a nucleotide sequence encoding a selectable marker protein (e.g., a nucleotide sequence of a subject non-silencing selectable marker gene) includes an A/T content in a range of from of 42% to 70% (e.g., from 45% to 70%, from 48% to 70%, from 50% to 70%, from 52% to 70%, from 54% to 70%, from 56% to 70%, from 58% to 70%, from 60% to 70%, from 42% to 68%, from 45% to 68%, from 48% to 68%, from 50% to 68%, from 52% to 68%, from 54% to 68%, from 56% to 68%, from 58% to 68%, from 60% to 68%, from 42% to 67%, from 45% to 67%, from 48% to 67%, from 50% to 67%, from 52% to 67%, from 54% to 67%, from 56% to 67%, from 58% to 67%, or from 60% to 67%).

In some cases, a nucleotide sequence of a subject non-silencing selectable marker gene that encodes a drug selectable marker protein that provides for resistance to kanamycin includes an A/T content in a range of from of 42% to 70% (e.g., from 45% to 70%, from 48% to 70%, from 50% to 70%, from 52% to 70%, from 54% to 70%, from 56% to 70%, from 58% to 70%, from 42% to 68%, from 45% to 68%, from 48% to 68%, from 50% to 68%, from 52% to 68%, from 54% to 68%, from 56% to 68%, from 58% to 68%, from 60% to 68%, from 42% to 66%, from 45% to 66%, from 48% to 66%, from 50% to 66%, from 52% to 66%, from 54% to 66%, from 56% to 66%, from 58% to 66%, from 60% to 66%, from 42% to 64%, from 45% to 64%, from 48% to 64%, from 50% to 64%, from 52% to 64%, from 54% to 64%, from 56% to 64%, from 58% to 64%, from 60% to 64%, from 42% to 62%, from 45% to 62%, from 48% to 62%, from 50% to 62%, from 52% to 62%, from 54% to 62%, from 56% to 62%, from 58% to 62%, or from 60% to 62%).

In some cases, a nucleotide sequence of a subject non-silencing selectable marker gene that encodes a drug selectable marker protein that provides for resistance to ampicillin includes an A/T content in a range of from of 52% to 70% (e.g., from 54% to 70%, from 56% to 70%, from 58% to 70%, from 60% to 70%, from 62% to 70%, from 64% to 70%, from 52% to 68%, from 54% to 68%, from 56% to 68%, from 58% to 68%, from 60% to 68%, from 62% to 68%, from 64% to 68%, from 52% to 67%, from 54% to 67%, from 56% to 67%, from 58% to 67%, from 60% to 67%, from 62% to 67%, or from 64% to 67%).

In some cases, a nucleotide sequence encoding a selectable marker protein (e.g., a nucleotide sequence of a subject non-silencing selectable marker gene) includes two or more codons that have a greater A/T content than the corresponding codons of a corresponding wild type nucleotide sequence. For examples, in some cases, a nucleotide sequence encoding a selectable marker protein (e.g., a nucleotide sequence of a subject non-silencing selectable marker gene) includes 3 or more codons (e.g., 4 or more, 5 or more, 10 or more, 15 or more, 20 or more, or 25 or more codons) that have a greater A/T content than the corresponding codons of a corresponding wild type nucleotide sequence.

In some cases, a nucleotide sequence encoding a selectable marker protein (e.g., a nucleotide sequence of a subject non-silencing selectable marker gene) includes 10% or more codons (e.g., 15% or more, 25% or more, 50% or more, or 70% or more codons) that have a greater A/T content than the corresponding codons of a corresponding wild type nucleotide sequence.

In some cases, a nucleotide sequence encoding a selectable marker protein (e.g., a nucleotide sequence of a subject non-silencing selectable marker gene) includes a T:A ratio that is 1.1 fold or more greater than the T:A ratio of the corresponding wild type nucleotide sequence (e.g., 1.2 fold or more, 1.3 fold or more greater than the T:A ratio of the corresponding wild type nucleotide sequence). In some cases, a nucleotide sequence encoding a selectable marker protein (e.g., a nucleotide sequence of a subject non-silencing selectable marker gene) includes a T:A ratio that is increased relative to a corresponding wild type nucleotide sequence by a range of from 1.1 fold to 1.8 fold (e.g., from 1.1 fold to 1.7 fold, from 1.1 fold to 1.6 fold, from 1.1 fold to 1.5 fold, from 1.1 fold to 1.4 fold, from 1.1 fold to 1.3 fold, from 1.2 fold to 1.8 fold, from 1.2 fold to 1.7 fold, from 1.2 fold to 1.6 fold, from 1.2 fold to 1.5 fold, from 1.2 fold to 1.4 fold, from 1.2 fold to 1.5 fold, from 1.3 fold to 1.8 fold, from 1.3 fold to 1.7 fold, from 1.3 fold to 1.6 fold, or from 1.3 fold to 1.5 fold).

For example, in some cases, a nucleotide sequence encoding a selectable marker protein that provides resistance to kanamycin (e.g., a nucleotide sequence of a subject non-silencing selectable marker gene) includes a T:A ratio that is increased relative to the T:A ratio of a corresponding wild type nucleotide sequence by 1.1 to 1.3 fold. For example, in some cases, a nucleotide sequence encoding a selectable marker protein that provides resistance to ampicillin (e.g., a nucleotide sequence of a subject non-silencing selectable marker gene) includes a T:A ratio that is increased relative to the T:A ratio of a corresponding wild type nucleotide sequence by 1.1 to 1.3 fold.

In some cases, a nucleotide sequence encoding a selectable marker protein (e.g., a nucleotide sequence of a subject non-silencing selectable marker gene) includes a T:A ratio in a range of from 0.8 to 2.5 (e.g., from 0.8 to 2.3, from 0.8 to 2.1, from 0.8 to 2.0, from 0.8 to 1.9, from 0.8 to 1.8, from 0.8 to 1.7, from 0.8 to 1.6, from 0.8 to 1.5, from 0.8 to 1.4, from 0.8 to 1.3, from 0.9 to 2.5, from 0.9 to 2.3, from 0.9 to 2.1, from 0.9 to 2.0, from 0.9 to 1.9, from 0.9 to 1.9, from 0.9 to 1.7, from 0.9 to 1.6, from 0.9 to 1.5, from 0.9 to 1.4, from 0.9 to 1.3, from 1.0 to 2.5, from 1.0 to 2.3, from 1.0 to 2.1, from 1.0 to 2.0, from 1.0 to 1.9, from 1.0 to 1.9, from 1.0 to 1.7, from 1.0 to 1.6, from 1.0 to 1.5, from 1.0 to 1.4, from 1.0 to 1.3, from 1.1 to 2.5, from 1.1 to 2.3, from 1.1 to 2.1, from 1.1 to 2.0, from 1.1 to 1.9, from 1.1 to 1.9, from 1.1 to 1.7, from 1.1 to 1.6, from 1.1 to 1.5, from 1.1 to 1.4, from 1.1 to 1.3, from 1.2 to 2.5, from 1.2 to 2.3, from 1.2 to 2.1, from 1.2 to 2.0, from 1.2 to 1.9, from 1.2 to 1.9, from 1.2 to 1.7, from 1.2 to 1.6, from 1.2 to 1.5, from 1.2 to 1.4, from 1.2 to 1.3, from 1.3 to 2.5, from 1.3 to 2.3, from 1.3 to 2.1, from 1.3 to 2.0, from 1.3 to 1.9, from 1.3 to 1.9, from 1.3 to 1.7, from 1.3 to 1.6, from 1.3 to 1.5, or from 1.3 to 1.4). For example, in some cases, a nucleotide sequence encoding a selectable marker protein that provides resistance to kanamycin (e.g., a nucleotide sequence of a subject non-silencing selectable marker gene) includes a T:A ratio in a range of from 1.2 to 1.6. In some cases, a nucleotide sequence encoding a selectable marker protein that provides resistance to ampicillin (e.g., a nucleotide sequence of a subject non-silencing selectable marker gene) includes a T:A ratio in a range of from 0.9 to 1.3.

In some cases, a nucleotide sequence encoding a selectable marker protein (e.g., a nucleotide sequence of a subject non-silencing selectable marker gene) has in a range of from 65% to 95% sequence identity (e.g., from 65% to 92%, from 65% to 90%, from 65% to 88%, from 65% to 85%, from 65% to 82%, from 65% to 80%, from 65% to 78%, from 68% to 95%, from 68% to 92%, from 68% to 90%, from 68% to 88%, from 68% to 85%, from 68% to 82%, from 68% to 80%, from 68% to 78%, from 70% to 95%, from 70% to 92%, from 70% to 90%, from 70% to 88%, from 70% to 85%, from 70% to 82%, from 70% to 80%, or from 70% to 78% sequence identity) with a corresponding wild type nucleotide sequence (e.g., SEQ ID NO: 2 (kan) and/or SEQ ID NO:11 (amp) and/or SEQ ID NO: 28 (Tet)).

In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in any of SEQ ID NOs: 3, 4, 12, 13, and 29. In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in any of SEQ ID NOs: 3 and 4. In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in any of SEQ ID NOs: 12 and 13. In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in any of SEQ ID NOs: 4, 13, and 29. In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in SEQ ID NOs: 29.

In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in SEQ ID NO: 4. For example, in some cases, a nucleotide sequence encoding a selectable marker protein (e.g., a nucleotide sequence of a subject non-silencing selectable marker gene) has 87% or more sequence identity (e.g., 88% or more, 90% or more, 92% or more, 95% or more, 96% or more, 98% or more, 99% or more, or 100% sequence identity) with the high A/T content nucleotide sequence set forth in SEQ ID NO: 4. In some cases, a nucleotide sequence encoding a selectable marker protein (e.g., a nucleotide sequence of a subject non-silencing selectable marker gene) includes the high A/T content nucleotide sequence set forth in SEQ ID NO: 4.

In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in SEQ ID NO: 13. For example, in some cases, a nucleotide sequence encoding a selectable marker protein (e.g., a nucleotide sequence of a subject non-silencing selectable marker gene) has 88% or more sequence identity (e.g., 90% or more, 92% or more, 95% or more, 96% or more, 98% or more, 99% or more, or 100% sequence identity) with the high A/T content nucleotide sequence set forth in SEQ ID NO: 13. In some cases, a nucleotide sequence encoding a selectable marker protein (e.g., a nucleotide sequence of a subject non-silencing selectable marker gene) includes the high A/T content nucleotide sequence set forth in SEQ ID NO: 13.

In some cases, a nucleotide sequence encoding a selectable marker protein (e.g., a nucleotide sequence of a subject non-silencing selectable marker gene) has 70% or more sequence identity (e.g., 72% or more, 73% or more, 75% or more, 78% or more, 80% or more, 82% or more, 85% or more, 87% or more, 88% or more, 90% or more, 92% or more, 95% or more, 96% or more, 98% or more, 99% or more, or 100% sequence identity) with the high A/T content nucleotide sequence set forth in SEQ ID NO: 29. For example, in some cases, a nucleotide sequence encoding a selectable marker protein (e.g., a nucleotide sequence of a subject non-silencing selectable marker gene) has 73% or more sequence identity (e.g., 75% or more, 80% or more, 85% or more, 90% or more, 92% or more, 95% or more, 96% or more, 98% or more, 99% or more, or 100% sequence identity) with the high A/T content nucleotide sequence set forth in SEQ ID NO: 29. In some cases, a nucleotide sequence encoding a selectable marker protein (e.g., a nucleotide sequence of a subject non-silencing selectable marker gene) includes the high A/T content nucleotide sequence set forth in SEQ ID NO: 29.

PolyT/PolyA Tract

In some cases, a subject nucleotide sequence encoding a selectable marker protein (e.g., a drug selectable marker protein) includes one or more Poly A tracts (e.g., 2 or more, 3 or more, 4 or more, 5 or more, or 6 or more Poly A tracts) (Table 8). In some cases, a subject nucleotide sequence encoding a selectable marker protein (e.g., a drug selectable marker protein) includes one or more Poly T tracts (e.g., 2 or more, 3 or more, 4 or more, 5 or more, or 6 or more Poly T tracts) (Table 8). In some cases, a subject nucleotide sequence encoding a selectable marker protein (e.g., a drug selectable marker protein) does not include a Poly A tract. In some cases, a subject nucleotide sequence encoding a selectable marker protein (e.g., a drug selectable marker protein) does not include a Poly T tract. In some cases, a subject nucleotide sequence encoding a encoding a selectable marker protein (e.g., a drug selectable marker protein) does not include a Poly A tract or a Poly T tract.

The terms "Poly A tract" and "Poly T tract" are used herein to refer to a stretch of 3 or more A or T consecutive nucleotides, respectively (e.g., 4 or more, 5 or more, or 6 or more consecutive A nucleotides; 4 or more, 5 or more, or 6 or more consecutive T nucleotides; etc.). For example, in some cases, a Poly A tract has 3 nucleotides; in some cases, a Poly A tract has 4 nucleotides; in some cases, a Poly A tract has 5 nucleotides; in some cases, a Poly A tract has 6 nucleotides; in some cases, a Poly A tract has 7 nucleotides; in some cases, a Poly A tract has 8 nucleotides. In some cases, a Poly T tract has 3 nucleotides; in some cases, a Poly T tract has 4 nucleotides; in some cases, a Poly T tract has 5 nucleotides; in some cases, a Poly T tract has 6 nucleotides; in some cases, a Poly T tract has 7 nucleotides; in some cases, a Poly T tract has 8 nucleotides.

In some cases, a subject nucleotide sequence encoding a selectable marker protein (e.g., a drug selectable marker protein) includes one or more Poly-A/Poly-T tracts (e.g., 2 or more, 3 or more, 4 or more, 5 or more, or 6 or more Poly-A/Poly-T tracts). The terms "Poly-A/Poly-T tracts", "Poly A tracts and/or Poly T tracts", and "Poly A/T tracts" are used interchangeably herein to mean a combination of all Poly A tracts and Poly T tracts. As an illustrative example, if a nucleotide sequence (e.g., a subject nucleotide sequence encoding a selectable marker protein, e.g., a drug selectable marker protein) includes 2 Poly A tracts and 1 Poly T tract, it can be referred to herein as having 3 Poly-A/Poly-T tracts. Likewise, if a nucleotide sequence includes 3 Poly A tracts and no Poly T tracts, or if it instead includes 3 Poly T tracts and no Poly A tracts, it can also be referred to herein as having 3 Poly-A/Poly-T tracts.

In some cases, for example when a subject nucleotide sequence encoding a selectable marker protein (e.g., drug selectable marker protein) includes two or more Poly-A/Poly-T tracts, the tracts can be the same or different, or any combination thereof (e.g., when considering A versus T and when considering length of the tracts, e.g., the tracts be of varying lengths). As an illustrative example, if a subject nucleotide sequence encoding a selectable marker protein (e.g., a drug selectable marker protein) includes 4 Poly-A/Poly-T tracts, each of the 4 tract lengths can be the same or different and each can independently be a Poly A tract or a Poly T tract. Thus, for example, such a nucleotide sequence could have 1 tract of AAA, 1 tract of TTTT, and two tracts of TTTTT. On the other hand, such a nucleotide sequence could have 2 tracts of AAAAA, 1 tract of AAAA, and 1 tract of TTTTT.

Likewise, when a subject nucleotide sequence encoding a selectable marker protein (e.g., a drug selectable marker protein) includes two or more Poly A/T tracts, the tracts can be of varying lengths. As an illustrative example, if a subject nucleotide sequence encoding a selectable marker protein (e.g., a drug selectable marker protein) includes 4 Poly A/T tracts, each of the 4 tract lengths can be the same or different, or any combination thereof. Thus, for example, such a nucleotide sequence could have 1 tract of AAA, 1 tract of TTTT, and two tracts of TTTTT.

In some cases, a subject nucleotide sequence encoding a selectable marker protein (e.g., a drug selectable marker protein) includes an increased number of Poly-A/Poly-T tracts relative to the number of Poly-A/Poly-T tracts present in the corresponding wild type nucleotide sequence. In some cases, a subject nucleotide sequence encoding a selectable marker protein (e.g., a drug selectable marker protein) includes one or more Poly-A/Poly-T tracts that are greater in length (e.g., two or more, three or more, or four or more Poly-A/Poly-T tracts that are greater in length) than a corresponding Poly-A/Poly-T tract present in the corresponding wild type nucleotide sequence. In some cases, a subject nucleotide sequence encoding a selectable marker protein (e.g., a drug selectable marker protein) includes (a) an increased number of Poly-A/Poly-T tracts relative to the number of Poly-A/Poly-T tracts present in the corresponding wild type nucleotide sequence and/or (b) one or more Poly-A/Poly-T tracts that are greater in length (e.g., two or more, three or more, or four or more Poly-A/Poly-T tracts that are greater in length) than a corresponding Poly-A/Poly-T tract present in the corresponding wild type nucleotide sequence.

In some cases, a subject nucleotide sequence encoding a selectable marker protein (e.g., a drug selectable marker protein) includes 4 or more (e.g., 5 or more, 6 or more, 7 or more, 8 or more, 9 or more, or 10 or more, 12 or more, 14 or more, 16 or more, 18 or more, 20 or more, 22 or more, 24 or more, or 26 or more) Poly T tracts, each of which have 3 or more consecutive T nucleotides. In some cases, a subject nucleotide sequence encoding a selectable marker protein (e.g., a drug selectable marker protein) includes 10 or more (e.g., 11 or more, 12 or more, 14 or more, 16 or more, 18 or more, 20 or more, 22 or more, 24 or more, or 26 or more) Poly T tracts, each of which have 3 or more consecutive T nucleotides. (see Table 8).

In some cases, a subject nucleotide sequence encoding a selectable marker protein (e.g., a drug selectable marker protein) includes 4 or more (e.g., 5 or more, 6 or more, 7 or more, 8 or more, 9 or more, or 10 or more, 12 or more, 14 or more, 16 or more, 18 or more, or 20 or more) Poly A tracts, each of which have 3 or more consecutive A nucleotides. In some cases, a subject nucleotide sequence encoding a selectable marker protein (e.g., a drug selectable marker protein) includes 11 or more (e.g., 12 or more, 14 or more, 16 or more, 18 or more, or 20 or more) Poly A tracts, each of which have 3 or more consecutive A nucleotides. (see Table 8).

In some cases, a subject nucleotide sequence encoding a selectable marker protein (e.g., a drug selectable marker protein) includes 7 or more (e.g., 8 or more, 9 or more, or 10 or more, 12 or more, 14 or more, 16 or more, 18 or more, 20 or more, 22 or more, 24 or more, 26 or more, 28 or more, 30 or more, 32 or more, 34 or more, 36 or more, 38 or more, or 40 or more) Poly-A/poly-T tracts, each of which have 3 or more consecutive A or T nucleotides. In some cases, a subject nucleotide sequence encoding a selectable marker protein (e.g., a drug selectable marker protein) includes 20 or more (e.g., 22 or more, 24 or more, 26 or more, 28 or more, 30 or more, 32 or more, 34 or more, 36 or more, 38 or more, or 40 or more) Poly-A/poly-T tracts, each of which have 3 or more consecutive A or T nucleotides. (see Table 8).

In some cases, a subject nucleotide sequence encoding a selectable marker protein (e.g., a drug selectable marker protein) includes 4 or more (e.g., 5 or more, 6 or more, 7 or more, 8 or more, 9 or more, or 10 or more) Poly T tracts, each of which have 4 or more consecutive T nucleotides. In some cases, a subject nucleotide sequence encoding a selectable marker protein (e.g., a drug selectable marker protein) includes 8 or more (e.g., 9 or more, 10 or more, 11 or more, or 12 or more) Poly T tracts, each of which have 4 or more consecutive T nucleotides. In some cases, a subject nucleotide sequence encoding a selectable marker protein (e.g., a drug selectable marker protein) includes 4 or more (e.g., 5 or more, or 6 or more) Poly A tracts, each of which have 4 or more consecutive A nucleotides. (see Table 8).

In some cases, a subject nucleotide sequence encoding a selectable marker protein (e.g., a drug selectable marker protein) includes 4 or more (e.g., 5 or more, 6 or more, 7 or more, 8 or more, 9 or more, 10 or more, 11 or more, 12 or more, 13 or more, 14 or more, 15 or more, or 16 or more) Poly-A/poly-T tracts, each of which have 4 or more consecutive A or T nucleotides. In some cases, a subject nucleotide sequence encoding a selectable marker protein (e.g., a drug selectable marker protein) includes 10 or more (e.g., 11 or more, 12 or more, 13 or more, 14 or more, 15 or more, or 16 or more) Poly-A/poly-T tracts, each of which have 4 or more consecutive A or T nucleotides. (see Table 8).

In some cases, a subject nucleotide sequence encoding a selectable marker protein (e.g., a drug selectable marker protein) includes 4 or more (e.g., 5 or more, 6 or more, or 7 or more) Poly T tracts, each of which have 5 or more consecutive T nucleotides. In some cases, a subject nucleotide sequence encoding a selectable marker protein (e.g., a drug selectable marker protein) includes one or more Poly A tracts, each of which have 5 or more consecutive A nucleotides. In some cases, a subject nucleotide sequence encoding a selectable marker protein (e.g., a drug selectable marker protein) includes 4 or more (e.g., 5 or more, 6 or more, 7 or more, or 8 or more) Poly-A/poly-T tracts, each of which have 5 or more consecutive A or T nucleotides. (see Table 8).

In some cases, a subject nucleotide sequence encoding a selectable marker protein (e.g., a drug selectable marker protein) includes 4 or more (e.g., 5 or more, 6 or more, 7 or more, 8 or more, 9 or more, or 10 or more, 12 or more, 14 or more, 16 or more, 18 or more, 20 or more, 22 or more, 24 or more, or 26 or more) Poly T tracts, each of which have from 3 to 6 consecutive T nucleotides. In some cases, a subject nucleotide sequence encoding a selectable marker protein (e.g., a drug selectable marker protein) includes 10 or more (e.g., 11 or more, 12 or more, 14 or more, 16 or more, 18 or more, 20 or more, 22 or more, 24 or more, or 26 or more) Poly T tracts, each of which have from 3 to 6 consecutive T nucleotides. (see Table 8).

In some cases, a subject nucleotide sequence encoding a selectable marker protein (e.g., a drug selectable marker protein) includes 4 or more (e.g., 5 or more, 6 or more, 7 or more, 8 or more, 9 or more, or 10 or more, 12 or more, 14 or more, 16 or more, 18 or more, or 20 or more) Poly A tracts, each of which have from 3 to 5 consecutive A nucleotides. In some cases, a subject nucleotide sequence encoding a selectable marker protein (e.g., a drug selectable marker protein) includes 11 or more (e.g., 12 or more, 14 or more, 16 or more, 18 or more, or 20 or more) Poly A tracts, each of which have from 3 to 5 consecutive A nucleotides. (see Table 8).

In some cases, a subject nucleotide sequence encoding a selectable marker protein (e.g., a drug selectable marker protein) includes 7 or more (e.g., 8 or more, 9 or more, or 10 or more, 12 or more, 14 or more, 16 or more, 18 or more, 20 or more, 22 or more, 24 or more, 26 or more, 28 or more, 30 or more, 32 or more, 34 or more, 36 or more, 38 or more, or 40 or more) Poly-A/poly-T tracts, each of which have from 3 to 6 consecutive A or T nucleotides. In some cases, a subject nucleotide sequence encoding a selectable marker protein (e.g., a drug selectable marker protein) includes 20 or more (e.g., 22 or more, 24 or more, 26 or more, 28 or more, 30 or more, 32 or more, 34 or more, 36 or more, 38 or more, or 40 or more) Poly-A/poly-T tracts, each of which have from 3 to 6 consecutive A or T nucleotides. (see Table 8).

In some cases, a subject nucleotide sequence encoding a selectable marker protein (e.g., a drug selectable marker protein) includes 4 or more (e.g., 5 or more, 6 or more, 7 or more, 8 or more, 9 or more, or 10 or more) Poly T tracts, each of which have from 4 to 6 consecutive T nucleotides. In some cases, a subject nucleotide sequence encoding a selectable marker protein (e.g., a drug selectable marker protein) includes 8 or more (e.g., 9 or more, 10 or more, 11 or more, or 12 or more) Poly T tracts, each of which have from 4 to 6 consecutive T nucleotides. In some cases, a subject nucleotide sequence encoding a selectable marker protein (e.g., a drug selectable marker protein) includes 4 or more (e.g., 5 or more, or 6 or more) Poly A tracts, each of which have from 4 to 5 consecutive A nucleotides. (see Table 8).

In some cases, a subject nucleotide sequence encoding a selectable marker protein (e.g., a drug selectable marker protein) includes 4 or more (e.g., 5 or more, 6 or more, 7 or more, 8 or more, 9 or more, 10 or more, 11 or more, 12 or more, 13 or more, 14 or more, 15 or more, or 16 or more) Poly-A/poly-T tracts, each of which have from 4 to 6 consecutive A or T nucleotides. In some cases, a subject nucleotide sequence encoding a selectable marker protein (e.g., a drug selectable marker protein) includes 10 or more (e.g., 11 or more, 12 or more, 13 or more, 14 or more, 15 or more, or 16 or more) Poly-A/poly-T tracts, each of which have from 4 to 6 consecutive A or T nucleotides. (see Table 8).

In some cases, a subject nucleotide sequence encoding a selectable marker protein (e.g., a drug selectable marker protein) includes 4 or more (e.g., 5 or more, 6 or more, or 7 or more) Poly T tracts, each of which have 5 or 6 consecutive T nucleotides. In some cases, a subject nucleotide sequence encoding a selectable marker protein (e.g., a drug selectable marker protein) includes one or more Poly A tracts, each of which have 5 consecutive A nucleotides. In some cases, a subject nucleotide sequence encoding a selectable marker protein (e.g., a drug selectable marker protein) includes 4 or more (e.g., 5 or more, 6 or more, 7 or more, or 8 or more) Poly-A/poly-T tracts, each of which have 5 or 6 consecutive A or T nucleotides. (see Table 8).

TABLE 8

Poly-A/Poly-T tracts present in the Kan, Amp, and Tet genes of Table 1. (Also see working examples below)

| | Amp-1 | Amp-2 | J-Amp | Kan-1 | Kan-2 | J-Kan | JT-Kan | Tet | J-Tet |
|---|---|---|---|---|---|---|---|---|---|
| TTT | 9 | 20 | 22 | 3 | 26 | 25 | 20 | 8 | 46 |
| TTTT | 7 | 8 | 12 | 2 | 5 | 9 | 13 | 1 | 21 |

TABLE 8-continued

Poly-A/Poly-T tracts present in the Kan, Amp, and Tet genes of Table 1. (Also see working examples below)

| | Amp-1 | Amp-2 | J-Amp | Kan-1 | Kan-2 | J-Kan | JT-Kan | Tet | J-Tet |
|---|---|---|---|---|---|---|---|---|---|
| TTTTT | 3 | 4 | 4 | 1 | 4 | 6 | 7 | 0 | 6 |
| TTTTTT | 2 | 1 | 2 | 0 | 1 | 1 | 1 | 0 | 2 |
| TTTTTTT | 0 | 0 | 1 | 0 | 1 | 0 | 1 | 0 | 1 |
| TTTTTTTT | 0 | 0 | 0 | 0 | 0 | 0 | 0 | 0 | 1 |
| AAA | 10 | 18 | 20 | 3 | 7 | 8 | 0 | 2 | 6 |
| AAAA | 2 | 4 | 4 | 1 | 4 | 5 | 0 | 0 | 1 |
| AAAAA | 0 | 1 | 1 | 0 | 1 | 1 | 0 | 0 | 1 |
| AAAAAA | 0 | 0 | 0 | 0 | 0 | 0 | 0 | 0 | 0 |

Note:
the shorter sequences (the row above) are embedded in the longer sequences (the row below). For example, "Amp-2" has 20 total Poly-T tracts between 3 and 6 nucleotides in length (1 of them is 6 nt, 3 of them are 5 nt, 4 of them are 4 nt, and 12 of them are 3 nt). In other words, 'TTT' means there are x number of tracts having 3 or more Ts, while 'TTTT' means there are x number of tracts having 4 or more Ts, etc.

Polymerase II (Pol II) Pause Site

A Polymerase II (Pol II) pause site is a nucleotide sequence at which Pol II pauses during transcription. In some cases, a subject non silencing selectable maker gene includes a nucleotide sequence (e.g., a nucleotide sequence encoding a selectable marker protein such as a drug selectable marker protein) that does not have a Pol II pause site (see Table 9). In some cases, a subject non silencing selectable maker gene includes a nucleotide sequence (e.g., a nucleotide sequence encoding a selectable marker protein such as a drug selectable marker protein) having a Pol II pause site (see Table 9). Examples of potential Pol II pause sites include, but are not limited to: AATAAA; AATAA; TTTATT; TTATT; TTTTTTTCCCTTTTTT (SEQ ID NO: 17); and AAAAAAGGGAAAAAA (SEQ ID NO: 18).

In some cases, a subject non silencing selectable maker gene includes a nucleotide sequence (e.g., a nucleotide sequence encoding a selectable marker protein such as a drug selectable marker protein) having 5 or fewer Pol II pause sites (e.g., 4 or fewer, 3 or fewer, 2 or fewer, or 1 or fewer Pol II pause sites). In some cases, a subject non silencing selectable maker gene includes a nucleotide sequence (e.g., a nucleotide sequence encoding a selectable marker protein such as a drug selectable marker protein) that does not have a Pol II pause site.

In some cases, a Pol II pause site includes any of the following sequences: AATAAA; AATAA; TTTATT; TTATT; TTTTTTTCCCTTTTTT (SEQ ID NO: 17); or AAAAAAGGGAAAAAA (SEQ ID NO: 18). As such, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; TTTATT; TTATT; TTTTTTTCCCTTTTTT (SEQ ID NO: 17); and AAAAAAGGGAAAAAA (SEQ ID NO: 18). In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of any of the following sequences: AATAAA; AATAA; TTTATT; TTATT; TTTTTTTCCCTTTTTT (SEQ ID NO: 17); and AAAAAAGGGAAAAAA (SEQ ID NO: 18).

In some cases, a Pol II pause site includes any of the following sequences: AATAAA; AATAA; TTTATT; TTTTTTTCCCTTTTTT (SEQ ID NO: 17); and AAAAAAGGGAAAAAA (SEQ ID NO: 18). As such, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; TTTATT; TTTTTTTCCCTTTTTT (SEQ ID NO: 17); and AAAAAAGGGAAAAAA (SEQ ID NO: 18). In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of the sequence TTATT. As such, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; TTTATT; TTTTTTTCCCTTTTTT (SEQ ID NO: 17); and AAAAAAGGGAAAAAA (SEQ ID NO: 18); and has 5 or fewer instances (e.g., 4 or fewer, 3 or fewer, 2 or fewer, 1 or fewer, or no instances) of the sequence TTATT. For example, in some cases, a subject non silencing selectable maker gene includes a nucleotide sequence (e.g., a nucleotide sequence encoding a selectable marker protein such as a drug selectable marker protein) having 2 or fewer instances (e.g., 1 or fewer, or no instances) of the sequence TTATT. As such, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; TTTATT; TTTTTTTCCCTTTTTT (SEQ ID NO: 17); and AAAAAAGGGAAAAAA (SEQ ID NO: 18); and has 2 or fewer instances (e.g., 1 or fewer, or no instances) of the sequence TTATT.

In some cases, a subject non silencing selectable maker gene includes a nucleotide sequence (e.g., a nucleotide sequence encoding a selectable marker protein such as a drug selectable marker protein) that does not have any of the following sequences: AATAAA; TTTATT; TTTTTTTCCCTTTTTT (SEQ ID NO: 17); and AAAAAAGGGAAAAAA (SEQ ID NO: 18). In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of any of the following sequences: AATAA and TTATT. As such, in some cases, a subject non silencing selectable maker gene includes a nucleotide sequence (e.g., a nucleotide sequence encoding a selectable marker protein such as a drug selectable marker protein) that does not have any of the following sequences: AATAAA, TTTATT, TTTTTTTCCCTTTTTT (SEQ ID NO: 17), and AAAAAAGGGAAAAAAA (SEQ ID NO: 18); and has 5 or fewer instances (e.g., 4 or fewer, 3 or fewer, 2 or fewer, 1 or fewer, or no instances) of either of the sequences: TTATT and AATAA. For example, in some cases, a subject non silencing selectable maker gene includes a nucleotide sequence (e.g., a nucleotide sequence encoding a selectable marker protein such as a drug selectable marker protein) having 2 or fewer instances (e.g., 1 or fewer, or no instances) of any of the following sequences: AATAA and TTATT. As such, in some cases, a subject non silencing selectable maker gene includes a nucleotide sequence (e.g., a nucleotide sequence encoding a selectable marker protein such as a drug selectable marker protein) that does not have any of the following sequences: AATAAA, TTTATT, TTTTTTTCCCTTTTTT (SEQ ID NO: 17), and AAAAAAGGGAAAAAAA (SEQ ID NO: 18); and has 2 or fewer instances (e.g., 1 or fewer, or no instances) of either of the sequences: TTATT and AATAA.

In some cases, a Pol II pause site includes any of the following sequences: TTTATT; TTTTTTTCCCTTTTTT (SEQ ID NO: 17); and AAAAAAGGGAAAAAAA (SEQ ID NO: 18). As such, in some cases, a subject non silencing selectable maker gene includes a nucleotide sequence (e.g., a nucleotide sequence encoding a selectable marker protein such as a drug selectable marker protein) that does not have any of the following sequences: TTTATT; TTTTTTTCCCTTTTTT (SEQ ID NO: 17); and AAAAAAGGGAAAAAAA (SEQ ID NO: 18). In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of the sequence TTATT. As such, in some cases, a subject non silencing selectable maker gene includes a nucleotide sequence (e.g., a nucleotide sequence encoding a selectable marker protein such as a drug selectable marker protein) that does not have any of the following sequences: TTTATT; TTTTTTTCCCTTTTTT (SEQ ID NO: 17); and AAAAAAGGGAAAAAAA (SEQ ID NO: 18); and has 5 or fewer instances (e.g., 4 or fewer, 3 or fewer, 2 or fewer, 1 or fewer, or no instances) of the sequence TTATT. For example, in some cases, a subject non silencing selectable maker gene includes a nucleotide sequence (e.g., a nucleotide sequence encoding a selectable marker protein such as a drug selectable marker protein) having 2 or fewer instances (e.g., 1 or fewer, or no instances) of the sequence TTATT. As such, in some cases, a subject non silencing selectable maker gene includes a nucleotide sequence (e.g., a nucleotide sequence encoding a selectable marker protein such as a drug selectable marker protein) that does not have any of the following sequences: TTTATT; TTTTTTTCCCTTTTTT (SEQ ID NO: 17); and AAAAAAGGGAAAAAAA (SEQ ID NO: 18); and has 2 or fewer instances (e.g., 1 or fewer, or no instances) of the sequence TTATT.

In some cases, a Pol II pause site includes any of the following sequences: AATAAA; AATAA; TTTATT; and TTATT. As such, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; TTTATT; and TTATT. In some cases, a subject non silencing selectable maker gene includes a nucleotide sequence (e.g., a nucleotide sequence encoding a selectable marker protein such as a drug selectable marker protein) that includes 5 or fewer instances (e.g., 4 or fewer, 3 or fewer, 2 or fewer, 1 or fewer, or no instances) of any of the following sequences: AATAAA; AATAA; TTTATT; and TTATT. For example, in some cases, a subject non silencing selectable maker gene includes a nucleotide sequence (e.g., a nucleotide sequence encoding a selectable marker protein such as a drug selectable marker protein) that includes 2 or fewer instances (e.g., 1 or fewer, or no instances) of any of the following sequences: AATAAA; AATAA; TTTATT; and TTATT.

In some cases, a Pol II pause site includes any of the following sequences: AATAAA; AATAA; and TTTATT. As such, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; and TTTATT. In some cases, a subject non silencing selectable maker gene includes a nucleotide sequence (e.g., a nucleotide sequence encoding a selectable marker protein such as a drug selectable marker protein) that includes 5 or fewer instances (e.g., 4 or fewer, 3 or fewer, 2 or fewer, 1 or fewer, or no instances) of any of the following sequences: AATAAA; AATAA; and TTTATT. As such, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; and TTTATT; and has 5 or fewer instances (e.g., 4 or fewer, 3 or fewer, 2 or fewer, 1 or fewer, or no instances) of the sequence TTATT. For example, in some cases, a subject non silencing selectable maker gene includes a nucleotide sequence (e.g., a nucleotide sequence encoding a selectable marker protein such as a drug selectable marker protein) that does not have any of the following sequences: AATAAA; AATAA; and TTTATT; and has 2 or fewer instances (e.g., 1 or fewer, or no instances) of the sequence TTATT.

In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of the following sequence: AATAAA. In some cases, a subject non silencing selectable maker gene includes a nucleotide sequence (e.g., a nucleotide sequence encoding a selectable marker protein such as a drug selectable marker protein) that does not include the following sequence: AATAAA.

In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of the following sequence: AATAA. In some cases, a subject non silencing selectable maker gene includes a nucleotide sequence (e.g., a nucleotide sequence encoding a selectable marker protein such as a drug selectable marker protein) that does not include the following sequence: AATAA.

In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of the following sequence: TTTATT. In some cases, a subject non silencing selectable maker gene includes a nucleotide sequence (e.g., a nucleotide sequence encoding a selectable marker protein such as a drug selectable marker protein) that does not include the following sequence: TTT-ATT.

In some cases, a subject non silencing selectable maker gene includes a nucleotide sequence (e.g., a nucleotide sequence encoding a selectable marker protein such as a drug selectable marker protein) having 5 or fewer instances (e.g., 4 or fewer, 3 or fewer, 2 or fewer, 1 or fewer, or no instances) of the following sequence: TTATT. For example, in some cases, a subject non silencing selectable maker gene includes a nucleotide sequence (e.g., a nucleotide sequence encoding a selectable marker protein such as a drug selectable marker protein) having 2 or fewer instances (e.g., 1 or fewer, or no instances) of the following sequence: TTATT. In some cases, a subject non silencing selectable maker gene includes a nucleotide sequence (e.g., a nucleotide sequence encoding a selectable marker protein such as a drug selectable marker protein) that does not include the following sequence: TTATT.

In some cases, a subject non silencing selectable maker gene includes a nucleotide sequence (e.g., a nucleotide sequence encoding a selectable marker protein such as a drug selectable marker protein) that does not include the following sequence: TTTTTTTCCCTTTTTT (SEQ ID NO: 17). In some cases, a subject non silencing selectable maker gene includes a nucleotide sequence (e.g., a nucleotide sequence encoding a selectable marker protein such as a drug selectable marker protein) that does not include the following sequence: AAAAAAGGGAAAAAAA (SEQ ID NO: 18). In some cases, a subject non silencing selectable maker gene includes a nucleotide sequence (e.g., a nucleotide sequence encoding a selectable marker protein such as a drug selectable marker protein) that does not include either of the following sequences: TTTTTTTCCCTTTTTT (SEQ ID NO: 17) and AAAAAAGGGAAAAAAA (SEQ ID NO: 18).

cell type (e.g., prokaryotic cells, eukaryotic cells). In some embodiments, a subject expression cassette includes a transgene that is operably linked to a promoter (e.g., functional in eukaryotic cells). By "transgene" it is meant any polynucleotide sequence that encodes a peptide/polypeptide or a non-translated ribonucleic acid (non-coding RNA, ncRNA), e.g. a double stranded RNA or a single stranded RNA, e.g., antisense RNA, sRNA, shRNA, miRNA, and the like. In some cases (e.g., in some cases where the vector is a plasmid), a subject expression vector includes an origin of replication (e.g., a bacterial origin of replication). A subject expression vector may be prepared in any convenient way, e.g., using standard molecular biology techniques.

In some cases, the expression cassette of a subject expression vector includes an insertion site (e.g., an insertion sequence) for the insertion of a transgene of interest, where the insertion site is operably linked to a promoter (e.g., a promoter functional in eukaryotic cells such as mammalian cells, human cells, etc.), such that once a transgene is inserted, the transgene will be operably linked to the promoter. Any convenient insertion sequence can be used (e.g., a multiple cloning site, a site for insertion via an integrase, a site for insertion via CRISPR/Cas9 technology, and the like). In some cases, the expression cassette of a subject expression vector does not include a transgene, but instead includes an insertion site (e.g., for the insertion of a transgene of interest) that is operably linked to a promoter (e.g., one that is functional in eukaryotic cells). In other words, the insertion site is operably linked to the promoter such that once a nucleotide sequence (e.g. of a transgene of interest) is inserted at the insertion site, the inserted transgene will be operably linked to the promoter.

In some embodiments, a subject expression vector includes: (a) an expression cassette (e.g., having an insertion site and/or transgene that is operably linked to a promoter functional in a eukaryotic cell); and (b) a non silencing selectable marker gene that provides for selection (e.g.,

TABLE 9

Pol II pause sites present in the Kan and Amp genes of Table 1. (Also see working examples below)

| | Amp-1 | Amp-2 | J-Amp | Kan-1 | Kan-2 | J-Kan | JT-Kan | Tet | J-Tet |
|---|---|---|---|---|---|---|---|---|---|
| AATAAA | — | — | — | — | — | — | — | — | — |
| AATAA | — | — | — | — | — | — | — | — | — |
| TTTATT | 1 | 1 | — | — | 3 | — | 1 | — | — |
| TTATT | +1 | +4 | — | — | +4 | +2 | +0 | — | — |
| TTTTTTTCCCTTTTTT | — | — | — | — | — | — | — | — | — |
| AAAAAAGGGAAAAAAA | — | — | — | — | — | — | — | — | — |

Note:
The "+" refers to the fact that the sequence in this row (TTATT) is a subset of the sequence of the row above (TTTATT). Thus, the number after the "+" denotes how many new instances are added when considering only the subset sequence. For example, "Kan-2" has 7 TTATT sequences, but 3 of them are also TTTATT sequences; while "Amp-2" has 5 TTATT sequences, but 1 of them is also a TTTATT sequence. As another example, "J-Kan" has 2 TTATT sequences, but no TTTATT sequences; while "J-Amp" has no TTATT and no TTTATT sequences.

Expression Vectors

Provided are expression vectors. A subject expression vector includes an expression cassette and a non silencing selectable marker gene (as described in detail above). As noted above, by "vector" it is meant a nucleic acid, e.g., a linear nucleic acid, a circular nucleic acid, a phage, a virus, a cosmid, and the like, that is capable of transferring a polynucleotide sequence to target cells. Also as noted above, an expression cassette includes a first nucleic acid sequence operably linked to a promoter that is functional in a desired provides drug resistance for prokaryotic cells), where the non silencing selectable marker gene includes a nucleotide sequence that (i) encodes a selectable marker protein (e.g., a drug selectable marker protein); (ii) is operably linked to a promoter functional in a desired cell type (e.g., prokaryotic cells), and (iii) includes an increased A/T content relative to a corresponding wild type nucleotide sequence.

In some embodiments, a subject expression vector includes: (a) an expression cassette (e.g., having an insertion site and/or transgene that is operably linked to a promoter functional in a eukaryotic cell); and (b) a non silencing selectable marker gene that provides for selection (e.g., provides drug resistance for prokaryotic cells), where the non silencing selectable marker gene includes a nucleotide sequence that (i) encodes a selectable marker protein (e.g., a drug selectable marker protein); (ii) is operably linked to a promoter functional in a desired cell type (e.g., prokaryotic cells), and (iii) has an A/T content in a range of from 52% to 70%.

In some cases, the non silencing selectable marker gene of a subject expression vector includes a nucleotide sequence that encodes a drug selectable marker protein. In some cases, the drug selectable marker protein can provide resistance for prokaryotic cells to one or more drugs selected from: kanamycin, neomycin, ampicillin, carbenicillin, chloramphenicol, gentamicin, tetracycline, rifampin, trimethoprim, hygromycin B, and spectinomycin. For example, in some cases, the drug selectable marker protein can provide resistance for prokaryotic cells to kanamycin. In some cases, the drug selectable marker protein can provide resistance for prokaryotic cells to ampicillin.

In some cases, a subject expression vector has two or more (e.g., 3 or more, 4 or more) non silencing selectable marker genes, where each has a nucleotide sequence that encodes a selectable marker protein (e.g., a drug selectable marker protein) that is different than the other. In some cases, a subject expression vector has two non silencing selectable marker genes, where each has a nucleotide sequence that encodes a selectable marker protein (e.g., a drug selectable marker protein) that is different than the other. In some cases, a subject expression vector has 3 non silencing selectable marker genes, where each has a nucleotide sequence that encodes a selectable marker protein (e.g., a drug selectable marker protein) that is different than the other. In some cases, a subject expression vector has 4 non silencing selectable marker genes, where each has a nucleotide sequence that encodes a selectable marker protein (e.g., a drug selectable marker protein) that is different than the other.

For example, in some cases, a subject expression vector has (i) a first non silencing selectable marker gene having a nucleotide sequence that encodes for a drug selectable marker protein that provides resistance to a first drug; and (ii) a second non silencing selectable marker gene having a nucleotide sequence that encodes for a drug selectable marker protein that provides resistance to a second drug (e.g., where each of the first and second drugs are selected from: kanamycin, neomycin, ampicillin, carbenicillin, chloramphenicol, gentamicin, tetracycline, rifampin, trimethoprim, hygromycin B, and spectinomycin). In some cases, a subject expression vector has (i) a first non silencing selectable marker gene having a nucleotide sequence that encodes for a drug selectable marker protein that provides resistance to a first drug; (ii) a second non silencing selectable marker gene having a nucleotide sequence that encodes for a drug selectable marker protein that provides resistance to a second drug; and (iii) a third non silencing selectable marker gene having a nucleotide sequence that encodes for a drug selectable marker protein that provides resistance to a third drug (e.g., where each of the first, second, and third drugs are selected from: kanamycin, neomycin, ampicillin, carbenicillin, chloramphenicol, gentamicin, tetracycline, rifampin, trimethoprim, hygromycin B, and spectinomycin).

As an illustrative example, in some cases, a subject expression vector (amp/kan) has (i) a first non silencing selectable marker gene having a nucleotide sequence that encodes for a drug selectable marker protein that provides resistance to kanamycin; and (ii) a second non silencing selectable marker gene having a nucleotide sequence that encodes for a drug selectable marker protein that provides resistance to ampicillin. In some cases, a subject expression vector (kan/chlor) has (i) a first non silencing selectable marker gene having a nucleotide sequence that encodes for a drug selectable marker protein that provides resistance to kanamycin; and (ii) a second non silencing selectable marker gene having a nucleotide sequence that encodes for a drug selectable marker protein that provides resistance to chloramphenicol. In some cases, a subject expression vector (amp/chlor) has (i) a first non silencing selectable marker gene having a nucleotide sequence that encodes for a drug selectable marker protein that provides resistance to ampicillin; and (ii) a second non silencing selectable marker gene having a nucleotide sequence that encodes for a drug selectable marker protein that provides resistance to chloramphenicol. In some cases, a subject expression vector (amp/kan/chlor) has (i) a first non silencing selectable marker gene having a nucleotide sequence that encodes for a drug selectable marker protein that provides resistance to kanamycin; (ii) a second non silencing selectable marker gene having a nucleotide sequence that encodes for a drug selectable marker protein that provides resistance to ampicillin; and (iiii) a third non silencing selectable marker gene having a nucleotide sequence that encodes for a drug selectable marker protein that provides resistance to chloramphenicol.

As another illustrative example, in some cases, a subject expression vector (kan/tet) has (i) a first non silencing selectable marker gene having a nucleotide sequence that encodes for a drug selectable marker protein that provides resistance to kanamycin; and (ii) a second non silencing selectable marker gene having a nucleotide sequence that encodes for a drug selectable marker protein that provides resistance to tetracycline. In some cases, a subject expression vector (amp/tet) has (i) a first non silencing selectable marker gene having a nucleotide sequence that encodes for a drug selectable marker protein that provides resistance to ampicillin; and (ii) a second non silencing selectable marker gene having a nucleotide sequence that encodes for a drug selectable marker protein that provides resistance to tetracycline. In some cases, a subject expression vector (amp/kan/tet) has (i) a first non silencing selectable marker gene having a nucleotide sequence that encodes for a drug selectable marker protein that provides resistance to kanamycin; (ii) a second non silencing selectable marker gene having a nucleotide sequence that encodes for a drug selectable marker protein that provides resistance to ampicillin; and (iiii) a third non silencing selectable marker gene having a nucleotide sequence that encodes for a drug selectable marker protein that provides resistance to tetracycline.

By a promoter it is meant an untranslated sequences located upstream (5) to the start codon of a structural gene (generally within about 100 to 1000 bp) that modulates the transcription of a particular nucleic acid sequence to which they are operably linked. By modulating transcriptional activation, it is meant that transcription will be modulated, e.g. increased, from basal levels in the target cell by at least about 10 fold, by at least about 100 fold, more usually by at least about 1000 fold. Such promoters typically fall into two classes, inducible and constitutive. Inducible promoters are promoters that initiate increased levels of transcription from DNA under their control in response to some change in culture conditions, e.g., the presence or absence of a nutrient, drug, change in temperature, or change in expression of a protein in a cell, e.g. the tetracycline-inducible promoters. Constitutive, or ubiquitously acting, promoters are always active, e.g. the CMV-β-actin promoter/enhancer. A large number of promoters recognized by a variety of potential host cells are well known. Both a native promoter sequence and many heterologous promoters may be used to direct expression of transgene of interest. Any convenient promoter can be used.

Transcription by higher eukaryotes of transgenes in expression cassettes may be increased by inserting an enhancer sequence into the vector. Enhancers are cis-acting elements of DNA, usually about from 10 to 300 bp, which act on a promoter to increase its transcription. Enhancers are relatively orientation- and position-independent, having been found 5' and 3' to the transcription unit, within an intron, as well as within the coding sequence itself.

Expression cassettes can include sequences necessary for the termination of transcription and/or for stabilizing the transgene (e.g., the RNA that is transcribed). Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding the transgene of interest.

In some cases, a subject expression vector provides for the persistent, high level expression of a transgene (transgene of interest) in a desired cell type (e.g., eukaryotic cells, mammalian cells, human cells). By high level expression, it is meant that the transgene is expressed by a host cell at a level that is 50-fold greater, 100-fold (2-log) greater, 1000-fold (3-log) greater, or 10,000 fold (4-log) greater or more, within the first 1, 2, or 3 days following introduction into a cell than in the absence of vector. By persistent, it is meant that high level expression of the transgene persists for 2 weeks or more, for example, 3 weeks or more (e.g., 4 weeks or more, 5 weeks or more, 6 weeks or more, 7 weeks or more, 8 weeks or more, 9 weeks or more, 10 weeks or more, 12 weeks or more, 18 weeks or more, or 6 months or more). In other words, the expression level of the transgene does not decrease more than 100-fold, more usually not more than 50-fold, in some instances, not more than 10-fold in the 2 weeks or more (e.g., 3 weeks or more, 4 weeks or more, 5 weeks or more, 6 weeks or more, 7 weeks or more, 8 weeks or more, 9 weeks or more, 10 weeks or more, 12 weeks or more, 18 weeks or more, or 6 months or more) following introduction into a cell from levels observed within the first 1, 2, or 3 days.

In some instances, a subject expression vector is a linear nucleic acid vector. In other instances, a subject expression vector is a a circular nucleic acid. In some instances, a subject expression vector may be maintained extrachromosomally, or "episomally" in the target cell, i.e., as a linear or circular nucleic acid that does not integrate into the target cell genome. For example, a subject expression vector may be created by modifying a non-integrating vector, e.g. a non-integrating recombinant viral vector, e.g. a recombinant adenovirus or recombinant cytomegalovirus. In other instances, a subject expression vector may integrate into the genome of the host, i.e., as a linear or circular nucleic acid that integrates into the host genome. For example, a subject expression vector may be created by modifying an integrating vector, e.g. a transposon-based vector (e.g. the Sleeping Beauty vector), or an integrating recombinant viral vector, e.g. a retrovirus, e.g. a recombinant lentivirus or phage. By a "recombinant virus" or a "recombinant viral vector", it is meant a virus, e.g. of the genus adenoviridiae, cytomegaloviridiae, lentivirus, that is capable of infecting a cell whose viral genome has been modified through conventional recombinant DNA techniques. Non-limiting examples of recombinant viruses that are commonly used in the art to transfer genes of interest into a target cell, e.g. in gene therapy, include recombinant adenoviruses ("Ad", or "Adv"), e.g. Ad2 and Ad5, as described for example in Curiel, D T and Douglas J T (2002) Adenoviral Vectors for Gene Therapy (Elsevier Inc.); recombinant adeno-associated viruses ("AAV"), e.g. AAV1, AAV2, AAV3, AAV4, AAV5, AAV6, AAV7, AAV8, AAV9, AAV10, AAV11, and AAV12, as described for example in Flotte, T R and Berns, K I. (2005) Adeno-associated viral vectors for gene therapy (Elsevier B.V.); and recombinant lentiviral vectors, as described for example in Trono, D (2003) Lentiviral Vectors, Vol. 261. (New York: Springer-Verlag). Methods of modifying, packaging, and purifying these and other recombinant viral vectors are well known in the art, see, e.g., Curiel and Douglas, supra; Flotte and Berns, supra; Trono, supra, and Machida (2003) Viral Vectors for Gene Therapy: Methods and Protocols. (NewJersey: Humana Press Inc.), the full disclosures of which are incorporated herein by reference.

Methods

Transgene expression from a subject expression vector finds use in many applications, including therapeutic applications such as in gene therapy; synthesis applications such as in the synthesis of peptides, proteins, and RNAs, e.g. for research or therapeutic purposes; and research applications, such as in the production of transgenic cells and animals.

In some embodiments, a subject expression vector is employed to express one or more transgenes (i.e., "a transgene") in cells in vitro (e.g. for research purposes or for the synthesis of transgene product in vitro), in cells ex vivo (e.g., to produce genetically modified cells that can be reintroduced into an individual or can be used to characterize and/or diagnose a disease status, etc.), and/or cells in vivo. Cells may be mitotic cells or post-mitotic cells, and include such cells of interest as pluripotent stem cells, e.g. ES cells, iPS cells, and embryonic germ cells; and somatic cells, e.g. fibroblasts, hematopoietic cells, neurons, muscle cells, bone cells, vascular endothelial cells, gut cells, and the like, and their lineage-restricted progenitors and precursors. Cells may be from any eukaryote, e.g., any mammalian species (e.g. murine, rodent, canine, feline, equine, bovine, ovine, primate, human, etc). Cells may be from established cell lines or they may be primary cells, where "primary cells", "primary cell lines", and "primary cultures" are used interchangeably herein to refer to cells and cells cultures that have been derived from a subject and allowed to grow in vitro for a limited number of passages, i.e. splittings, of the culture. For example, primary cultures are cultures that may have been passaged 0 times, 1 time, 2 times, 4 times, 5 times, 10 times, or 15 times, but not enough times go through the crisis stage. Typically, primary cell lines are maintained for fewer than 10 passages in vitro.

If the cells are primary cells, they may be harvest from an individual by any convenient method. For example, cells, e.g. blood cells, e.g. leukocytes, may be harvested by apheresis, leukocytopheresis, density gradient separation, etc. As another example, cells, e.g. skin, muscle, bone marrow, spleen, liver, pancreas, lung, intestine, stomach tissue, etc. may be harvested by biopsy. An appropriate solution may be used for dispersion or suspension of the harvested cells. Such solution will generally be a balanced salt solution, e.g. normal saline, PBS, Hank's balanced salt solution, etc., conveniently supplemented with fetal calf serum or other naturally occurring factors, in conjunction with an acceptable buffer at low concentration, generally from 5-25 mM. Convenient buffers include HEPES, phosphate buffers, lactate buffers, etc. The cells may be used immediately, or they may be stored, frozen, for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

In some cases, a subject method includes introducing a subject expression vector into a cell. A subject expression vector may be introduced into a cell using any convenient method. For example, an expression vector can be provided directly to cells, e.g., the target cells can be contacted with a subject expression vector such that the vector is taken up by the cells. Methods for introducing nucleic acid vectors into cells, such as electroporation, calcium chloride transfection, lipofection, injection, and infection, are well known in the art. For example, a circular or linear subject expression vector may be introduced into a target cell by formulating the vector into liposomes using an agent such as lipofectamine and contacting the cells with the liposomes ("lipofection"). As another example, a circular or linear subject expression vector may be electroporated into a target cell by contacting the cell with the expression vector and applying an electrical field to increase the permeability of the cell membrane. As another example, a viral subject expression vector may be introduced into a target cell by infecting the cell with viral particles comprising the expression vector. Typically, such viral particles are prepared by growing the vector in a packaging cell line, and purifying viral particles comprising the expression vector packaged into viral capsids by the packaging cell line. Recombinant viruses, e.g. adenoviruses, cytomegaloviruses, retroviruses, etc., cell lines useful for their packaging into capsids, methods of introducing a subject viral expression vector into packaging cell lines, methods of collecting the viral particles that are generated by the packaging lines, and methods of infecting cells with viral particles in vitro or in vivo are well known in the art.

A subject expression vector can be provided to cells for about 30 minutes to about 24 hours, e.g., 1 hour, 1.5 hours, 2 hours, 2.5 hours, 3 hours, 3.5 hours 4 hours, 5 hours, 6 hours, 7 hours, 8 hours, 12 hours, 16 hours, 18 hours, 20 hours, or any other period from about 30 minutes to about 24 hours, which may be repeated with a frequency of about every day to about every 4 days, e.g., every 1.5 days, every 2 days, every 3 days, or any other frequency from about every day to about every four days. A subject expression vector may be provided to cells one or more times, e.g. one time, twice, three times, or more than three times, and the cells allowed to incubate with the expression vector for some amount of time following each contacting event e.g. 16-24 hours, after which time the media is replaced with fresh media and the cells are cultured further.

In cases in which two or more different transgenes are introduced into a cell, i.e. a cocktail of transgenes, the transgenes may be provided simultaneously, e.g. as part of two or more separate expression vectors delivered simultaneously, or as a single expression vector that includes the two or more transgenes. Alternatively, they may be provided consecutively, e.g. the first transgene being provided on a first expression vector, followed by the second transgene on a second expression vector, etc. or vice versa.

In some cases, a subject expression vector is provided to the cells (introduced into the cells) in an amount effective to induce expression of the transgene in the cells. By an effective amount of expression vector, it is meant the amount to induce a 10-fold increase or more in the level of transgene expression observed relative to a negative control, e.g. a cell contacted with an empty vector, i.e. an expression vector that does not include the transgene. That is to say, an effective amount or dose of expression vector will induce a 10-fold increase, a 20-fold increase, a 50-fold increase or more in the amount of expression of a transgenic sequence observed, in some instances a 100-fold (2 log) increase, a 500-fold increase or more, sometimes a 1000-fold (3 log) or 10,000-fold (4 log) increase or more in the amount of expression observed. The amount of expression may be measured by any convenient method, for example, Northern blot, Western blot, ELISA, FACS (fluorescence activated cell sorting), in situ hybridization, array, etc.

Introducing an expression vector into cells may occur in any culture media and under any culture conditions that promote the survival of the cells. For example, cells may be suspended in any appropriate nutrient medium that is convenient, such as Iscove's modified DMEM or RPMI 1640, supplemented with fetal calf serum or heat inactivated goat serum (about 5-10%), L-glutamine, a thiol, particularly 2-mercaptoethanol, and antibiotics, e.g. penicillin and streptomycin. The culture may contain growth factors to which the cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Following the methods described above, persistent, high level expression of a transgene may be achieved in a cell vitro, ex vivo, or in vivo. In some embodiments, e.g. when the transgene encodes a selectable protein, the population of cells may be enriched for those transformed by the expression vector by separating the transformed cells from the remaining population. Separation may be by any convenient separation technique appropriate for the selectable protein used. For example, if a fluorescent marker is expressed, cells may be separated by fluorescence activated cell sorting, whereas if a cell surface marker is expressed, cells may be separated from the heterogeneous population by affinity separation techniques, e.g. magnetic separation, affinity chromatography, "panning" with an affinity reagent attached to a solid matrix, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g. propidium iodide). Any technique may be employed which is not unduly detrimental to the viability of the transformed cells.

Cell compositions that are highly enriched for transformed cells (i.e., cells having the expression vector and expressing the transgene) can be achieved in this manner. By "highly enriched", it is meant that transformed cells will be 70% or more, 75% or more, 80% or more, 85% or more, 90% or more of the cell composition, for example, about 95% or more, or 98% or more of the cell composition. In other words, the composition may be a substantially pure composition of transformed cells, i.e. comprising subject expression vectors.

Cells expressing the transgene of interest produced by the methods described herein may be used immediately. Alternatively, the cells may be frozen at liquid nitrogen temperatures and stored for long periods of time, being thawed and capable of being reused. In such cases, the cells will usually be frozen in 10% DMSO, 50% serum, 40% buffered medium, or some other such solution as is commonly used in the art to preserve cells at such freezing temperatures, and thawed in a manner as commonly known in the art for thawing frozen cultured cells.

The transformed cells may be cultured in vitro under various culture conditions. The cells may be expanded in culture, i.e. grown under conditions that promote their proliferation, and preferably maintain the subject expression vector. Culture medium may be liquid or semi-solid, e.g. containing agar, methylcellulose, etc. The cell population may be suspended in an appropriate nutrient medium, such as Iscove's modified DMEM or RPMI 1640, normally supplemented with fetal calf serum (about 5-10%), L-glutamine, a thiol, particularly 2-mercaptoethanol, and antibiotics, e.g. penicillin and streptomycin. The culture may contain growth factors to which the regulatory T cells are responsive. Growth factors, as defined herein, are molecules capable of promoting survival, growth and/or differentiation of cells, either in culture or in the intact tissue, through specific effects on a transmembrane receptor. Growth factors include polypeptides and non-polypeptide factors.

Cells that have been transformed with a subject expression vector to express a transgene of interest may be transplanted to a subject for purposes such as gene therapy, e.g. to treat a disease or as an antiviral, antipathogenic, or anticancer therapeutic, for the production of genetically modified organisms in agriculture, or for biological research. The subject may be a neonate, a juvenile, or an adult. Of particular interest are mammalian subjects. Mammalian species that may be treated with the present methods include canines and felines; equines; bovines; ovines; etc. and primates, particularly humans. Animal models, particularly small mammals, e.g. murine, lagomorpha, etc. may be used for experimental investigations.

Cells may be provided to the subject alone or with a suitable substrate or matrix, e.g. to support their growth and/or organization in the tissue to which they are being transplanted. Usually, at least $1 \times 10^3$ cells will be administered, for example $5 \times 10^3$ cells, $1 \times 10^4$ cells, $5 \times 10^4$ cells, $1 \times 10^5$ cells, $1 \times 10^6$ cells or more. The cells may be introduced to the subject via any of the following routes: parenteral, subcutaneous, intravenous, intracranial, intraspinal, intraocular, or into spinal fluid. The cells may be introduced by injection, catheter, or the like. Examples of methods for local delivery, that is, delivery to the site of injury, include, e.g. through an Ommaya reservoir, e.g. for intrathecal delivery (see e.g. U.S. Pat. Nos. 5,222,982 and 5,385,582, incorporated herein by reference); by bolus injection, e.g. by a syringe, e.g. into a joint; by continuous infusion, e.g. by cannulation, e.g. with convection (see e.g. US Application No. 20070254842, incorporated here by reference); or by implanting a device upon which the cells have been reversibly affixed (see e.g. US Application Nos. 20080081064 and 20090196903, incorporated herein by reference).

The number of administrations of treatment to a subject may vary. Introducing the transgene-expressing cells into the subject may be a one-time event; but in certain situations, such treatment may elicit improvement for a limited period of time and require an on-going series of repeated treatments. In other situations, multiple administrations of the genetically modified cells may be required before an effect is observed. The exact protocols depend upon the disease or condition, the stage of the disease and parameters of the individual subject being treated.

In some applications, a subject expression vector is employed to express transgenes in an individual (e.g., in cells of the individual) in vivo. In these in vivo embodiments, the subject expression vectors can be administered to an individual. The individual may be any mammalian species, e.g. murine, rodent, canine, feline, equine, bovine, ovine, primate, human, etc. The target cells may be mitotic cells or post-mitotic cells, and include, e.g. fibroblasts, hematopoietic cells, neurons, muscle cells, bone cells, vascular endothelial cells, gut cells, and the like, and their lineage-restricted progenitors and precursors.

Subject expression vectors may be administered to an individual by any of a number of well-known methods in the art for the administration of nucleic acids to a subject. A subject expression vector can be incorporated into a variety of formulations. More particularly, the subject expression vectors of the present disclosure can be formulated into pharmaceutical compositions by combination with appropriate pharmaceutically acceptable carriers or diluents.

Pharmaceutical preparations are compositions that include one or more subject expression vectors present in a pharmaceutically acceptable vehicle. "Pharmaceutically acceptable vehicles" may be vehicles approved by a regulatory agency of the Federal or a state government or listed in the U.S. Pharmacopeia or other generally recognized pharmacopeia for use in mammals, such as humans. The term "vehicle" refers to a diluent, adjuvant, excipient, or carrier with which a compound of the invention is formulated for administration to a mammal. Such pharmaceutical vehicles can be lipids, e.g. liposomes, e.g. liposome dendrimers; liquids, such as water and oils, including those of petroleum, animal, vegetable or synthetic origin, such as peanut oil, soybean oil, mineral oil, sesame oil and the like, saline; gum acacia, gelatin, starch paste, talc, keratin, colloidal silica, urea, and the like. In addition, auxiliary, stabilizing, thickening, lubricating and coloring agents may be used. Pharmaceutical compositions may be formulated into preparations in solid, semi-solid, liquid or gaseous forms, such as tablets, capsules, powders, granules, ointments, solutions, suppositories, injections, inhalants, gels, microspheres, and aerosols. As such, administration of the subject expression vectors can be achieved in various ways, including systemic, oral, buccal, rectal, parenteral, intraperitoneal, intradermal, transdermal, intravenous, intracheal, etc., administration. The active agent may be systemic after administration or may be localized by the use of regional administration, intramural administration, or use of an implant that acts to retain the active dose at the site of implantation. The active agent may be formulated for immediate activity or it may be formulated for sustained release.

For some conditions, particularly central nervous system conditions, it may be necessary to formulate agents to cross the blood-brain barrier (BBB). One strategy for drug delivery through the blood-brain barrier (BBB) entails disruption of the BBB, either by osmotic means such as mannitol or leukotrienes, or biochemically by the use of vasoactive substances such as bradykinin. The potential for using BBB opening to target specific agents to brain tumors is also an option. A BBB disrupting agent can be co-administered with the therapeutic compositions of the disclosure, e.g., when the compositions are administered by intravascular injection. Other strategies to go through the BBB may entail the use of endogenous transport systems, including Caveolin-1 mediated transcytosis, carrier-mediated transporters such as glucose and amino acid carriers, receptor-mediated transcytosis for insulin or transferrin, and active efflux transporters such as p-glycoprotein. Active transport moieties may also be conjugated to the therapeutic compounds for use in the invention to facilitate transport across the endothelial wall of the blood vessel. Alternatively, drug delivery of therapeutics agents behind the BBB may be by local delivery, for example by intrathecal delivery, e.g. through an Ommaya reservoir (see e.g. U.S. Pat. Nos. 5,222,982 and 5,385,582, incorporated herein by reference); by bolus injection, e.g. by a syringe, e.g. intravitreally or intracranially; by continuous infusion, e.g. by cannulation, e.g. with convection (see e.g. US Application No. 20070254842, incorporated here by reference); or by implanting a device upon which the agent has been reversibly affixed (see e.g. US Application Nos. 20080081064 and 20090196903, incorporated herein by reference).

Typically, an effective amount of a subject expression vector is provided. As discussed above with regard to ex vivo methods, an effective amount or effective dose of a subject expression vector in vivo is the amount to induce a 10 fold increase or more in the amount of expression of a transgene relative to a negative control, e.g. a cell contacted with an empty vector. The amount of expression may be measured by any convenient method, e.g. as described above and known in the art. The calculation of the effective amount or effective dose of a subject expression vector to be administered is within the skill of one of ordinary skill in the art, and will be routine to those persons skilled in the art. Needless to say, the final amount to be administered will be dependent upon the route of administration and upon the nature of the disorder or condition that is to be treated.

The effective dose of a subject expression vector for introduction into cells may be empirically determined by one of skill in the art. For example, subject expression vectors may be provided to cells at a concentration of at least about 1 ng for $10^6$ cells, about 10 ng for $10^6$ cells, about 100 ng for $10^6$ cells, about 1 µg for $10^6$ cells, about 5 µg for $10^6$ cells, or more. Typically high concentrations are not deleterious. The effective amount given to a particular patient will depend on a variety of factors, several of which will differ from patient to patient. A competent clinician will be able to determine an effective amount of a therapeutic agent to administer to a patient to halt or reverse the progression the disease condition as required. Utilizing $LD_{50}$ animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Expression vector-based therapies, i.e. preparations of subject expression vectors to be used for therapeutic administration, can be sterile. Sterility is readily accomplished by filtration through sterile filtration membranes (e.g., 0.2 µm membranes). Therapeutic compositions generally are placed into a container having a sterile access port, for example, an intravenous solution bag or vial having a stopper pierceable by a hypodermic injection needle. The expression vectors may be stored in unit or multi-dose containers, for example, sealed ampules or vials, as an aqueous solution or as a lyophilized formulation for reconstitution. As an example of a lyophilized formulation, 10-mL vials are filled with 5 ml of sterile-filtered 1% (w/v) aqueous solution of compound, and the resulting mixture is lyophilized. The infusion solution is prepared by reconstituting the lyophilized compound using bacteriostatic Water-for-Injection.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients and the like. The compositions can also include additional substances to approximate physiological conditions, such as pH adjusting and buffering agents, toxicity adjusting agents, wetting agents and detergents.

The composition can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, enhance solubility or uptake). Examples of such modifications or complexing agents include sulfate, gluconate, citrate and phosphate. The nucleic acids or polypeptides of a composition can also be complexed with molecules that enhance their in vivo attributes. Such molecules include, for example, carbohydrates, polyamines, amino acids, other peptides, ions (e.g., sodium, potassium, calcium, magnesium, manganese), and lipids.

Further guidance regarding formulations that are suitable for various types of administration can be found in Remington's Pharmaceutical Sciences, Mace Publishing Company, Philadelphia, Pa., 17th ed. (1985). For a brief review of methods for drug delivery, see, Langer, Science 249: 1527-1533 (1990).

The pharmaceutical compositions can be administered for prophylactic and/or therapeutic treatments. Toxicity and therapeutic efficacy of the active ingredient can be determined according to standard pharmaceutical procedures in cell cultures and/or experimental animals, including, for example, determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Therapies that exhibit large therapeutic indices are preferred.

The data obtained from cell culture and/or animal studies can be used in formulating a range of dosages for humans. The dosage of the active ingredient typically lines within a range of circulating concentrations that include the ED50 with low toxicity. The dosage can vary within this range depending upon the dosage form employed and the route of administration utilized.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

The effective amount of a therapeutic composition to be given to a particular patient will depend on a variety of factors, several of which will differ from patient to patient. A competent clinician will be able to determine an effective amount of a therapeutic agent to administer to a patient to halt or reverse the progression the disease condition as required. Utilizing LD50 animal data, and other information available for the agent, a clinician can determine the maximum safe dose for an individual, depending on the route of administration. For instance, an intravenously administered dose may be more than an intrathecally administered dose, given the greater body of fluid into which the therapeutic composition is being administered. Similarly, compositions which are rapidly cleared from the body may be administered at higher doses, or in repeated doses, in order to maintain a therapeutic concentration. Utilizing ordinary skill, the competent clinician will be able to optimize the dosage of a particular therapeutic in the course of routine clinical trials.

Utility

The subject nucleic acids (e.g., expression vectors) may be used to achieve persistent, high level expression of a transgene of interest in eukaryotic cells (e.g., mammalian cells). By high level expression, it is meant that the transgene is expressed by a host cell at a level that is 50-fold greater, 100-fold (2-log) greater, 1000-fold (3-log) greater, or 10,000 fold (4-log) greater or more, within the first 1, 2, or 3 days following introduction into a cell than in the absence of vector. By persistent, it is meant that high level expression of the transgene persists for 2 weeks or more, for example, 3 weeks or more (e.g., 4 weeks or more, 5 weeks or more, 6 weeks or more, 7 weeks or more, 8 weeks or more, 9 weeks or more, 10 weeks or more, 12 weeks or more, 18 weeks or more, or 6 months or more). In other words, the expression level of the transgene does not decrease more than 100-fold, more usually not more than 50-fold, in some instances, not more than 10-fold in the 2 weeks or more (e.g., 3 weeks or more, 4 weeks or more, 5 weeks or more, 6 weeks or more, 7 weeks or more, 8 weeks or more, 9 weeks or more, 10 weeks or more, 12 weeks or more, 18 weeks or more, or 6 months or more) following introduction into a cell from levels observed within the first 1, 2, or 3 days. This is in contrast to standard plasmids, that is, circular vectors comprising plasmid backbone sequences that do not include a subject non-silencing selectable marker gene (e.g., such vectors have a bacterial origin of replication and a selectable marker gene). For example, as demonstrated in the working examples below, whereas expression of a transgene from a plasmid is expected to decrease by roughly 50-fold or more from initial levels by 3 weeks after introduction into a cell, expression of a transgene from a subject expression vector (e.g., an expression vector that includes a non-silencing selectable marker gene) may be expected to decrease less than 10-fold from initial levels in that same time period. As such, a subject expression vector (e.g., an expression vector that includes a non-silencing selectable marker gene) may provide for expression that is 5-fold greater or more, e.g., 10-fold greater more, 50-fold greater or more, in some instances 100-fold greater, than expression from a vector comprising an origin of replication and selectable marker that is not a non-silencing selectable marker gene. In some instances, the subject methods comprise the step of measuring the expression level of the transgene, e.g. 3 weeks or more after introducing a subject vector into the cell, wherein the expression level is at least 10-fold more than a transgene expressed from a plasmid comprising an origin of replication and a selectable marker that is not a non-silencing selectable marker gene.

The inclusion of a non-silencing selectable marker gene (and in some cases a bacterial origin of replication, e.g., in some cases where the vector is a plasmid) on the expression vector provides several advantages as compared to minicircle vectors. For example, these elements allow plasmids to be propagated in bacteria. Additionally, the vectors may be produced using standard vector preparation protocols (e.g., plasmid preparation protocols) without need for integrase-mediated steps to remove sequences from the vector, and therefore without the need for specialized purification protocols.

The subject compositions and methods find use in a variety of applications in which the introduction of a nucleic acid into a target cell is desired. Applications in which the subject vectors and methods find use include research applications, RNA or polypeptide synthesis applications, and therapeutic applications. Each of these representative categories of applications is described separately below in greater detail.

Research Applications

Examples of research applications in which the subject compositions and methods find use include applications designed to characterize a particular transgene (e.g., a protein-coding gene, a non-protein coding gene). In such applications, the subject vectors may be employed to introduce and express a transgene of interest in a target cell and the resultant effect of the transgene on the cell's phenotype can be observed. For example, the subject vectors may be employed to introduce and express a nucleic acid sequence encoding an shRNA or sRNA that is specific for a gene of interest in a target cell, and the resultant effect of inhibiting the expression of the target gene on the cell's phenotype can be observed. In this manner, information about the gene's activity and the nature of the product encoded thereby can be deduced. One can also employ the subject methods to produce models in which overexpression and/or misexpression of a transgene is produced in a cell and the effects of this expression can be observed.

RNA and Polypeptide Synthesis Applications

In addition to the above research applications, the subject compositions and methods (e.g., a subject expression vector) also find use in the synthesis of polypeptides, e.g. proteins of interest, and RNAs, e.g. sRNA or miRNA of interest. In such applications, a subject expression vector that includes a gene encoding the transgene of interest in combination with requisite and/or desired expression regulatory sequences, e.g. promoters, etc., (i.e. an expression module) is introduced into the target cell, e.g. via in vitro contacting of the cell with the subject expression vector, or via in vivo administration to a multicellular organism in which the target cell resides, that is to serve as an expression host for expression of the transgene. Following administration, the transformed cell is maintained under conditions sufficient for expression of the transgene. The expressed RNA or protein can then be harvested, and purified where desired, using any convenient protocol.

As such, the subject methods provide a means for at least enhancing the amount of a protein or RNA of interest in a unicellular or multicellular organism. The term 'at least enhance' includes situations where the methods are employed to increase the amount of a protein or RNA in a unicellular or multicellular organism where a certain initial amount of protein or RNA is present prior to in vivo administration of the vector. The term 'at least enhance' also includes those situations in which the unicellular or multicellular organism includes substantially none of the protein or RNA prior to administration of the vector. By "at least enhance" is meant that the amount of the particular protein or RNA present in the host is increased by at least about 2 fold, usually by at least about 5 fold and more usually by at least about 10 fold. As the subject methods find use in at least enhancing the amount of a protein or RNA present in a unicellular or multicellular organism, they find use in a variety of different applications, including agricultural applications, pharmaceutical preparation applications, e.g. large scale production of protein or RNA therapeutic agents, and the like, as well as therapeutic applications.

Therapeutic Applications

The subject methods and compositions also find use in therapeutic applications, in which the subject expression vectors are employed to introduce a therapeutic nucleic acid (e.g., protein coding gene, shRNA, sRNA, miRNA, etc.) into a target cell (i.e., in gene therapy applications) to provide for persistent expression of the product encoded by the nucleic acid (the transgene) present on the vector. The subject expression vectors may be used to deliver a wide variety of therapeutic nucleic acids. Therapeutic nucleic acids of interest include genes that replace defective genes in the target host cell, such as those responsible for genetic defect based diseased conditions; genes which have therapeutic utility in the treatment of cancer; and the like. Specific therapeutic genes for use in the treatment of genetic defect based disease conditions include genes encoding the following products: factor VIII, factor IX, β-globin, low-density lipoprotein receptor, adenosine deaminase, purine nucleoside phosphorylase, sphingomyelinase, glucocerebrosidase, cystic fibrosis transmembrane conductor regulator, α1-antitrypsin, CD-18, ornithine transcarbamylase, argininosuccinate synthetase, phenylalanine hydroxylase, branched-chain α-ketoacid dehydrogenase, fumarylacetoacetate hydrolase, glucose 6-phosphatase, α-L-fucosidase, β-glucuronidase, α-L-iduronidase, galactose 1-phosphate uridyltransferase, and the like, where the particular coding sequence of the above proteins that is employed will generally be the coding sequence that is found naturally in the host being treated, i.e., human coding sequences are employed to treat human hosts. Cancer therapeutic genes that may be delivered via the subject methods include: genes that enhance the antitumor activity of lymphocytes, genes whose expression product enhances the immunogenicity of tumor cells, tumor suppressor genes, toxin genes, suicide genes, multiple-drug resistance genes, antisense sequences, and the like.

The subject methods and compositions also find use in the expression of RNA products, e.g., shRNA, miRNA, antisense RNA, ribozymes etc., as described in Lieber et al., "Elimination of hepatitis C virus RNA in infected human hepatocytes by adenovirus-mediated expression of ribozymes," J Virol. (1996 December) 70(12):8782-91; Lieber et al., "Related Articles Adenovirus-mediated expression of ribozymes in mice," J Virol. (1996 May) 70(5):3153-8; Tang et al., "Intravenous angiotensinogen antisense in AAV-based vector decreases hypertension," Am J Physiol. (1999 December) 277(6 Pt 2):H2392-9; Horster et al. "Recombinant AAV-2 harboring gfp-antisense/ribozyme fusion sequences monitor transduction, gene expression, and show anti-HIV-1 efficacy, Gene Ther. (1999 July) 6(7):1231-8; and Phillips et al., "Prolonged reduction of high blood pressure with an in vivo, nonpathogenic, adeno-associated viral vector delivery of AT1-R mRNA antisense," Hypertension. (1997 January) 29(1 Pt 2):374-80. As such, the subject methods can be used to deliver therapeutic RNA molecules, e.g., antisense, ribozyme, etc., into target cells of the host.

The subject methods and compositions also find use in the expression in somatic cells of genes that encode reprogramming factors or transdifferentiation factors. By "reprogramming factors", it is meant factors, e.g. proteins, RNAs, etc., for example, Oct3/4, Sox2, Klf4, c-Myc, Nanog, Lin-28, miR302/367, that reprogram somatic cells to become induced pluripotent stem cells (iPS cells), e.g. human iPS cells. By "transdifferentiation factors" it is meant factors, e.g. proteins, RNAs, etc., that induce somatic cells to transdifferentiate into induced somatic cells of another lineage without undergoing an intermediate pluripotent state; see, e.g. PCT Application Publication No. WO 2011/091048, the full disclosure of which is incorporated herein by reference. In addition, the subject methods and compositions also find use in the expression of genes in stem or progenitor cells that direct the development of stem or progenitor cells into desired cell fates. iPS cells and somatic cells that are induced to differentiate from somatic cells or pluripotent cells find many experimental and therapeutic uses, as known in the art.

An important feature of the subject methods, as described supra, is that the subject methods may be used for in vivo gene therapy applications. By in vivo gene therapy applications is meant that the target cell or cells in which expression of the therapeutic gene is desired are not removed from the host prior to contact with the vector system. In contrast, the subject expression vectors can be administered directly to the multicellular organism and can be taken up by the target cells, following which expression of the transgene in the target cell occurs.

Generating a Non-silencing Selectable Marker Gene

In some embodiments, a subject method includes generating a subject non-silencing selectable marker gene sequence. In some cases, such a method includes modifying a first nucleotide sequence that encodes a first selectable marker protein (e.g., a wild type nucleotide sequence that encodes a selectable marker gene, e.g., a drug selectable marker gene) to arrive at a second nucleotide sequence (a non-silencing selectable marker gene) that encodes a second selectable marker protein, where the second selectable marker protein has the same biochemical function (e.g., provides drug resistance to the same drug) as the first selectable marker protein. In some cases, the second selectable marker protein includes an amino acid sequence having 80% or more identity (e.g., 85% or more, 90% or more, 95% or more, 98% or more, 99% or more, 99.5% or more, or 100% identity) with the amino acid sequence of the first selectable marker protein. In some cases, the second selectable marker protein includes an amino acid sequence having 99% or more identity (e.g., 99.5% or more, or 100% identity) with the amino acid sequence of the first selectable marker protein. Thus, in some cases, the second selectable marker protein is identical to the first selectable marker protein. However, the second nucleotide sequence (which encodes the second selectable marker protein) will be different than the first nucleotide sequence (which encodes the first selectable marker protein).

This method can be similar to codon optimization in the sense that codons of the first nucleotide sequence can be modified in order to generate the second nucleotide sequence, without modifying the encoded amino acid sequence (or modifying the encoded amino acid sequence slightly without altering the biochemical function of the protein). However, the nucleotide sequence changes that are introduced are not introduced for the purpose of increasing translation efficiency of the nucleotide sequence in the organism in which is expressed. For example, in some cases the second nucleotide sequence will be operably linked to a prokaryotic promoter and will be expressed in prokaryotic cells to provide selection (e.g., drug resistance) for the prokaryotic cells, but the modifications are introduced in order to affect expression of a different gene, a transgene, when an expression vector (one that includes the second nucleotide sequence and the transgene) is introduced into eukaryotic cells (e.g., mammalian cells). Thus, the changes are introduced to increase (in trans) the expression of a transgene (i.e., to refrain from silencing expression of the transgene), which is a third nucleotide sequence, that is operably linked to a promoter (e.g., functional in a eukaryotic cell).

When generating a subject non-silencing selectable marker gene sequence, the first nucleotide sequence can be modified in a number of different ways. For example, the first nucleotide sequence can be modified to change any combination of the following parameters: A/T content (e.g., increase A/T content), T:A ratio, the presence and/or number and/or length of PolyT tracts, the presence and/or number and/or length of PolyA tracts, the presence and/or number and/or length of Poly-A/Poly-T tracts, and the presence and/or number and/or type of Pol II pause sites. The types of possible changes for each of these parameters is described in more detail above with regard to subject non-silencing selectable marker genes, and is not repeated here.

The first nucleotide sequence can be any selectable marker gene. In some cases, the first nucleotide sequence encodes a selectable marker protein (e.g., a drug selectable marker gene). In some cases, the first nucleotide sequence encodes a drug selectable marker protein that provides resistance for prokaryotic cells to one or more drugs selected from: kanamycin, neomycin, ampicillin, carbenicillin, chloramphenicol, gentamicin, tetracycline, rifampin, trimethoprim, hygromycin B, and spectinomycin (described in more detail above).

Kits

Also provided are kits, e.g., for preparing one or more of the above compositions and for practicing one or more of the above-described methods. The contents of the subject kits may vary greatly. A kit can include one or more of: a subject expression vector (e.g. circular or linear), a subject nucleic acid (e.g., a nucleic acid encoding a non-silencing selectable marker gene for the purpose of replacing a standard selectable marker gene in given vector with the non-silencing selectable marker gene), a diluent, a positive control vector, a negative control vector, and frozen cells for transformation with the a subject expression vector. In some cases, the expression vector of a kit includes an insertion site in addition to or instead of a transgene in the expression cassette (as described above). In some cases, a kit includes two or more (3 or more, 4 or more, etc.) subject expression vectors, where each expression vector of the kit includes a different non-silencing selectable maker gene (e.g, each expression vector can have a non-silencing selectable marker gene that encodes for a different drug selectable marker protein, e.g., that each provide for resistance to different drugs selected from: kanamycin, neomycin, ampicillin, carbenicillin, chloramphenicol, gentamicin, tetracycline, rifampin, trimethoprim, hygromycin B, and spectinomycin). In some cases, a kit includes one or more nucleic acids encoding two or more non-silencing selectable marker genes.

In addition to the above components, the subject kits can further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, flash drive, etc., on which the information has been recorded. Yet another means that may be present is a website address which may be used via the internet to access the information at a removed site. Any convenient means may be present in the kits.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

"J-Kan" Functions as a Non Silencing Selectable Marker Gene

Plasmid DNA transgene silencing in vivo can be observed when ~1 kb or more of DNA is placed outside of the transcription expression cassette (between the 5' end of promoter and the 3' end of polyA site), even when the bacterial plasmid DNA sequences are replaced with random DNA sequences (Lu, J, et. al., 2012 Mol Ther 20:2111-2119). These findings indicated that the length of the backbone and not anything specific about the bacterial plasmid DNA itself is the critical determinant responsible for transgene silencing in vivo. Based on this, a new transgene expression system was produced (called a "mini-intronic plasmid (MIP)") that places the bacterial replication origin and selectable marker as a intron in the transgene expression cassette, but still keeps the juxtaposition of the 5' and the 3' ends of transgene expression cassette, as in a minicircle (Lu, J, et. al., 2013 Mol Ther 21: 954-963) (US Patent application US20130210897).

Our previous findings demonstrated that the length of the backbone was important for determining whether transgene expression is silenced or sustained in vivo. The studies described here were initiated to investigate what molecular ruler is used to measure the length of backbone and what mechanism is regulating transgene silencing in vivo. The nucleosome is the basic DNA packaging unit of chromatin. The nucleosome core particle is formed by approximately 147 base pairs of DNA wrapped around a histone octamer. These features of nucleosome make it an ideal molecular ruler to measure the length of DNA. To be able to wrap around the histone octamer, the DNA sequence has to be flexible to allow it to circle around the histone octamer. Published studies have shown that certain DNA sequence patterns are too rigid to form this circle. These patterns include poly-A and poly-T tracks (Travers AA, Klug A, Cold Spring Harbor Laboratory Press: 1990; 57-106). Base on the knowledge of nucleosome, the studies were designed to ask whether the association of nucleosome with the plasmid backbone sequence determined the transgene expression pattern in vivo. For example, experiments were performed to test whether long backbone (>1 kb) associates with higher numbers of nucleosomes than short backbone, and whether increased nucleosomes associating with plasmid backbone causes decreased persistence and/or levels of transgene expression. To this end, a 2.2 kilobase pair nucleosome exclusion sequence (NES) was synthesized by inserting 20 base pairs of 'T' in every 60 base pairs of random DNA sequence (FIG. 1). This NES sequence was then tested for its ability to sustain transgene expression as backbone in vivo. Thus, the NES sequence was used in the backbone to prevent transgene silencing in vivo. The results indicated that by inserting poly-T tracks, this NES fragment is able to allow persistent transgene expression in vivo, suggesting that the nucleosome association with the plasmid backbone silences the transgene.

Results

Figure 3:
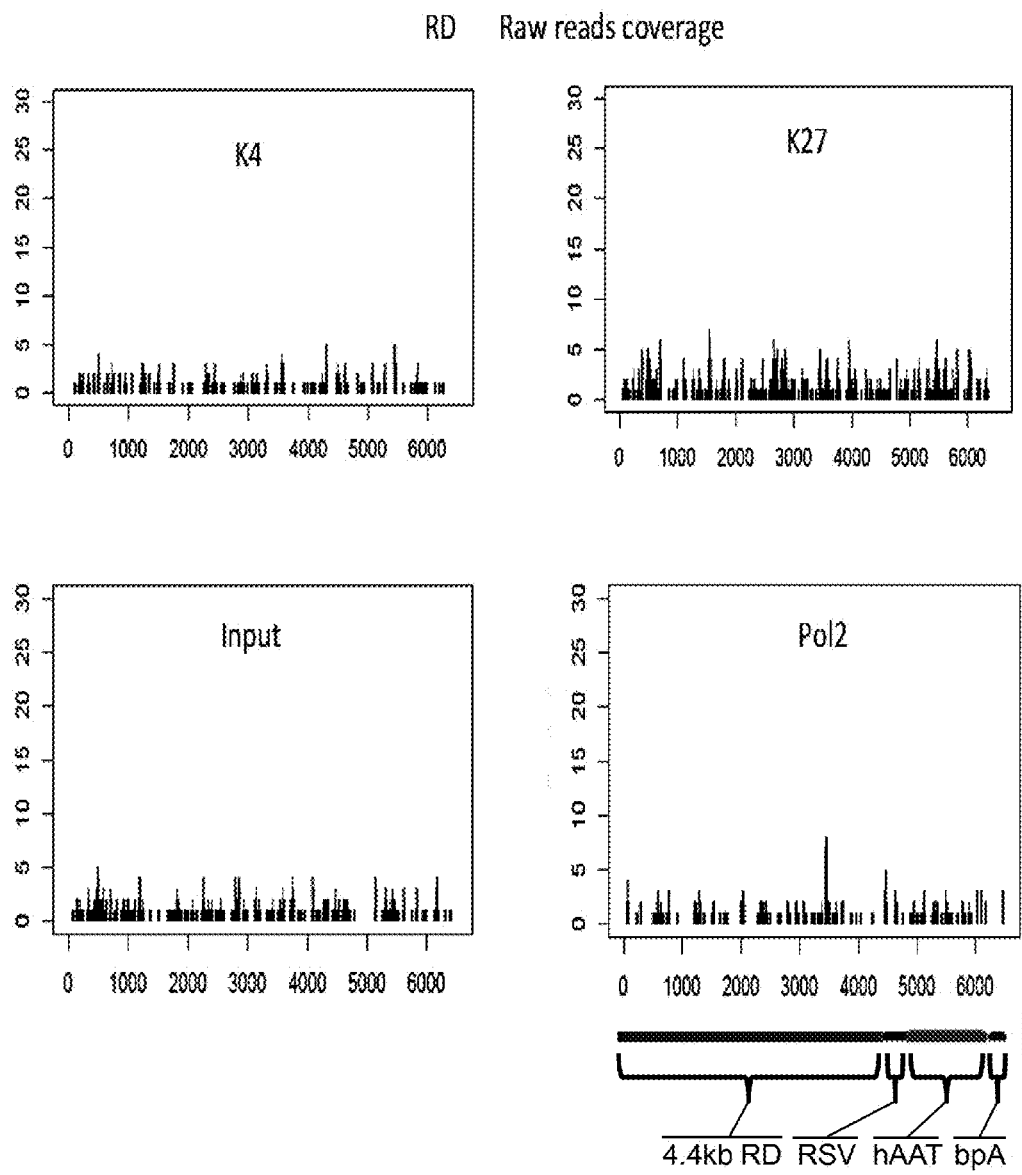
FIGS. 3A-3B: Analyzed Chip-Seq experiment results. The X-axis represents the position of the reads on the DNA vector. The Y-axis represents the number of raw reads.
Figure 3:
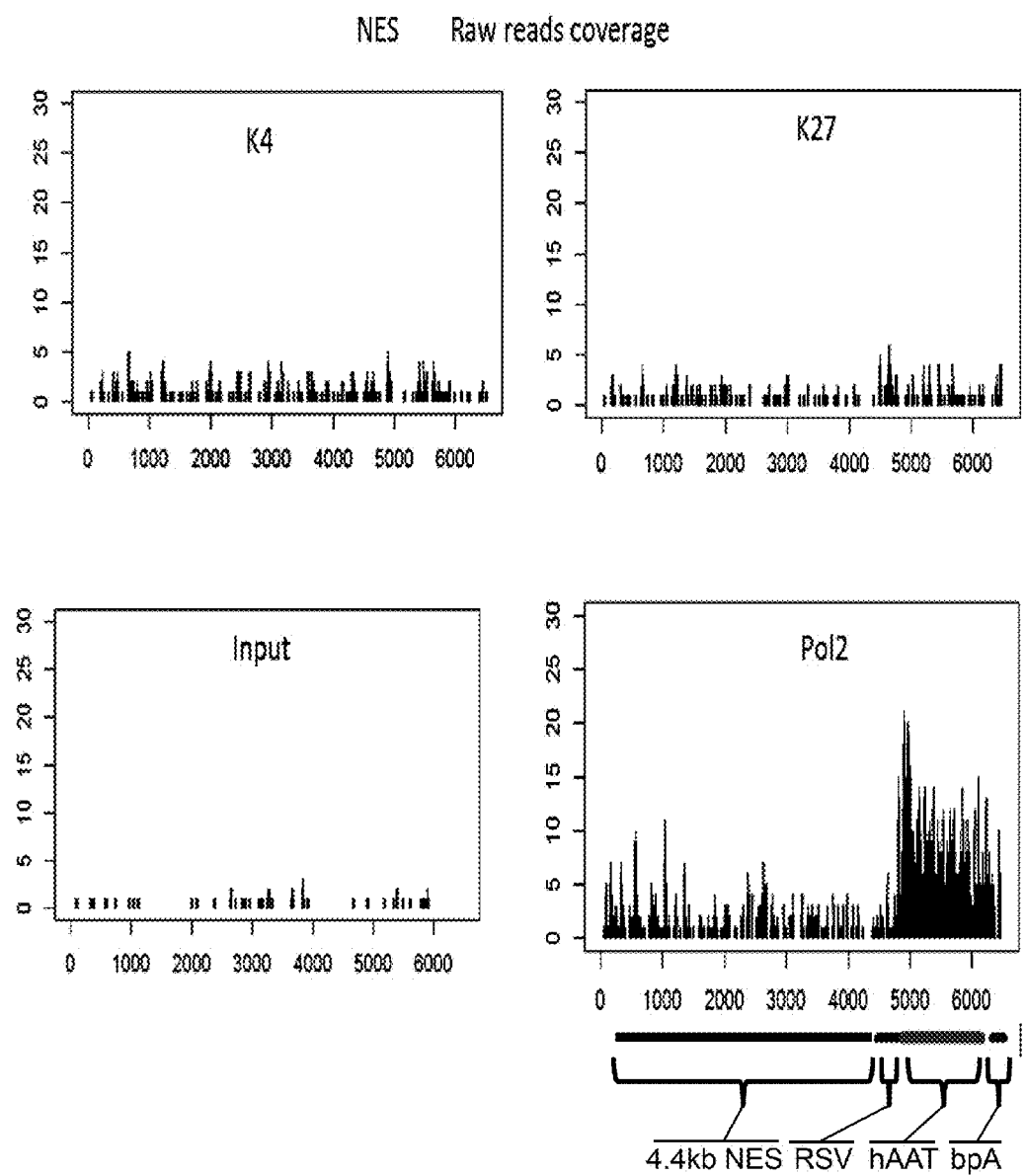

The NES sequence was originally designed to exclude nucleosome binding. To verify the exclusion efficiency of the NES sequence, a Chip-Seq experiment was performed to directly detect the DNA fragment that associates with nucleosome. As shown in FIG. 2, mice infused with a minicircle vector that contains two copies of 2.2 kb random DNA as backbone (MC.RHB-4.4 kb RD) were not able to persistently express human alpha 1-antitrypsin (hAAT) and produced a similar transgene expression pattern as silenced plasmid DNA vector (pRHB). In contrast, mice infused with minicircle vector that contains two copies of 2.2 kb NES as backbone (MC.RHB-4.4 kb NES) sustained high levels of hAAT, similar to a minicircle vector without any backbone (MC.RHB). Mouse liver samples from these mice were harvested 9 weeks after infused with MC.RHB-4.4 kb RD and MC.RHB-4.4 kb NES. As shown in FIG. 3, the Chip-Seq experiment detected similar amounts of H3K4 signals of nucleosome in both MC.RHB-4.4 kb RD and MC.RHB-4.4 kb NES infused animals. Higher H3K27 signals of nucleosome were detected in MC.RHB-4.4 kb RD infused samples (FIG. 3A) than in MC.RHB-4.4 kb NES infused samples (FIG. 3B). The nucleosome signals were still detected from MC.RHB-4.4 kb NES infused samples, indicating that the NES sequence still associates with nucleosomes. Thus, despite the name "nucleosome exclusion sequence," nucleosomes appear to associate with these sequences. It is possible that the association between nucleosomes and the NES sequence is weaker than with the RD sequence. However the Chip-Seq condition in the performed experiment provides no evidence that these sequences referred to as "nucleosome exclusion sequences" actually have any effect on nucleosome patterning in a plasmid delivered into a living cell.

Surprisingly, significant differences of RNA polymerase II (Pol2) signals (binding of RNA Pol2) were detected between MC.RHB-4.4 kb RD and MC.RHB-4.4 kb NES infused animals. In MC.RHB-4.4 kb NES infused samples, strong Pol2 signals were accumulated along the transgene expression cassette due to sustained transgene expression. Significant Pol2 signals were also detected in the 4.4 kb NES backbone region. However in MC.RHB-4.4 kb RD infused samples, Pol2 signals were greatly reduced (compared to MC.RHB-4.4 kb NES infused samples) in both the transgene expression cassette region and the 4.4 kb RD backbone region.

Although the Chip-Seq results suggested that the NES sequence still associated with nucleosomes, this result provided a new direction for additional studies. The different distribution of Pol2 signals along MC.RHB-4.4 kb RD and MC.RHB-4.4 kb NES vectors suggested that unexpected transcription might occur on the NES backbone but not the RD backbone. Experiments were designed to address whether this difference of Pol2 distribution along the backbone is important for transgene expression. Reverse transcription (RT) followed by quantitative PCR (qPCR) was performed to detect the transcription products from the NES and RD backbone. FIG. 4A schematically depicts the primers that were designed to detect transcripts [short sense strand transcripts (SSS) and short antisense strand transcripts (SAS)] from the NES and RD backbone. As shown in FIG. 4B, both sense transcripts and antisense transcripts were successfully amplified through RT-qPCR experiments. The NES backbone generated significantly higher transcription activities at both sense and antisense orientations when compared with transcription from the RD backbone (note the difference in the scale of the Y axis in FIG. 4B)(FIG. 4C). Significantly more transcripts were detected from the sense strand orientation than the antisense strand orientation (for both the NES backbone and the RD backbone). These results strongly suggest that Pol2 moves from the transgene expression cassette into the backbone from both sense and antisense orientations and is still able to transcribe the DNA sequence of the backbone. However the NES sequence is able to maintain more Pol2 and thus generates more abundant transcripts then the RD sequence.

Figure 5D:
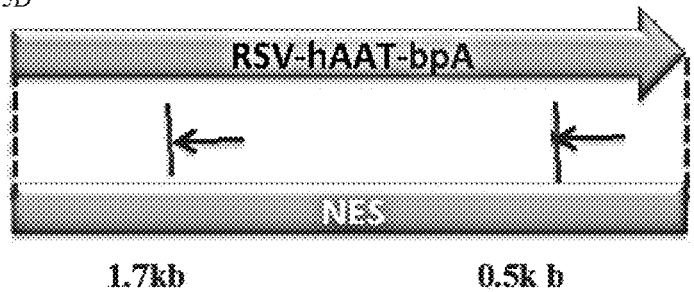
Figure 5E:
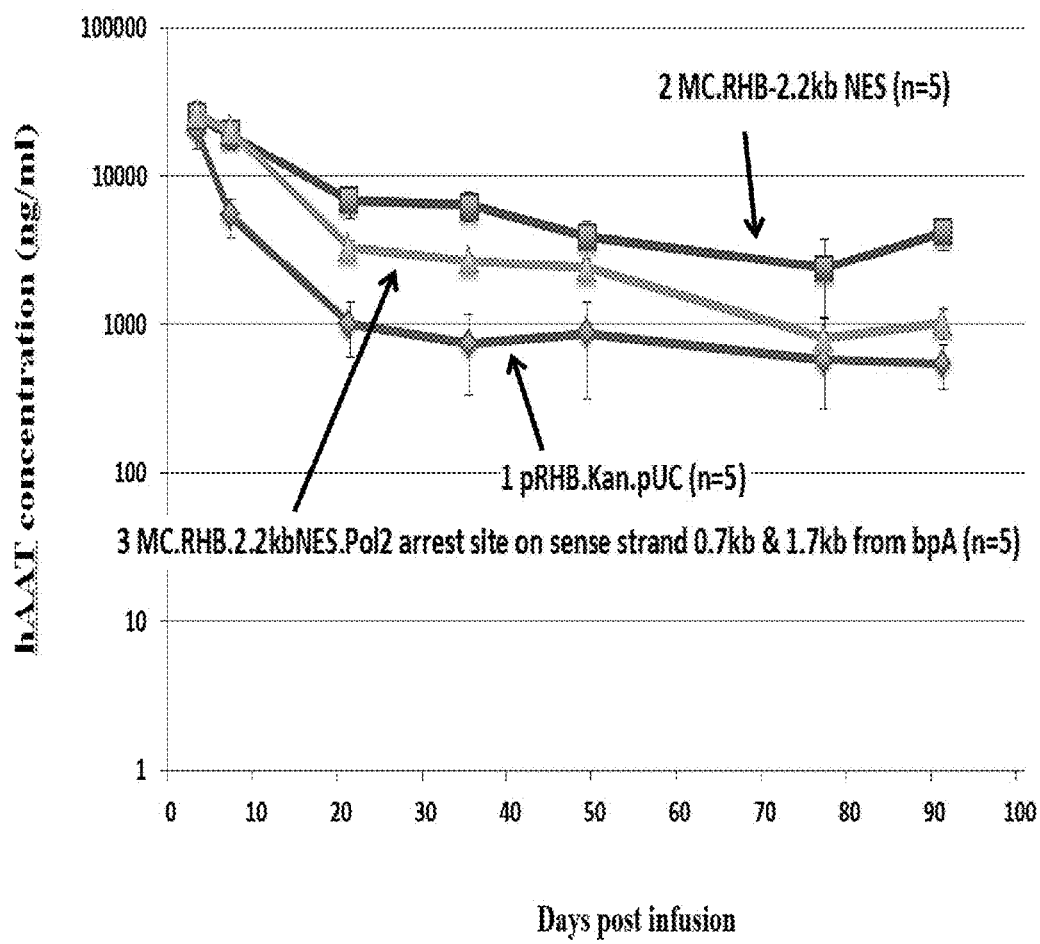

These studies have shown that when transgene expression is sustained in the NES vector, Pol2 associates with the plasmid backbone and generates transcripts from plasmid backbone. It remained possible that if the transcription of Pol2 was blocked in the NES backbone, then expression of the transgene would be silenced. To test this possibility, the mammalian histone H3.3 Pol2 arrest site was incorporated into the NES sequence. This site contains the sequence TTTTTTTCCCTTTTTT (SEQ ID NO: 17) in the non-template strand (Reines D., et. al., 1987 *Mol. Biol.*, 196: 299-312), and can block transcription elongation by Pol2 such that Pol2 cannot continue RNA synthesis in a standard experimental time course (Peter H., et. al., 2004 *Nucleic Acids Res.* 32(6):1904-1916). As indicated in FIG. 5, when two copies of histone H3.3 Pol2 arrest sites were incorporated into the NES backbone (either sense or antisense strand), expression of the transgene was reduced (silenced). This strongly suggested that the transcription activities of the backbone sequence impact transgene expression from the expression cassette (RSV-hAAT-bpA).

Figure 7:
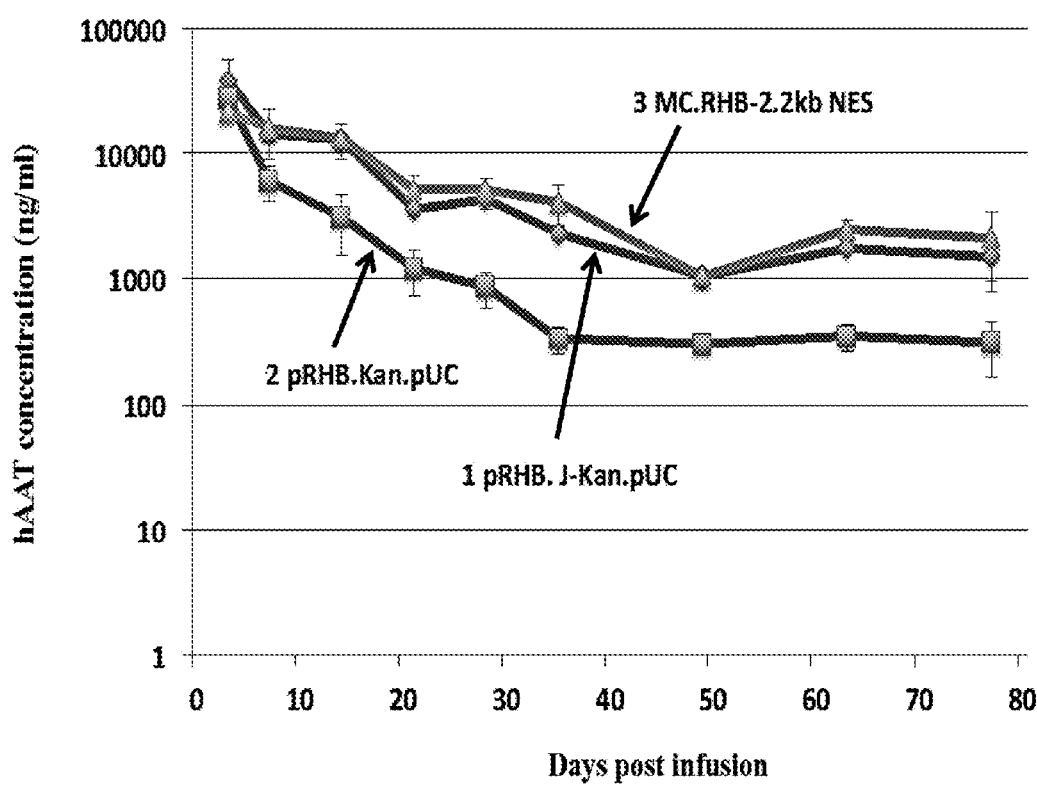
FIG. 7: Serum hAAT levels at various time points after equimolar infusion the plasmid vectors through hydrodynamic tail vein injection in mice (n=5 mice per group). Error bars represent the standard deviation. This figure indicates that while wild type Kanamycin resistance gene (Kan)(when used as part of the plasmid backbone sequence) silenced the transgene (hAAT), the modified Kanamycin (J-Kan) (when used as part of the plasmid backbone sequence) facilitated/supported transgene expression of the transgene (hAAT), to similar levels as when the transgene was expressed from a minicircle vector (a vector without bacterial plasmid backbone sequences).

It was then tested whether poly-T/poly-A tracks incorporated into the plasmid bacterial backbone would facilitate increased transgene expression from the expression cassette and therefore convert a silencing vector (with bacterial backbone) into a non-silencing vector (with modified bacterial backbone). A plasmid bacterial backbone includes a bacterial replication origin and a selectable marker. Thus, these sequences were possible sequences for modification. Bacterial replication origins contain sequences that attract replication initiator proteins, and these AT rich regions were found to be the essential elements of replication origins of bacterial replicons (Rajewska M., et. al., 2012 *FEMS Microbiol Rev.* 36(2):408-34). Thus, the selectable marker (Kanamycin in this case) became the focus for modification. The Kanamycin resistant gene (Kan) as a commonly used selectable marker in many plasmid vectors and was chosen to be the target sequence for modification. As shown in FIG. 6, about 30% of the Kan sequence was changed from G/C into A/T while maintaining codons that would be translated into the same amino acids. Thus, the modified DNA sequence (J-Kan) encodes the identical protein as the unmodified DNA sequence (Kan). The modified Kan sequence, J-Kan, was incorporated into plasmid backbone and the resulting vector was tested for its ability to facilitate transgene expression by infusing mice with the vector. The animal test results demonstrate that expression from the J-Kan containing vector (pRHB.J-Kan.pUC) was comparable (high expression levels for a long period of time) to the mini-circle vector containing the 2.2 kb NES (MC.RHB-2.2 kb NES)(which was shown in FIG. 2 to express transgene at levels comparable to a standard minicircle vector), both of which expressed much higher levels of transgene than the vector containing the unmodified Kan gene (pRHB.Kan.pUC). In other words, when the conventional Kan sequence was replaced by the J-Kan sequence depicted in FIG. 6, transgene expression was sustained at a similar levels as minicircle vector for a comparable length of time (FIG. 7).

The nucleotide sequence depicted in FIG. 8 ("JT-Kan") (SEQ ID NO: 5) was modified relative to the wild type sequence of FIG. 6 (which encodes a drug selectable marker protein that provides for resistance to kanamycin) (SEQ ID NO: 2) to be "T" rich. However this modified kanamycin resistance sequence was not able to allow the tested bacteria to grow on kanamycin selectable plates. This suggests that this sequence may not be expressed correctly (e.g., the encoded kanamycin resistance protein might not be expressed at high enough levels to provide drug resistance, perhaps due to inefficient translation). In other words, the JT-Kan sequence did not function as a "selectable marker gene" in this experiment because it did not provide resistance for the tested prokaryotic cells to kanamycin, despite encoding the same protein as J-Kan.

In summary, the J-Kan selectable marker transformed a silencing plasmid vector into a non-silencing plasmid vector. Thus, vectors that include a nucleotide sequence that is modified to increase the number A/T pairs (e.g., also increasing the number of poly-T/poly-A tracts) while still encoding a functional selectable marker protein, can express sustained high levels of transgenes. Non-silencing vectors with sequences modified in this way (e.g., sequences that still encode a selectable marker protein and that still function as selectable marker genes) can be otherwise identical to conventional vectors in terms of structure and in terms of methods of their preparation. Thus, this approach provides the convenience of using standard vectors and standard preparation methods while achieving comparable sustained high levels of transgene expression, comparable to that observed with minicircle vectors.

The modified antibiotic resistance gene (J-Kan) did not alter the ability of the plasmid to be propagated in standard bacterial culture. Table 10 shows the yield of plasmid vectors with modified antibiotic resistance genes as part of the plasmid backbone sequence and conventional plasmid vectors (n=4 per vector). The yield was derived from quadruplicate 100 ml overnight cultures.

TABLE 10

| | Yield of plasmid vectors | | |
|---|---|---|---|
| DNA vector | Size (kb) | Vector yield (mg/l) | Vector yield ($10^{-9}$ mol/l) |
| pRHB.pUC.Kan | 3.9 | 7.84 ± 0.36 | 3.05 ± 0.14 |
| pRHB.pUC.J-Kan | 3.9 | 8.65 ± 0.29 | 3.36 ± 0.11 |

Example 2

"J-Amp" Functions as a Non Silencing Selectable Marker Gene

Figure 10:
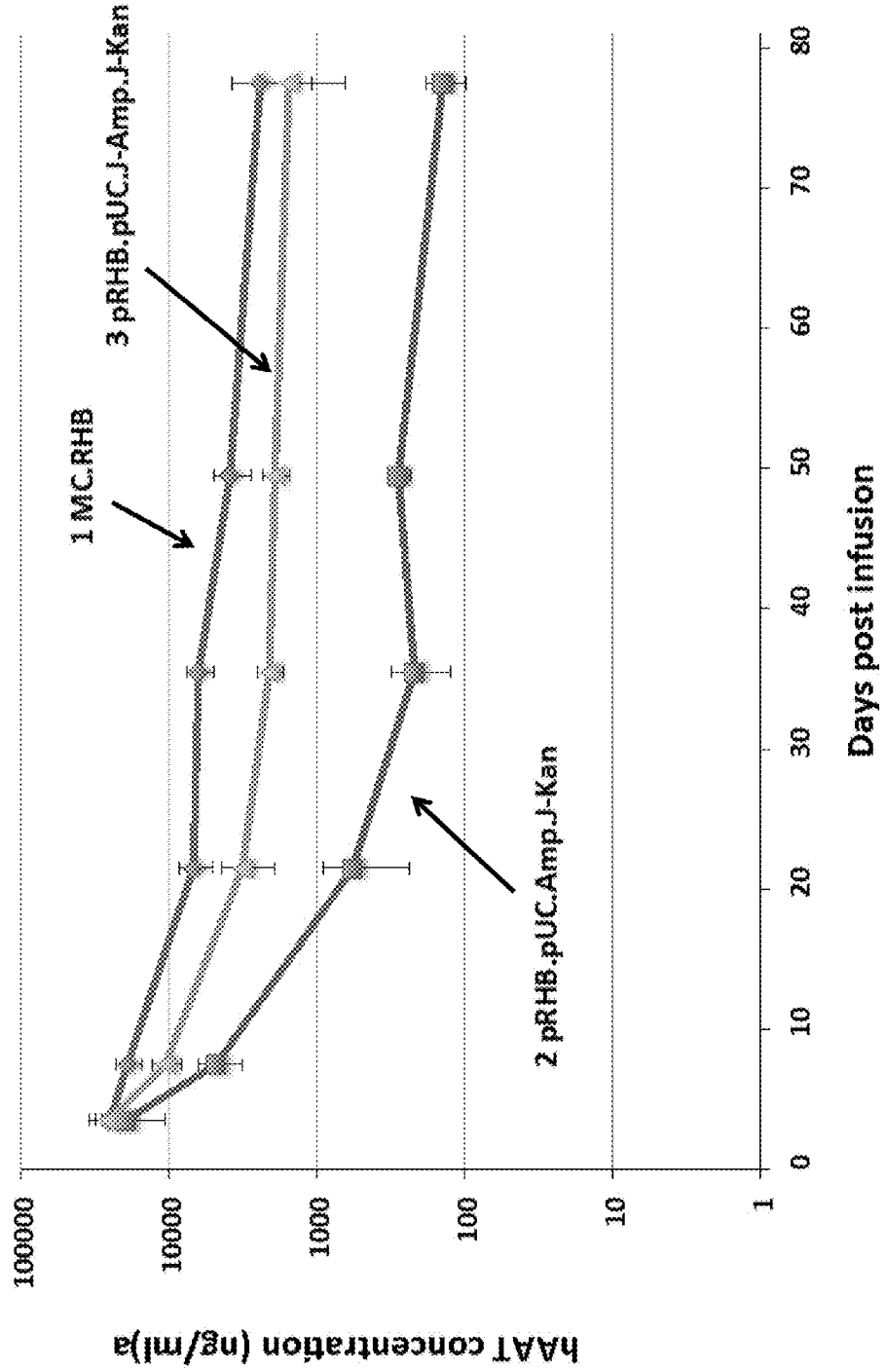
FIG. 10: The codons of the ampicillin resistance gene were modified to incorporate more "A" and "T" residues (J-Amp) (SEQ ID NO: 13) compared to the standard AMP resistance gene (SEQ ID NO: 11). The data show that when J-Amp and J-Kan were both present in the backbone, transgene expression was high and sustained (not silenced). However when non-modified Amp was present in the backbone along with J-Kan, transgene expression was silenced.

Similar to how J-Kan was generated by modifying a wild type Kan resistance gene, "J-Amp" was generated by modifying a wild type Amp resistance gene (See sequences depicted in FIG. 9. The codons of the ampicillin resistance gene were modified to incorporate more "A" and "T" residues while retaining the amino acid sequence of the encoded protein. The data of FIG. 10 show that when J-Amp and J-Kan were both present in the same expression vector backbone, transgene expression was high and sustained (not silenced). However when non-modified Amp (the unmodified wild type sequence) was present in the backbone along with J-Kan, transgene expression was silenced.

Example 3

Design of "J-Tet" as a Non Silencing Selectable Marker Gene

Similar to how J-Kan and J-Amp were generated by modifying wild type Kan and Amp resistance genes, "J-Tet" was generated by modifying a wild type Tet resistance gene (See sequences depicted in FIG. 11. The codons of the tetracycline resistance gene were modified to incorporate more "A" and "T" residues while retaining the amino acid sequence of the encoded protein.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

That which is claimed is:

1. An expression vector for transgene expression in eukaryotic cells, comprising:
   (a) an expression cassette comprising a transgene operably linked to a promoter functional in eukaryotic cells; and
   (b) a non silencing selectable marker gene that comprises a nucleotide sequence that: (i) encodes a drug selectable marker protein that provides resistance for prokaryotic cells to kanamycin; (ii) is operably linked to a promoter functional in prokaryotic cells, (iii) comprises a T:A ratio in a range of from 1.2 to 1.9 and an A/T content of 54% or more, and (iv) has 85% or more nucleotide sequence identity with the sequence set forth in any one of SEQ ID NOs: 3 and 4.

2. The expression vector according to claim 1, wherein said A/T content is in a range of from 54% to 68%.

3. The expression vector according to claim 1, wherein the nucleotide sequence encoding the drug selectable marker protein comprises 2 or fewer instances of the following Polymerase II (Pol II) pause site: TTATT.

4. The expression vector according to claim 1, wherein the nucleotide sequence encoding the drug selectable marker protein does not comprise any of the following Polymerase II (Pol II) pause sites: TTTATT, TTTTTTTCCCTTTTTT (SEQ ID NO: 17), and AAAAAAGGGAAAAAAA (SEQ ID NO: 18).

5. The expression vector according to claim 1, wherein the transgene is operably linked to a promoter functional in one or more cells selected from: mammalian cells, rodent cells, primate cells, and human cells.

6. The expression vector according to claim 1, wherein the transgene comprises a nucleotide sequence encoding an RNA selected from: a translated RNA, a non-coding RNA, an antisense RNA, a microRNA, an shRNA, and an siRNA.

7. The expression vector according to claim 1, wherein the transgene comprises a nucleotide sequence encoding a protein.

8. A method of expressing a transgene in a eukaryotic cell, the method comprising:
   introducing into a eukaryotic cell an expression vector according to claim 1, wherein the expression vector provides for expression of the transgene once present in the eukaryotic cell.

9. The method according to claim 8, wherein the eukaryotic cell is in culture in vitro.

10. The method according to claim 8, wherein the eukaryotic cell is in culture ex vivo.

11. The method according to claim 8, wherein the eukaryotic cell is in vivo.

12. The method according to claim 8, wherein the eukaryotic cell is a mammalian cell.

13. The method according to claim 8, wherein said introducing comprises administering to an individual a formulation comprising the expression vector.

14. The method according to claim 13, wherein said administering comprises systemic administration.

15. The method according to claim 13, wherein the individual is a mouse or a human.

16. The method according to claim 8, wherein the transgene comprises a nucleotide sequence encoding an RNA selected from: a translated RNA, a non-coding RNA, an antisense RNA, a microRNA, an shRNA, and an siRNA.

17. The method according to claim 8, wherein the transgene comprises a nucleotide sequence encoding a protein.

18. An expression vector for transgene expression in eukaryotic cells, comprising:
   (a) an expression cassette comprising a transgene operably linked to a promoter functional in eukaryotic cells; and
   (b) a non silencing selectable marker gene comprising a nucleotide sequence that (i) encodes a drug selectable marker protein that provides resistance for prokaryotic cells to kanamycin, (ii) is operably linked to a promoter functional in prokaryotic cells, and (iii) comprises the nucleotide sequence set forth in any of SEQ ID NOs: 3 and 4.

19. The expression vector according to claim 18, wherein the transgene is operably linked to a promoter functional in one or more cells selected from: mammalian cells, rodent cells, primate cells, and human cells.

20. The expression vector according to claim 18, wherein the transgene comprises a nucleotide sequence encoding an RNA selected from: a translated RNA, a non-coding RNA, an antisense RNA, a microRNA, an shRNA, and an siRNA.

21. The expression vector according to claim 18, wherein the transgene comprises a nucleotide sequence encoding a protein.

22. A method of expressing a transgene in a eukaryotic cell, the method comprising:
   introducing into a eukaryotic cell an expression vector according to claim 18, wherein the expression vector provides for expression of the transgene once present in the eukaryotic cell.

23. The method according to claim 22, wherein the eukaryotic cell is in culture in vitro.

24. The method according to claim 22, wherein the eukaryotic cell is in culture ex vivo.

25. The method according to claim 22, wherein the eukaryotic cell is in vivo.

26. The method according to claim 22, wherein the eukaryotic cell is a mammalian cell.

27. The method according to claim 22, wherein said introducing comprises administering to an individual a formulation comprising the expression vector.

28. The method according to claim 27, wherein said administering comprises systemic administration.

29. The method according to claim 27, wherein the individual is a mouse or a human.

30. The method according to claim 22, wherein the transgene comprises a nucleotide sequence encoding an RNA selected from: a translated RNA, a non-coding RNA, an antisense RNA, a microRNA, an shRNA, and an siRNA.

31. The method according to claim 22, wherein the transgene comprises a nucleotide sequence encoding a protein.

* * * * *